(12) United States Patent
Bannister et al.

(10) Patent No.: US 9,656,994 B2
(45) Date of Patent: May 23, 2017

(54) SUBSTITUTED BENZIMIDAZOLES AS NOCICEPTIN RECEPTOR MODULATORS

(71) Applicant: The Scripps Research Institute, La Jolla, CA (US)

(72) Inventors: Thomas D. Bannister, Palm Beach Gardens, FL (US); Claes R. Wahlestedt, Palm Beach, FL (US); Yen Ting Chen, Palm Beach Gardens, FL (US); Shaun P. Brothers, Port St. Lucie, FL (US); Hasib Salah-Uddin, Jupiter, FL (US); Xiaohong Pan, Palm Beach Gardens, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/779,191

(22) PCT Filed: Mar. 21, 2014

(86) PCT No.: PCT/US2014/031485
§ 371 (c)(1),
(2) Date: Sep. 22, 2015

(87) PCT Pub. No.: WO2014/153529
PCT Pub. Date: Sep. 25, 2014

(65) Prior Publication Data
US 2016/0052913 A1  Feb. 25, 2016

Related U.S. Application Data
(60) Provisional application No. 61/804,316, filed on Mar. 22, 2013.

(51) Int. Cl.
| | | |
|---|---|---|
| *C07D 401/14* | (2006.01) | |
| *C07D 451/02* | (2006.01) | |
| *C07D 405/14* | (2006.01) | |
| *C07D 401/04* | (2006.01) | |
| *C07D 417/14* | (2006.01) | |

(52) U.S. Cl.
CPC ......... *C07D 401/14* (2013.01); *C07D 401/04* (2013.01); *C07D 405/14* (2013.01); *C07D 417/14* (2013.01); *C07D 451/02* (2013.01)

(58) Field of Classification Search
CPC .. C07D 401/04; C07D 401/14; C07D 405/14; C07D 417/14; C07D 451/02
See application file for complete search history.

(56) References Cited

U.S. PATENT DOCUMENTS

| | | | |
|---|---|---|---|
| 6,340,681 B1* | 1/2002 | Ito ........................ | C07D 401/04 514/217.04 |
| 6,861,425 B2 | 3/2005 | Ito et al. | |
| 8,877,779 B2 | 11/2014 | Nakano et al. | |
| 2003/0109549 A1* | 6/2003 | Ito ........................ | A61K 31/454 514/322 |
| 2006/0229289 A1 | 10/2006 | Zhu et al. | |

FOREIGN PATENT DOCUMENTS

| | | |
|---|---|---|
| WO | WO-99/36421 A1 | 7/1999 |
| WO | WO-00/08013 A2 | 2/2000 |
| WO | WO-2008/105497 A1 | 9/2008 |
| WO | WO-2014/153529 A1 | 9/2014 |

OTHER PUBLICATIONS

"International Application Serial No. PCT/US2014/031485, International Search Report mailed Aug. 19, 2014", 2 pgs.
"International Application Serial No. PCT/US2014/031485, Written Opinion mailed Aug. 19, 2014", 5 pgs.
"International Application Serial No. PCT/US2014/031485, International Preliminary Report on Patentability mailed Oct. 1, 2015", 7 pgs.
Brothers, Shaun P., et al., "Selective and Brain Penetrant Neuropeptide Y Y2 Receptor Antagonists Discovered by Whole-Cell High-Throughput Screening", Molecular Pharmacology, 77(1), (2010), 46-57.
Chen, Zhengming, et al., "Design and Parallel Synthesis of Piperidine Libraries Targeting he Nociceptin (N/OFQ) Receptor", Bioorganic & Medicinal Chemistry Letters, 13(19), (2003), 3247-3252.
Gould, Philip L, "Salt selection for basic drugs", International Journal of Pharmaceutics, 33(1-3), (1986), 201-217.
Hayashi, Shigenobu, et al., "Novel Non-Peptide Nociceptin/Orphanin FQ Receptor Agonist, 1-[1-(1-Methylcyclooctyl)-4-piperidinyl]-2-[(3R)-3-piperidinyl]-1H-benzimidazole: Design, Synthesis, and Structure-Activity Relationship of Oral Receptor Occupancy in the Brain for Orally Potent Antianxiety Drug", Journal of Medicinal Chemistry, 52(3), (2009), 610-625.
Hayashi, Shigeo, et al., "Discovery of 1-[1-(1-Methylcyclooctyl)-4-piperidinyl]-2-[(3R)-3-piperidinyl]- 1H-benzimidazole: Integrated Drug-Design and Structure—Activity Relationships for Orally Potent, Metabolically Stable and Potential-Risk Reduced Novel Non-Peptide Nociceptin/Orphanin FQ Receptor Agonist as Antianxiety Drug", Chemical Biology & Drug Design, 74(4), (Oct. 2009), 369-381.
Hirao, Akiko, et al., "Pharmacological Characterization of the Newly Synthesized Nociceptin/Orphanin FQ-Receptor Agonist 1-[1-(1-Methylcyclooctyl)-4-piperidinyl]-2-[(3R)-3-piperidinyl]-1H-benzimidazole as an Anxiolytic Agent", J Pharmacol Sci., 106(3), (2008), 361-368.

(Continued)

*Primary Examiner* — Yong Chu
(74) *Attorney, Agent, or Firm* — Geoffrey K. Cooper; Thomas Fitting; Steven M. Reid

(57) ABSTRACT

The invention provides modulators of the nociceptin receptor (NOP), including both agonists and antagonists. A compound of the invention can be a selective modulator of NOP with respect to the μ- and κ-opioid receptors (MOP and KOP), thus providing a therapeutic method for the treatment of conditions wherein selective NOP modulation is medically indicated and MOP or KOP modulation may be less desirable. A compound of the invention can be a NOP full agonist, partial agonist, inverse agonist, positive or negative allosteric modulator, or a functionally biased agonist. A compound of the invention can be used for the treatment of an anxiety state, post-traumatic stress disorder, addictive disorders (including overuse of alcohol, tobacco, and drugs of abuse such as cocaine, amphetamines, and opitates), misregulated food intake and/or energy expenditure, cough, sleep disorders, migraine, pain, depression, or neurodegenerative disorders such as Parkinsons disease or Alzheimers disease.

6 Claims, No Drawings

(56) References Cited

OTHER PUBLICATIONS

Kenakin, Terry, "Functional Selectivity and Biased Receptor Signaling", J Pharmacol Exp Ther, 336(2), (2011), 296-302.

McLeod, R. L., et al., "Pharmacological profile of the NOP agonist and cough suppressing agent SCH 486757 (8-[Bis(2-Chlorophenyl)Methyl]-3-(2-Pyrimidinyl)-8-Azabicyclo[3.2.1]Octan-3-Ol) in preclinical models", HHS Public Access, Author Manuscript, published in final edited form as: Eur J Pharmacol, 630(1-3), (2010), 112-120, (2010), 112-120.

Mustazza, Carlo, et al., "Development of Nociceptin Receptor (NOP) Agonists and Antagonists", Medicinal Research Reviews, 31(4), (Jul. 2011), 605-648.

Palin, Ronald, et al., "Rapid access towards follow-up NOP receptor agonists using a knowledge based approach", Bioorganic & Medicinal Chemistry Letters, 19(22), (2009), 6441-6446.

Satoh, Atsushi, et al., "Identification of an Orally Active Opioid Receptor-like 1 (ORL1) Receptor Antagonist 4-{3-[(2R)-2,3-Dihydroxypropyl]-2-oxo-2,3-dihydro-1H-benzimidazol-1-yl}-1-[(1S,3S,4R)-spiro[bicyclo[2.2.1]heptane-2,1'-cyclopropan]-3-ylmethyl]piperidine as Clinical Candidate", Journal of Medicinal Chemistry, 52(14), (2009), 4091-4094.

Teshima, Koji, et al., "Nonphotic entrainment of the circadian body temperature rhythm by the selective ORL1 receptor agonist W-212393 in rats", Br J Pharmacol., 146(1), (2005), 33-40.

Willand, Nicolas, et al., "Efficient, two-step synthesis of N-substituted nortropinone derivatives", Tetrahedron Letters, 48(29), (2007), 5007-5011.

Zaveri, Nurulain T., et al., "A Novel Series of Piperidin-4-yl-1,3-Dihydroindol-2-ones as Agonist and Antagonist Ligands at the Nociceptin Receptor", Journal of Medicinal Chemistry, 47(12), (2004), 2973-2976.

Zaveri, Nurulain T., et al., "Small-Molecule Agonists and Antagonists of the Opioid Receptor-Like Receptor (ORL1, NOP): Ligand-Based Analysis of Structural Factors Influencing Intrinsic Activity at NOP", The AAPS Journal, 7(2), (2005), E345-E352.

* cited by examiner

SUBSTITUTED BENZIMIDAZOLES AS NOCICEPTIN RECEPTOR MODULATORS

CROSS-REFERENCE TO RELATED APPLICATION

This application is a U.S. national stage application filed under 35 U.S.C. §371 from International Application Serial No. PCT/US2014/031485, which was filed Mar. 21, 2014, and published as WO 2014/153529 on Sep. 25, 2014, and which claims the priority of U.S. provisional application Ser. No. 61/804,316, filed Mar. 22, 2013, which applications and publication are incorporated by reference as if reproduced herein and made a part hereof in their entirety, and the benefit of priority of each of which is claimed herein.

STATEMENT OF GOVERNMENT SUPPORT

This invention was made with government support under 5R01AA017943-02, awarded by the NIH-NIAAA. The U.S. government has certain rights in the invention.

BACKGROUND

Alcohol addiction is a major issue in public health; however the impact of current pharmacotherapies is modest. Other addictive disorders, including the abuse of narcotics and dependence upon tobacco products, also severely burden health care systems due to high prevalence and lack of availability of fully effective treatments. Thus, the identification of the brain mechanisms responsible for addictions and the development of treatments for curbing various addictions are important health care issues.

Nociceptin, a peptide of 17 amino acid residues, is a recently discovered endogenous ligand for what has been termed the orphan receptor opioid receptor-like 1 (ORL1), now referred to as the nociceptin receptor (NOP), a G-protein coupled receptor. Despite the high sequence homology between the NOP and the opioid receptors, most opioids lack high affinity for NOP. Further, the actions of nociceptin, an anti-analgesic, are not antagonized by opioid antagonists such as naloxone. Nociceptin itself resembles certain opioid peptides such as β-endorphin in its amino acid sequence, but it does not significantly bind to the classic opioid receptors. It is believed to modulate the perception of pain in the central nervous system, inter alia.

The nociceptin receptor (NOP) has been identified as a potential target for therapies addressing issues of alcohol and drug addiction, including addiction to widely-abused substances such as cocaine, heroin, amphetamines, and opiates such as morphine and oxycodone. Studies using nociceptin receptor modulators such as Ro-64-6198 have shown promise in treating alcohol addiction in relevant animal models, although to date no compounds of sufficient selectivity for NOP over opioid receptors and other GPCRs have been identified for advancement to clinical trials. Modulators of the classic opioid receptors, including the μ-opioid receptor (MOP) and the κ-opioid receptor (KOP), have found use in treating numerous malconditions. Certain compounds that modulate NOP also modulate these classic opioid receptors. NOP agonists or antagonists that are largely selective vs. MOP and KOP may have therapeutic advantages over less selective compounds. NOP-selective agonists have been suggested as anxiolytic agents lacking sedative side effects. Such compounds might effectively treat anxiety disorders such as post-traumatic stress syndrome, phobias, and compulsive disorders. Such compounds might also be used in the treatment of other CNS conditions such as cough, sleep disorders, and migraine. NOP-selective antagonists have been suggested for treatment of pain, depression, and neurodegenerative diseases, such as Parkinson's disease.

SUMMARY

The present invention is directed in various embodiments to modulators of a nociceptin receptor, to methods of synthesizing the modulators, and to methods of using the modulators in treatment of various malconditions.

In various embodiments, the invention provides a compound of formula (I)

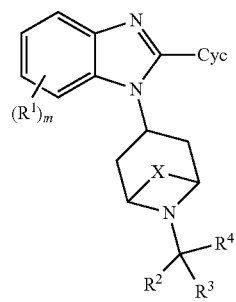

(I)

wherein

X is $(CHR)_n$ wherein n=1, 2, or 3; or X is absent;

$R^1$ is halo, nitro, cyano, (C1-C6)alkyl, (C1-C6)haloalkyl, (C1-C6)alkylsulfonyl, (C1-C6)alkoxy, trifluoromethoxy, or (C1-C6)haloalkylsulfonyl, and m=0, 1, or 2;

$R^2$ and $R^3$ are independently H, (C1-C6)alkyl, (C1-C6)alkyl substituted with 1-5 fluorine atoms, or (C1-C6)cycloalkyl;

$R^4$ is (C1-C10)alkyl, (C3-C10) mono- or bicyclic cycloalkyl, (C3-C10) mono- or bicyclic cycloalkenyl, (C3-C10) mono- or bicyclic cycloalkyl(C1-C6)alkyl, (C3-C10) mono- or bicyclic cycloalkyl(C1-C6)alkenyl, or 3- to 14-membered mono- or bi-cyclic heterocyclyl, wherein any alkyl, cycloalkyl or heterocyclyl is optionally unsaturated, or $R^4$ is (C6-C14)aryl or is (C6-C14)aryl(C1-C6)alkyl, (5- to 14-membered heteroaryl), or (5- to 14-membered heteroaryl)-(C1-C6)alkyl, wherein any alkyl, cycloalkyl, cycloalkenyl, heterocyclyl, aryl or heteroaryl group is substituted with 0-3 J groups, and wherein any alkyl group can further comprise —O—, —N(R)—, —OC(O)N(R)—, —N(R)C(O)N(R)—, or —OC(O)O— therein; or, when X is present, $R^3$ and $R^4$ together with the carbon atom to which they are bonded can form a (C3-C10) mono- or bicyclic cycloalkyl or 3-10-membered mono- or bicyclic heterocyclyl group or a (C6-C14) aryl group, any of which is substituted with 0-3 J; and Cyc is a group of formula (II)

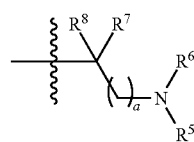

(II)

wherein
a wavy line indicates a point of bonding;
and,
(a) a=0, 1, 2, 3, 4, or 5; and $R^5$, $R^6$, $R^7$ and $R^8$ are each independently H, (C1-C6)alkyl, or (C1-C6)acyl, wherein any alkyl or acyl is substituted with 0-3 J; or,
(b) $R^6$ and $R^7$ together with the atoms to which they are bonded form a heterocyclyl ring such that the group of formula (II) is of formula (IIA)

wherein a=0, 1, or 2, and b=0, 1, or 2; optionally further comprising within the heterocyclyl ring 1-2 additional heteroatom independently selected from O, NR, and $S(O)_q$ wherein q=0, 1, or 2; and wherein the ring is substituted with 0-3 J groups; $R^5$ is H, alkyl, cycloalkyl, acyl, or aroyl; and, $R^8$ is H, alkyl, or cycloalkyl; wherein any non-hydrogen $R^5$ or $R^8$ group is substituted with 0-3 J groups; or, $R^5$ and $R^8$ can together form a (C3-C5)alkylene bridge; and, and, wherein the ring optionally comprises an unsaturation, or is optionally fused with a (C6-C14)aryl substituted with 0-3 J, or both; or,
(c) $R^7$ and $R^8$ together with the atoms to which they are bonded form a ring such that the group of formula (II) is of formula (IIB)

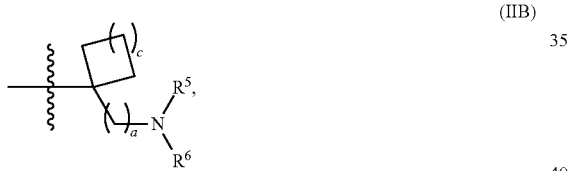

wherein a=0, 1, or 2 and c=0, 1, 2, 3, 4, or 5, and the ring is substituted with 0-3 J groups, optionally further comprising within the ring one heteroatom selected from O, NR, and $S(O)_q$ wherein q=0, 1, or 2; $R^5$ and $R^6$ are each independently H, acyl, or (C1-C6)alkyl, wherein any alkyl is substituted with 0-3 J; or, $R^5$ and $R^6$ together with the nitrogen atom to which they are bonded form a 3-9-membered heterocyclyl ring, substituted with 0-3 J groups, and optionally further comprising within the ring one heteroatom selected from O, NR, and $S(O)_q$ wherein q=0, 1, or 2, and, wherein the ring optionally comprises an unsaturation, or is optionally fused with a (C6-C14)aryl substituted with 0-3 J, or both; and,
J is halo, nitro, cyano, R, $CF_3$, OR, $NR_2$, C(O)OR, $C(O)NR_2$, OC(O)OR, $OC(O)NR_2$, N(R)C(O)OR, N(R)C(O)$NR_2$ or thio/thiono analogs thereof; or two J groups together are methylenedioxy or ethylenedioxy; and,
each independently selected R is H, (C1-C6)alkyl, (C1-C6)acyl, (C6-C14)aryl, (C6-C14)aryl(C1-C6)alkyl, or (C6-C14)aroyl, wherein any non-hydrogen R is substituted with 0-3 $J^R$;
$J^R$ is halo, nitro, cyano, $CF_3$, OR, $NR_2$, C(O)OR, C(O)$NR_2$, OC(O)OR, $OC(O)NR_2$, N(R)C(O)OR, N(R)C(O)$NR_2$ or thio/thiono analogs thereof; or two $J^R$ groups together are methylenedioxy or ethylenedioxy;
or a pharmaceutically acceptable salt thereof.

In various embodiments, the invention provides a pharmaceutical composition comprising a compound of formula (I) and a pharmaceutically acceptable excipient.

In various embodiments, the invention provides a method of modulating a nociceptin receptor, in vivo or in vitro, comprising contacting the receptor with an effective amount or concentration of a compound of formula (I). In various embodiments, an amount or concentration of the compound of formula (I) effective to modulate the nociceptin receptor (NOP) is less than the concentration of the compound necessary or sufficient to modulate the µ-opioid receptor (MOP) or κ-opioid receptor (KOP), providing selective modulation of NOP.

In various embodiments, the invention provides a method of treating a malcondition in a patient, wherein contacting a nociceptin receptor with a compound of formula (I) is medically indicated. For example, the compound can be a nociceptin receptor agonist, antagonist, inverse agonist, or allosteric modulator and the malcondition can comprise an addictive disorder, an anxiety state, cough, sleep disorders, migraine, pain, depression, regulation of food intake and/or energy expenditure, or a neurodegenerative condition such as Parkinson's or Alzheimer's disease. Examples of relevant addictive disorders treated by the invention include, but are not limited to, abuse of alcohol, tobacco, cocaine, amphetamines, heroin, oxycodone, morphine, and related substances. Examples of relevant anxiety states treated by the invention include, but are not limited to, post-traumatic stress disorder, phobias, and compulsive disorders.

DETAILED DESCRIPTION

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) or "patient" means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein a nociceptin receptor (NOP) plays a role in the biochemical mechanisms involved in the disease or malcondition or symptom(s) thereof such that a therapeutically beneficial effect can be achieved by acting on NOP. "Acting on" NOP, or "modulating" NOP, can include binding to NOP and/or inhibiting the bioactivity of NOP as an antagonist and/or allosterically regulating the bioactivity of NOP in vivo and/or acting as an inverse agonist of NOP and/or activating NOP as an agonist, including partial activation and also functionally selective (i.e., functionally biased) activation of NOP, wherein downstream effectors are differentially or selectively activated, an effect also referred to as "pluridimensional efficacy" (see Kenakin, Functional Selectivity and Biased Receptor Signaling, *J. Pharmacol. Exp. Ther.* 2011, 336 (2), 296-302).

The term "MOP" refers to a μ-opioid receptor, and the term "KOP" refers to a κ-opioid receptor, as are well-known in the art.

The expression "effective amount or concentration", when used to describe therapy to an individual suffering from a disorder, refers to the amount of a compound of the invention, or a concentration of the compound within body tissues of the patient, that is effective to inhibit or otherwise modulate NOP in the individual's tissues wherein NOP involved in the disorder is active, wherein such agonism, antagonism, or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure or may not be prepared by the same synthetic methods, without modifications commonly known in the art. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended. In several instances an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, water solubility, water-octanol distribution coefficient such as log P or log D, application properties such as activity against the intended target, and practical properties such as ease of synthesis. Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

When a group is recited, wherein the group can be present in more than a single orientation within a structure resulting in more than single molecular structure, e.g., a carboxamide group C(=O)NR, it is understood that the group can be present in any possible orientation, e.g., X—C(=O)N (R)—Y or X—N(R)C(=O)—Y, unless the context clearly limits the orientation of the group within the molecular structure.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

The term "amino protecting group" or "N-protected" as used herein refers to those groups intended to protect an amino group against undesirable reactions during synthetic procedures, groups which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, diphenylmethyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, diphenylmethyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

In various embodiments, J can be halo, nitro, cyano, CF$_3$, OR, NR$_2$, or R, or is C(O)OR, C(O)NR$_2$, OC(O)OR, OC(O)NR$_2$, N(R)C(O)OR, N(R)C(O)NR$_2$ or thio/thiono analogs thereof. By "thio/thiono analogs thereof", with respect to a group containing an O, is meant that any or all O atoms in the group can be replaced by an S atom; e.g., for group C(O)OR, a "thio/thiono analog thereof" includes C(S)OR, C(O)SR, and C(S)SR; e.g., for group OC(O)NR$_2$, a "thio/thiono analog thereof" includes SC(O)NR$_2$, OC(S)NR$_2$, and SC(S)NR$_2$; and so forth.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as $(CH_2)_n$ or $(CR'_2)_n$ wherein n is 1, 2, 3, or more, and each R' is independently selected.

C(O) and $S(O)_2$ groups can also be bound to one or two heteroatoms, such as nitrogen or oxygen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a "urea." When a C(O) is bonded to one oxygen and one nitrogen atom, the resulting group is termed a "carbamate" or "urethane." When a $S(O)_2$ group is bound to one carbon and one nitrogen atom, the resulting unit is termed a "sulfonamide." When a $S(O)_2$ group is bound to two nitrogen atoms, the resulting unit is termed a "sulfamide."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. As used herein, the term "alkyl" encompasses n-alkyl, isoalkyl, and anteiso alkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, heteroaryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to primary carboxamide groups (—C(O)NH$_2$) and formamide groups (—NHC(O)H). A "carboxamido" group is a group of the formula C(O)NR$_2$, wherein R can be H, alkyl, aryl, etc.

The term "azido" refers to an N$_3$ group. An "azide" can be an organic azide or can be a salt of the azide (N$_3^-$) anion. The term "nitro" refers to an NO$_2$ group bonded to an organic moiety. The term "nitroso" refers to an NO group bonded to an organic moiety. The term nitrate refers to an ONO$_2$ group bonded to an organic moiety or to a salt of the nitrate (NO$_3^-$) anion.

The term "urethane" ("carbamoyl" or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

A "salt" as is well known in the art includes an organic compound such as a carboxylic acid, a sulfonic acid, or an amine, in ionic form, in combination with a counter ion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention. Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds of the Invention

Tautomerism

Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein.

Optical Isomerism

It will be understood that when compounds of the present invention contain one or more chiral centers, the compounds may exist in, and may be isolated as single and substantially pure enantiomeric or diastereomeric forms, as diastereomeric mixtures, or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

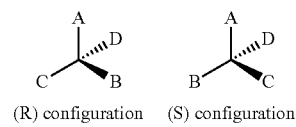

(R) configuration   (S) configuration

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Another well-known method of obtaining separate and substantially pure optical isomers is classic resolution, whereby a chiral racemic compound containing an ionized functional group, such as a protonated amine or carboxylate group, forms diastereomeric salts with an oppositely ionized chiral nonracemic additive. The resultant diastereomeric salt forms can then be separated by standard physical means, such as differential solubility, and then the chiral nonracemic additive may be either removed or exchanged with an alternate counter ion by standard chemical means, or alternatively the diastereomeric salt form may retained as a salt to be used as a therapeutic agent or as a precursor to a therapeutic agent.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of formula (I) which are biologically active in the treatment of diseases and malconditions.

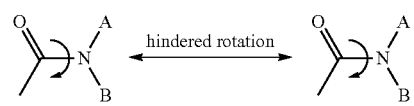

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below, wherein an asterisk denotes the point of attachment of the aryl group within the compound of the invention.

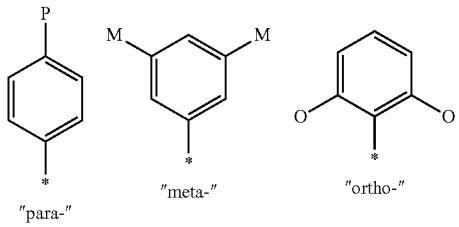

In various embodiments, the compound or set of compounds, such as are among the inventive compounds or are used in the inventive methods, can be any one of any of the combinations and/or sub-combinations of the above-listed embodiments.

DETAILED DESCRIPTION

The present invention is directed to compounds designed as modulators of a nociceptin receptor (NOP), to methods of synthesizing the compounds, and to methods of using the compounds in modulation of NOP. For instance, NOP can be modulated in patients suffering from a malcondition for which modulation, agonism or antagonism of NOP is medically indicated. Nociceptin modulators can be, e.g., effective anxiolytic compounds that do not possess opioid side effects. Various compounds of the invention do not act to an appreciable extent on the μ-opioid receptor (MOP) at a dose effective for modulation of NOP. One exemplary compound, 11 (see Table 1, below), with an $EC_{50}$ versus NOP of 2.6 nM has exhibited a greater than 40-fold selectivity for NOP modulation over MOP modulation (MOP $EC_{50}$=118 nM). MOP is a prime site for the action of morphine and heroin, which cause analgesia and other pharmacological effects. Compound 11 also has favorable pharmacokinetic properties, including high blood-brain barrier penetration (44%), stability in human liver microsomes (2.5 hrs), and low affinity for selected cytochrome $P_{450}$ enzymes. The compound has been found to exhibit significant anxiolytic effects in rats without noticeable sedation. Other compounds of the invention, such as 12 and 19, show even greater NOP/MOP selectivity.

Accordingly, in various embodiments, the invention provides a compound of formula (I)

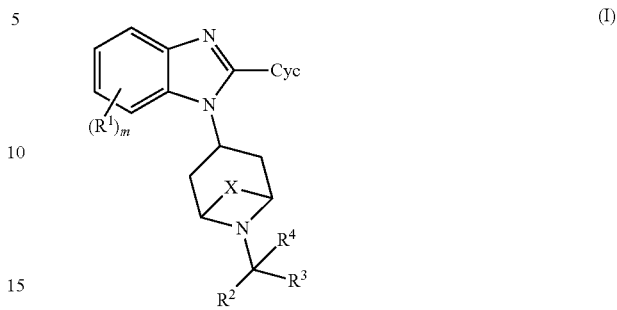

wherein
X is $(CHR)_n$ wherein n=1, 2, or 3; or X is absent;
$R^1$ is halo, nitro, cyano, (C1-C6)alkyl, (C1-C6)haloalkyl, (C1-C6)alkylsulfonyl, (C1-C6)alkoxy, trifluoromethoxy, or (C1-C6)haloalkylsulfonyl, and m=0, 1, or 2;
$R^2$ and $R^3$ are independently H, (C1-C6)alkyl, (C1-C6)alkyl substituted with 1-5 fluorine atoms, or (C1-C6)cycloalkyl;
$R^4$ is (C1-C10)alkyl, (C3-C10) mono- or bicyclic cycloalkyl, (C3-C10) mono- or bicyclic cycloalkenyl, (C3-C10) mono- or bicyclic cycloalkyl(C1-C6)alkyl, (C3-C10) mono- or bicyclic cycloalkyl(C1-C6)alkenyl, or 3- to 14-membered mono- or bi-cyclic heterocyclyl, wherein any alkyl, cycloalkyl or heterocyclyl is optionally unsaturated, or $R^4$ is (C6-C14)aryl or is (C6-C14)aryl(C1-C6)alkyl, (5- to 14-membered heteroaryl), or (5- to 14-membered heteroaryl)-(C1-C6)alkyl, wherein any alkyl, cycloalkyl, cycloalkenyl, heterocyclyl, aryl or heteroaryl group is substituted with 0-3 J groups, and wherein any alkyl group can further comprise —O—, —N(R)—, —OC(O)N(R)—, —N(R)C(O)N(R)—, or —OC(O)O— therein; or,
when X is present, $R^3$ and $R^4$ together with the carbon atom to which they are bonded can form a (C3-C10) mono- or bicyclic cycloalkyl or 3-10-membered mono- or bicyclic heterocyclyl group or a (C6-C14) aryl group, any of which is substituted with 0-3 J; and
Cyc is a group of formula (II)

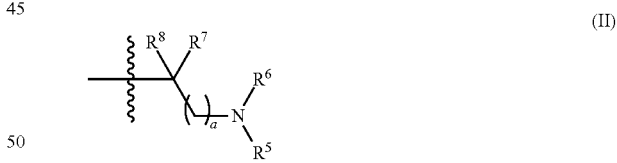

wherein
a wavy line indicates a point of bonding;
and,
(a) a=0, 1, 2, 3, 4, or 5; and $R^5$, $R^6$, $R^7$ and $R^8$ are each independently H, (C1-C6)alkyl, or (C1-C6)acyl, wherein any alkyl or acyl is substituted with 0-3 J; or,
(b) $R^6$ and $R^7$ together with the atoms to which they are bonded form a heterocyclyl ring such that the group of formula (II) is of formula (IIA)

wherein a=0, 1, or 2, and b=0, 1, or 2; optionally further comprising within the heterocyclyl ring 1-2 additional heteroatom independently selected from O, NR, and S(O)$_q$ wherein q=0, 1, or 2; and wherein the ring is substituted with 0-3 J groups; $R^5$ is H, alkyl, cycloalkyl, acyl, or aroyl; and, $R^8$ is H, alkyl, or cycloalkyl; wherein any non-hydrogen $R^5$ or $R^8$ group is substituted with 0-3 J groups; or, $R^5$ and $R^8$ can together form a (C3-C5)alkylene bridge; and, and, wherein the ring optionally comprises an unsaturation, or is optionally fused with a (C6-C14)aryl substituted with 0-3 J, or both; or, (c) $R^7$ and $R^8$ together with the atoms to which they are bonded form a ring such that the group of formula (II) is of formula (IIB)

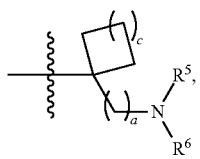

(IIB)

wherein a=0, 1, or 2 and c=0, 1, 2, 3, 4, or 5, and the ring is substituted with 0-3 J groups, optionally further comprising within the ring one heteroatom selected from O, NR, and S(O)$_q$ wherein q=0, 1, or 2; $R^5$ and $R^6$ are each independently H, acyl, or (C1-C6)alkyl, wherein any alkyl is substituted with 0-3 J; or, $R^5$ and $R^6$ together with the nitrogen atom to which they are bonded form a 3-9-membered heterocyclyl ring, substituted with 0-3 J groups, and optionally further comprising within the ring one heteroatom selected from O, NR, and S(O)$_q$ wherein q=0, 1, or 2, and, wherein the ring optionally comprises an unsaturation, or is optionally fused with a (C6-C14)aryl substituted with 0-3 J, or both; and, J is halo, nitro, cyano, R, CF$_3$, OR, NR$_2$, C(O)OR, C(O)NR$_2$, OC(O)OR, OC(O)NR$_2$, N(R)C(O)OR, N(R)C(O)NR$_2$ or thio/thiono analogs thereof; or two J groups together are methylenedioxy or ethylenedioxy; and, each independently selected R is H, (C1-C6)alkyl, (C1-C6)acyl, (C6-C14)aryl, (C6-C14)aryl(C1-C6)alkyl, or (C6-C14)aroyl, wherein any non-hydrogen R is substituted with 0-3 $J^R$;

$J^R$ is halo, nitro, cyano, CF$_3$, OR, NR$_2$, C(O)OR, C(O)NR$_2$, OC(O)OR, OC(O)NR$_2$, N(R)C(O)OR, N(R)C(O)NR$_2$ or thio/thiono analogs thereof; or two $J^R$ groups together are methylenedioxy or ethylenedioxy;

or a pharmaceutically acceptable salt thereof.

More specifically, in various embodiments, the invention provides a compound of formula (I) wherein $R^1$ is fluoro, chloro, methyl, CF$_3$, methylsulfonyl, or trifluoromethylsulfonyl.

In various embodiments, the invention provides a compound of formula (I) wherein $R^2$ and $R^3$ independently are H or methyl, wherein $R^4$ is cyclohexyl, cycloheptyl, cyclooctyl, n-heptan-3-yl, 2,6,6,-trimethylcyclohex-1-enyl, 6,6-dimethylbicyclo[3.1.1]hept-2-yl, bicyclo[2.2.1]hept-2-en-5-yl, piperidin-4-yl, tetrahydropyran-4-yl, or phenyl.

In various embodiments, the invention provides a compound of formula (I) with subgroup (II) wherein $R^5$ and $R^6$ are H, acetyl, or methyl.

In various embodiments, the invention provides a compound of formula (I) wherein Cyc is aminoethyl, aminopropyl, aminobutyl, azetidin-3-yl, pyrrolidin-2-yl, 4-hydroxypyrrolidin-4-yl, pyrrolidin-3-yl, N-methylpyrrolidin-3-yl, N-acetylpyrrolidin-3-yl, piperidin-3-yl, piperidin-4-yl, 1,3-thiazolidin-4-yl, aminocyclopropyl, aminocyclopentyl, aminocyclohexyl, 3-amino-1,2,5-oxadiazol-4-yl, indol-3-yl, or 5-fluoroindol-2-yl.

In various embodiments, the invention provides a compound of formula (I) wherein for the group of formula (II) $R^5$, $R^6$, $R^7$ and $R^8$ are each H.

In various embodiments, the invention provides a compound of formula (I) wherein the group of formula (II) is of formula (IIA).

In various embodiments, the invention provides a compound of formula (I) wherein the group of formula (II) is of formula (IIB).

In various embodiments, the invention provides a compound of formula (I) with subgroup (II) wherein $R^7$ and $R^8$ are H, methyl, or taken together with the atom to which they are attached form a 3-, 4-, 5-, or 6-membered alkylidine ring as depicted in subgroup (IIb), wherein $R^5$ and $R^8$ are independently H, Me, or acyl.

In various embodiments, the invention provides a compound of formula (I) with subgroup (II) wherein $R^6$ and $R^7$ together with which the atoms they are attached form a ring as depicted in subgroup (IIA), wherein $R^5$ is H, Me, or acyl and $R^8$ is H or Me.

In various embodiments, invention provides a compound of formula (I) in which X is present and equals CH$_2$ or CH$_2$CH$_2$ (thus n=1 or 2, and R=H); wherein $R^2$=H or Me, $R^3$=H, and $R^4$=cyclohexyl, cycloheptyl, cyclooctyl, n-heptan-3-yl, 2,6,6,-trimethylcyclohex-1-enyl, 6,6-dimethylbicyclo[3.1.1]hept-2-yl, bicyclo[2.2.1]hept-2-en-5-yl, piperidin-4-yl, tetrahydropyran-4-yl, or phenyl.

In various embodiments, invention provides a compound of formula (I) in which X is present and equals CH$_2$ or CH$_2$CH$_2$ (thus n=1 or 2, and R=H); wherein $R^2$=H, $R^3$ and $R^4$ taken together=cyclopentyl, cyclohexyl, cycloheptyl, cyclooctyl, n-heptan-3-yl, 2,6,6,-trimethylcyclohex-1-enyl, 6,6-dimethylbicyclo[3.1.1]hept-2-yl, bicyclo[2.2.1]hept-2-en-5-yl, piperidin-4-yl, tetrahydropyran-4-yl, phenyl, 3-indolyl, 5-benzimidazolyl, 6-indazolyl, 3-quinolyl, 2-naphthyl, 2-benzothiazolyl, 2-pyridyl, 3-pyridyl, 4-pyridyl, and members of these aryl and heteroaryl groups being one or more halogen, alkyl, haloalkyl, or alkoxy substitutents.

In various embodiments, the compound of formula (I) is any of the compounds shown in Table 1, below, or a pharmaceutically acceptable salt thereof.

TABLE 1

Specifically Claimed Compounds

| # | Structure | Substituents |
|---|---|---|
| 1 | 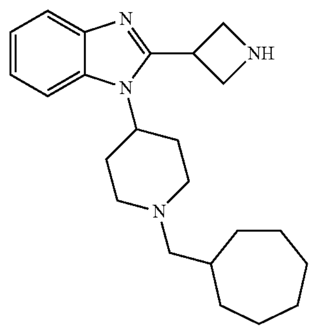 [SMILES: c1ccc2c(c1)nc(C1CNC1)n2C1CCN(CC2CCCCCC2)CC1] | $R^1$ = absent,<br>X = absent,<br>$R^2$ = H,<br>$R^3$ = H,<br>$R^4$ = cycloheptyl,<br>Cyc = azetidin-3-yl |
| 2 | 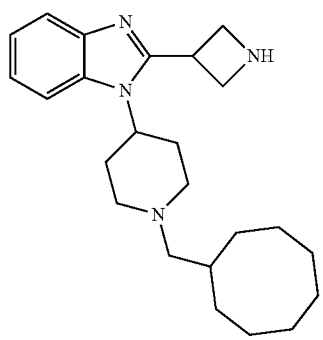 [SMILES: c1ccc2c(c1)nc(C1CNC1)n2C1CCN(CC2CCCCCCC2)CC1] | $R^1$ = absent,<br>X = absent,<br>$R^2$ = H,<br>$R^3$ = H,<br>$R^4$ = cyclooctyl,<br>Cyc = azetidin-3-yl |
| 3 | 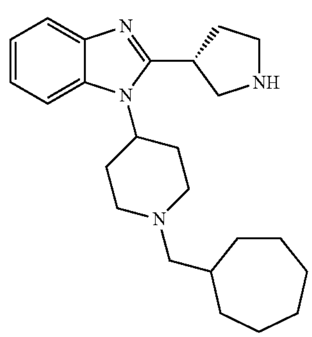 [SMILES: c1ccc2c(c1)nc([C@@H]1CCNC1)n2C1CCN(CC2CCCCCC2)CC1] | $R^1$ = absent,<br>X = absent,<br>$R^2$ = H,<br>$R^3$ = H,<br>$R^4$ = cycloheptyl,<br>Cyc = pyrrolidin-3-yl ((R)-isomer is drawn*) |
| 4 | 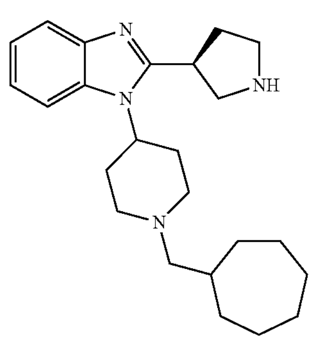 [SMILES: c1ccc2c(c1)nc([C@H]1CCNC1)n2C1CCN(CC2CCCCCC2)CC1] | $R^1$ = absent,<br>X = absent,<br>$R^2$ = H,<br>$R^3$ = H,<br>$R^4$ = cycloheptyl,<br>Cyc = pyrrolidin-3-yl ((S)-isomer is drawn*) |

TABLE 1-continued

Specifically Claimed Compounds

| # | Structure | Substituents |
|---|-----------|--------------|
| 5 | 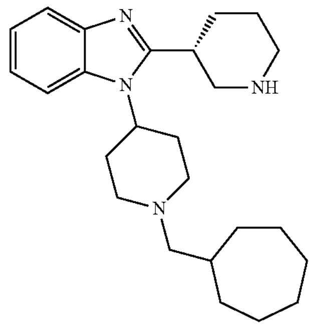 [SMILES: c1ccc2c(c1)nc([C@@H]1CCCNC1)n2C1CCN(CC2CCCCCC2)CC1] | $R^1$ = absent,<br>X = absent,<br>$R^2$ = H,<br>$R^3$ = H,<br>$R^4$ = cycloheptyl,<br>Cyc = piperidin-3-yl ((R)-isomer is drawn*) |
| 6 | 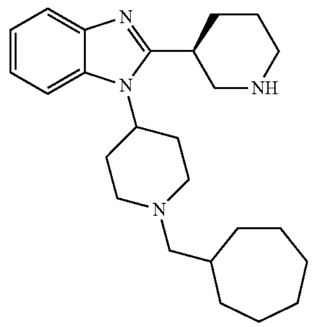 [SMILES: c1ccc2c(c1)nc([C@H]1CCCNC1)n2C1CCN(CC2CCCCCC2)CC1] | $R^1$ = absent,<br>X = absent,<br>$R^2$ = H,<br>$R^3$ = H,<br>$R^4$ = cycloheptyl,<br>Cyc = piperidin-3-yl ((S)-isomer is drawn*) |
| 7 | 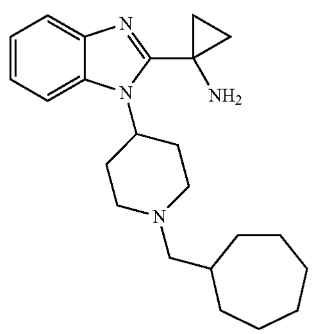 [SMILES: NC1(c2nc3ccccc3n2C2CCN(CC3CCCCCC3)CC2)CC1] | $R^1$ = absent,<br>X = absent,<br>$R^2$ = H,<br>$R^3$ = H,<br>$R^4$ = cycloheptyl,<br>Cyc = 1-aminocyclopropyl |
| 8 | 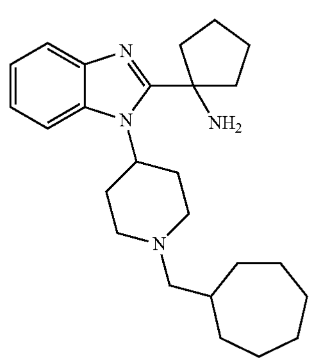 [SMILES: NC1(c2nc3ccccc3n2C2CCN(CC3CCCCCC3)CC2)CCCC1] | $R^1$ = absent,<br>X = absent,<br>$R^2$ = H,<br>$R^3$ = H,<br>$R^4$ = cycloheptyl,<br>Cyc = 1-aminocyclopentyl |

TABLE 1-continued

Specifically Claimed Compounds

| # | Structure | Substituents |
|---|---|---|
| 9 | 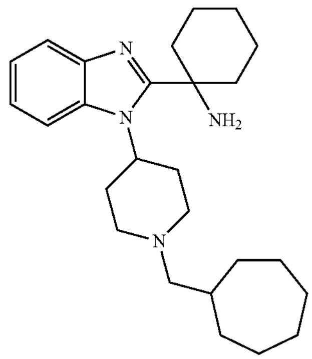 [SMILES: NC1(c2nc3ccccc3n2C2CCN(CC3CCCCCC3)CC2)CCCCC1] | R¹ = absent, X = absent, R² = H, R³ = H, R⁴ = cycloheptyl, Cyc = 1-aminocyclohexyl |
| 10 | 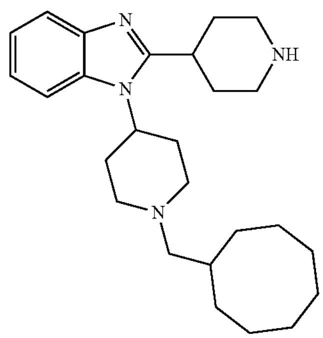 [SMILES: c1ccc2c(c1)nc(C1CCNCC1)n2C1CCN(CC2CCCCCCC2)CC1] | R¹ = absent, X = absent, R² = H, R³ = H, R⁴ = cyclooctyl, Cyc = piperidin-4-yl |
| 11 | 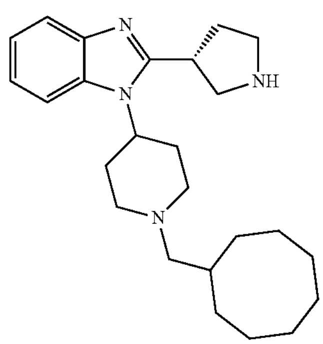 [SMILES: c1ccc2c(c1)nc([C@@H]1CCNC1)n2C1CCN(CC2CCCCCCC2)CC1] | R¹ = absent, X = absent, R² = H, R³ = H, R⁴ = cyclooctyl, Cyc = pyrrolidin-3-yl ((R)-isomer is drawn*) |
| 12 | 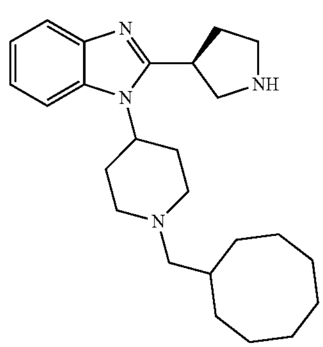 [SMILES: c1ccc2c(c1)nc([C@H]1CCNC1)n2C1CCN(CC2CCCCCCC2)CC1] | R¹ = absent, X = absent, R² = H, R³ = H, R⁴ = cyclooctyl, Cyc = pyrrolidin-3-yl ((S)-isomer is drawn*) |

TABLE 1-continued

Specifically Claimed Compounds

| # | Structure | Substituents |
|---|-----------|--------------|
| 13 | 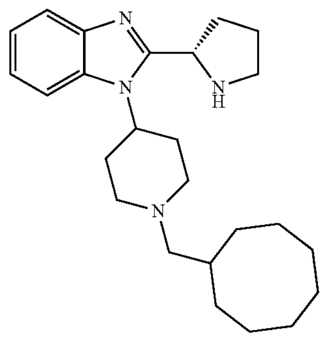 [SMILES: c1ccc2c(c1)nc([C@@H]1CCCN1)n2C1CCN(CC2CCCCCCC2)CC1] | $R^1$ = absent,<br>X = absent,<br>$R^2$ = H,<br>$R^3$ = H,<br>$R^4$ = cyclooctyl,<br>Cyc = pyrrolidin-2-yl ((S)-isomer is drawn*) |
| 14 | 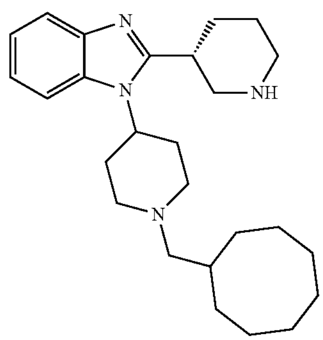 [SMILES: c1ccc2c(c1)nc([C@@H]1CCCNC1)n2C1CCN(CC2CCCCCCC2)CC1] | $R^1$ = absent,<br>X = absent,<br>$R^2$ = H,<br>$R^3$ = H,<br>$R^4$ = cyclooctyl,<br>Cyc = piperidin-3-yl ((R)-isomer is drawn*) |
| 15 | 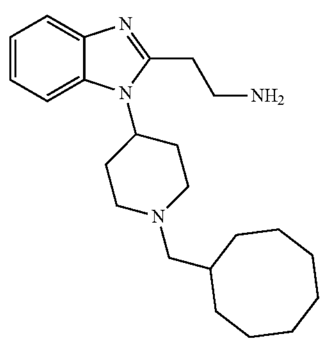 [SMILES: NCCc1nc2ccccc2n1C1CCN(CC2CCCCCCC2)CC1] | $R^1$ = absent,<br>X = absent,<br>$R^2$ = H,<br>$R^3$ = H,<br>$R^4$ = cyclooctyl<br>Cyc = 2-aminoethyl |
| 16 | 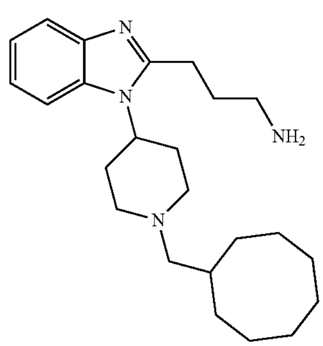 [SMILES: NCCCc1nc2ccccc2n1C1CCN(CC2CCCCCCC2)CC1] | $R^1$ = absent,<br>X = absent,<br>$R^2$ = H,<br>$R^3$ = H,<br>$R^4$ = cyclooctyl,<br>Cyc = 3-aminopropyl |

TABLE 1-continued

Specifically Claimed Compounds

| # | Structure | Substituents |
|---|-----------|--------------|
| 17 | 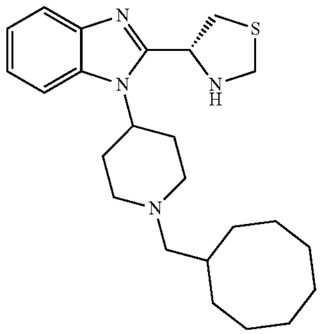 [SMILES: c1ccc2c(c1)nc([C@@H]1CSCN1)n2C1CCN(CC2CCCCCCC2)CC1] | $R^1$ = absent,<br>X = absent,<br>$R^2$ = H,<br>$R^3$ = H,<br>$R^4$ = cyclooctyl,<br>Cyc = thiazolidin-4-yl ((R)-isomer is drawn*) |
| 18 | 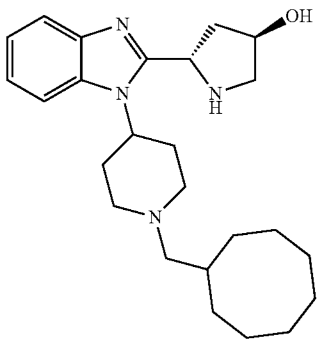 [SMILES: O[C@H]1CN[C@H](c2nc3ccccc3n2C2CCN(CC3CCCCCCC3)CC2)C1] | $R^1$ = absent,<br>X = absent,<br>$R^2$ = H,<br>$R^3$ = H,<br>$R^4$ = cyclooctyl,<br>Cyc = 3-hydroxypyrrolidin-4-yl ((3R,5S)-isomer is drawn*) |
| 19 | 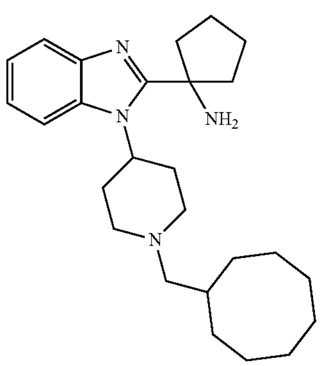 [SMILES: NC1(c2nc3ccccc3n2C2CCN(CC3CCCCCCC3)CC2)CCCC1] | $R^1$ = absent,<br>X = absent,<br>$R^2$ = H,<br>$R^3$ = H,<br>$R^4$ = cyclooctyl,<br>Cyc = 1-aminocyclopentyl |
| 20 | 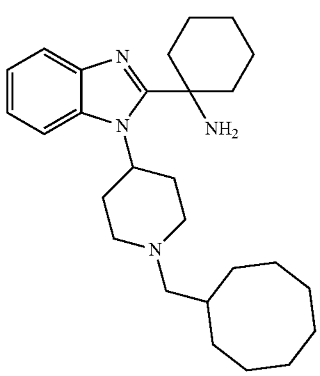 [SMILES: NC1(c2nc3ccccc3n2C2CCN(CC3CCCCCCC3)CC2)CCCCC1] | $R^1$ = absent,<br>X = absent,<br>$R^2$ = H,<br>$R^3$ = H,<br>$R^4$ = cyclooctyl,<br>Cyc = 1-aminocyclohexyl |

TABLE 1-continued

Specifically Claimed Compounds

| # | Structure | Substituents |
|---|---|---|
| 21 | 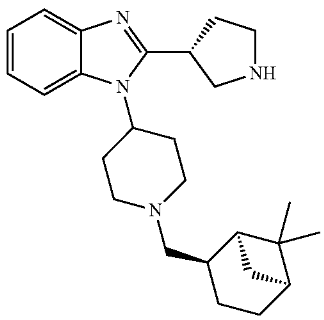 [SMILES: CC1(C)[C@H]2CC[C@@H](CN3CCC(n4c([C@@H]5CCNC5)nc5ccccc54)CC3)[C@@H]1C2] | R¹ = absent,<br>X = absent,<br>R² = H,<br>R³ = H,<br>R⁴ = 6,6-dimethylbicyclo[3.1.1]-hept-2-yl,<br>Cyc = pyrrolidin-3-yl ((R)-isomer is drawn*) |
| 22 | 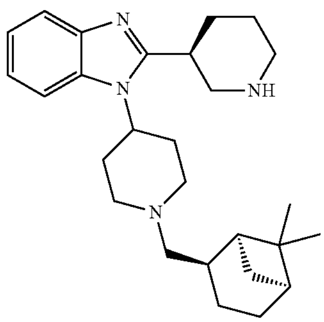 [SMILES: CC1(C)[C@H]2CC[C@@H](CN3CCC(n4c([C@H]5CCCNC5)nc5ccccc54)CC3)[C@@H]1C2] | R¹ = absent,<br>X = absent,<br>R² = H,<br>R³ = H,<br>R⁴ = 6,6-dimethylbicyclo[3.1.1]-hept-2-yl,<br>Cyc = piperidin-3-yl ((S)-isomer is drawn*) |
| 23 | 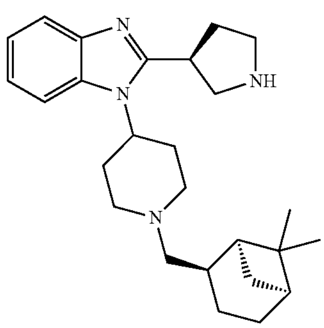 [SMILES: CC1(C)[C@H]2CC[C@@H](CN3CCC(n4c([C@H]5CCNC5)nc5ccccc54)CC3)[C@@H]1C2] | R¹ = absent,<br>X = absent,<br>R² = H,<br>R³ = H,<br>R⁴ = 6,6-dimethylbicyclo[3.1.1]-hept-2-yl,<br>Cyc = pyrrolidin-3-yl ((S)-isomer is drawn*) |
| 24 | 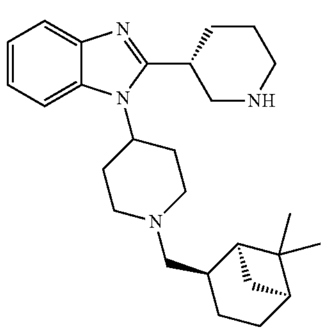 [SMILES: CC1(C)[C@H]2CC[C@@H](CN3CCC(n4c([C@@H]5CCCNC5)nc5ccccc54)CC3)[C@@H]1C2] | R¹ = absent,<br>X = absent,<br>R² = H,<br>R³ = H,<br>R⁴ = 6,6-dimethylbicyclo[3.1.1]-hept-2-yl,<br>Cyc = piperidin-3-yl ((R)-isomer is drawn*) |

TABLE 1-continued

Specifically Claimed Compounds

| # | Structure | Substituents |
|---|-----------|--------------|
| 25 | 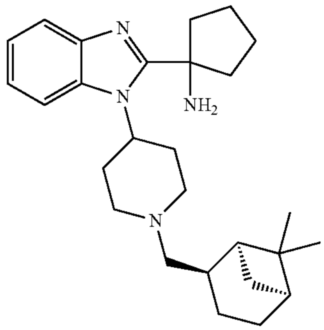 [SMILES: CC1(C)[C@H]2CC[C@@H](CN3CCC(n4c(C5(N)CCCC5)nc5ccccc54)CC3)[C@@H]1C2] | $R^1$ = absent,<br>X = absent,<br>$R^2$ = H, $R^3$ = H,<br>$R^4$ = 6,6-dimethylbicyclo[3.1.1]-hept-2-yl,<br>Cyc = 1-aminocyclopentyl |
| 26 | 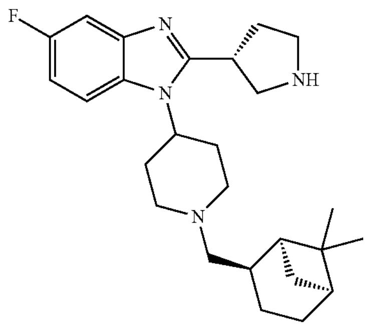 [SMILES: CC1(C)[C@H]2CC[C@@H](CN3CCC(n4c([C@@H]5CCNC5)nc5cc(F)ccc54)CC3)[C@@H]1C2] | $R^1$ = fluoro, m = 1,<br>X = absent,<br>$R^2$ = H,<br>$R^3$ = H,<br>$R^4$ = 6,6-dimethylbicyclo[3.1.1]-hept-2-yl,<br>Cyc = pyrrolidin-3-yl ((R)-isomer is drawn*) |
| 27 | 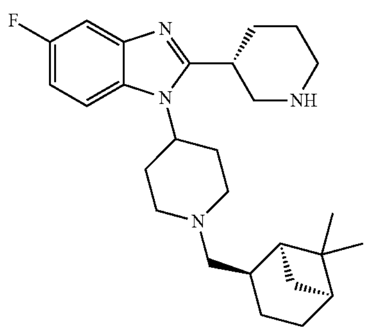 [SMILES: CC1(C)[C@H]2CC[C@@H](CN3CCC(n4c([C@@H]5CCCNC5)nc5cc(F)ccc54)CC3)[C@@H]1C2] | $R^1$ = fluoro, m = 1,<br>X = absent,<br>$R^2$ = H,<br>$R^3$ = H,<br>$R^4$ = 6,6-dimethylbicyclo[3.1.1]-hept-2-yl,<br>Cyc = piperidin-3-yl ((R)-isomer is drawn*) |
| 28 | 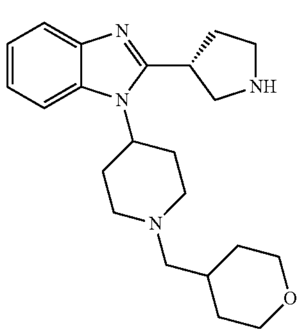 [SMILES: c1ccc2c(c1)nc([C@@H]1CCNC1)n2C1CCN(CC2CCOCC2)CC1] | $R^1$ = absent,<br>X = absent,<br>$R^2$ = H,<br>$R^3$ = H,<br>$R^4$ = tetrahydropyran-4-yl,<br>Cyc = pyrrolidin-3-yl ((R)-isomer is drawn*) |

TABLE 1-continued

Specifically Claimed Compounds

| # | Structure | Substituents |
|---|---|---|
| 29 | 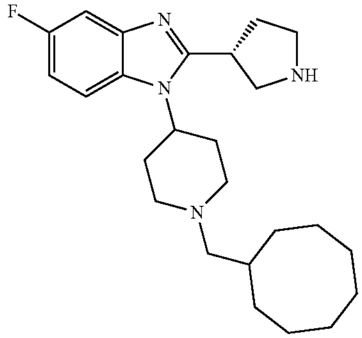 [SMILES: Fc1ccc2c(c1)nc([C@@H]1CCNC1)n2C1CCN(CC2CCCCCCC2)CC1] | $R^1$ = fluoro, m = 1,<br>X = absent,<br>$R^2$ = H,<br>$R^3$ = H,<br>$R^4$ = cyclooctyl,<br>Cyc = pyrrolidin-3-yl ((R)-isomer is drawn*) |
| 30 | 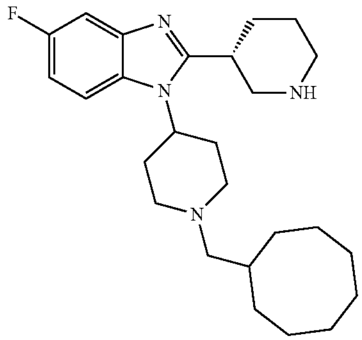 [SMILES: Fc1ccc2c(c1)nc([C@@H]1CCCNC1)n2C1CCN(CC2CCCCCCC2)CC1] | $R^1$ = fluoro, m = 1,<br>X = absent,<br>$R^2$ = H,<br>$R^3$ = H,<br>$R^4$ = cyclooctyl,<br>Cyc = piperidin-3-yl ((R)-isomer is drawn*) |
| 31 | 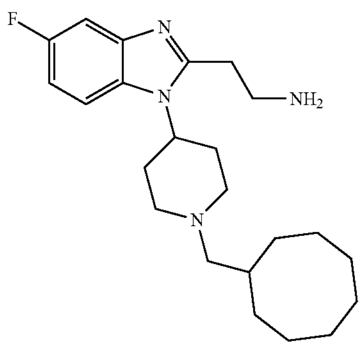 [SMILES: NCCc1nc2cc(F)ccc2n1C1CCN(CC2CCCCCCC2)CC1] | $R^1$ = fluoro, m = 1,<br>X = absent,<br>$R^2$ = H,<br>$R^3$ = H,<br>$R^4$ = cyclooctyl,<br>Cyc = 2-aminoethyl |
| 32 | 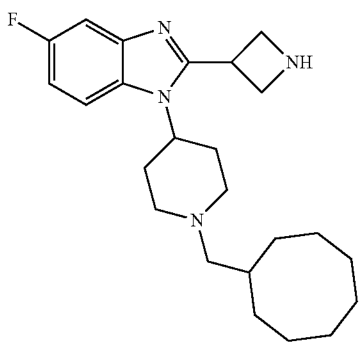 [SMILES: Fc1ccc2c(c1)nc(C1CNC1)n2C1CCN(CC2CCCCCCC2)CC1] | $R^1$ = 5-fluoro, m = 1,<br>X = absent,<br>$R^2$ = H,<br>$R^3$ = H,<br>$R^4$ = cyclooctyl,<br>Cyc = azetidin-3-yl |

TABLE 1-continued

Specifically Claimed Compounds

| # | Structure | Substituents |
|---|-----------|--------------|
| 33 | 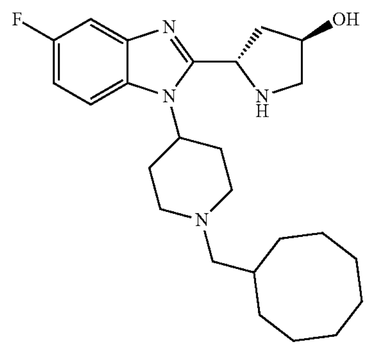 [SMILES: O[C@H]1CN[C@H](c2nc3cc(F)ccc3n2C2CCN(CC3CCCCCCC3)CC2)C1] | $R^1$ = fluoro, m = 1, X = absent, $R^2$ = H, $R^3$ = H, $R^4$ = cyclooctyl, Cyc = 3-hydroxypyrrolidin-5-yl ((3R,5S)-isomer is drawn*) |
| 34 | 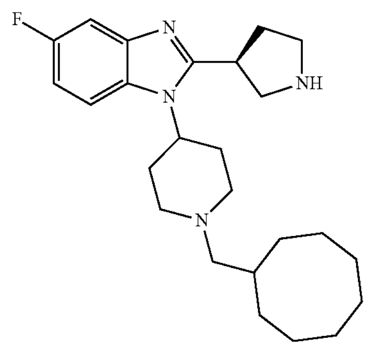 [SMILES: Fc1ccc2c(c1)nc([C@H]1CCNC1)n2C1CCN(CC2CCCCCCC2)CC1] | $R^1$ = fluoro, m = 1, X = absent, $R^2$ = H, $R^3$ = H, $R^4$ = cyclooctyl, Cyc = pyrrolidin-3-yl ((S)-isomer is drawn*) |
| 35 | 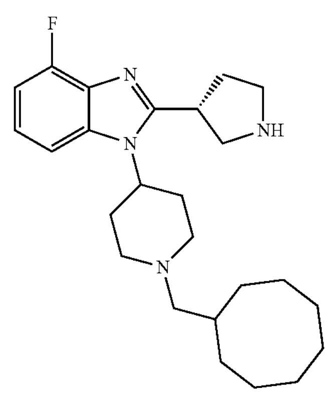 [SMILES: Fc1cccc2c1nc([C@@H]1CCNC1)n2C1CCN(CC2CCCCCCC2)CC1] | $R^1$ = fluoro, m = 1, X = absent, $R^2$ = H, $R^3$ = H, $R^4$ = cyclooctyl, Cyc = pyrrolidin-3-yl ((R)-isomer is drawn*) |
| 36 | 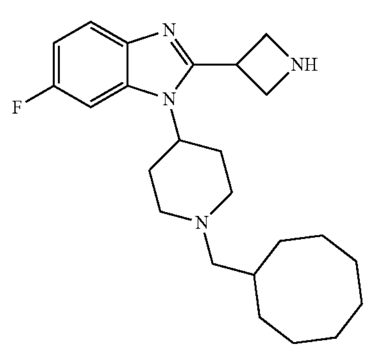 [SMILES: Fc1ccc2nc(C3CNC3)n(C3CCN(CC4CCCCCCC4)CC3)c2c1] | $R^1$ = fluoro, m = 1, X = absent, $R^2$ = H, $R^3$ = H, $R^4$ = cyclooctyl, Cyc = azetidin-3-yl |

TABLE 1-continued

Specifically Claimed Compounds

| # | Structure | Substituents |
|---|-----------|--------------|
| 37 | 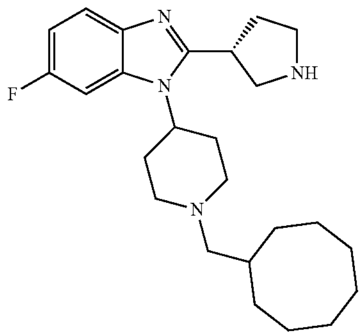 [SMILES: Fc1ccc2nc([C@@H]3CCNC3)n(C3CCN(CC4CCCCCCC4)CC3)c2c1] | R¹ = fluoro, m = 1,<br>X = absent,<br>R² = H,<br>R³ = H,<br>R⁴ = cyclooctyl,<br>Cyc = pyrrolidin-3-yl ((R)-isomer is drawn*) |
| 38 | 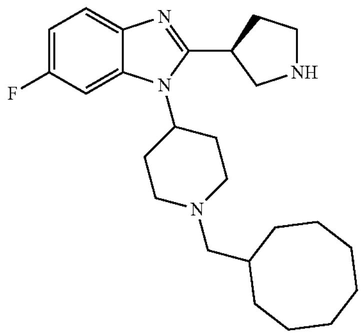 [SMILES: Fc1ccc2nc([C@H]3CCNC3)n(C3CCN(CC4CCCCCCC4)CC3)c2c1] | R¹ = fluoro, m = 1,<br>X = absent,<br>R² = H,<br>R³ = H,<br>R⁴ = cyclooctyl,<br>Cyc = pyrrolidin-3-yl ((S)-isomer is drawn*) |
| 39 | 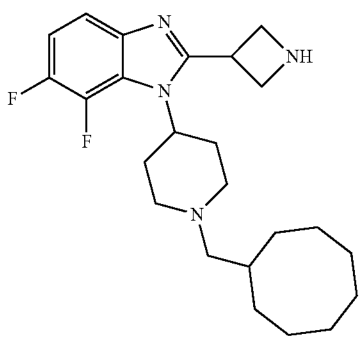 [SMILES: Fc1ccc2nc(C3CNC3)n(C3CCN(CC4CCCCCCC4)CC3)c2c1F] | R¹ = fluoro, m = 2,<br>X = absent,<br>R² = H,<br>R³ = H,<br>R⁴ = cyclooctyl,<br>Cyc = azetidin-3-yl |
| 40 | 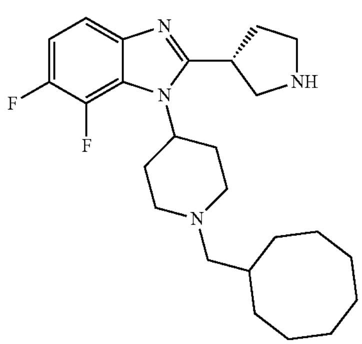 [SMILES: Fc1ccc2nc([C@@H]3CCNC3)n(C3CCN(CC4CCCCCCC4)CC3)c2c1F] | R¹ = fluoro, m = 2,<br>X = absent,<br>R² = H,<br>R³ = H,<br>R⁴ = cyclooctyl,<br>Cyc = pyrrolidin-3-yl ((R)-isomer is drawn*) |

TABLE 1-continued

Specifically Claimed Compounds

| # | Structure | Substituents |
|---|---|---|
| 41 | 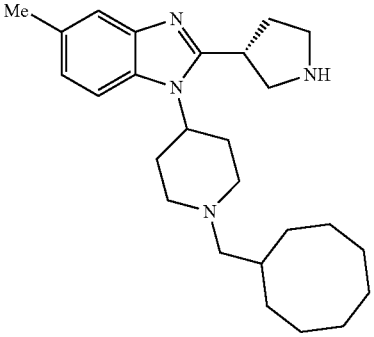 [SMILES: Cc1ccc2c(c1)nc([C@@H]1CCNC1)n2C1CCN(CC2CCCCCCC2)CC1] | R¹ = methyl, m = 1,<br>X = absent,<br>R² = H,<br>R³ = H,<br>R⁴ = cyclooctyl,<br>Cyc = pyrrolidin-3-yl ((R)-isomer is drawn*) |
| 42 | 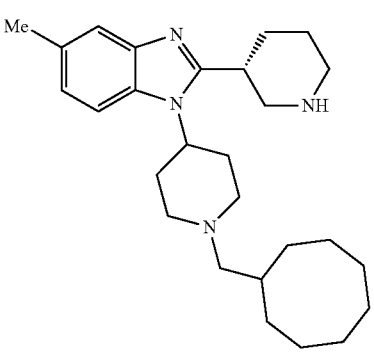 [SMILES: Cc1ccc2c(c1)nc([C@@H]1CCCNC1)n2C1CCN(CC2CCCCCCC2)CC1] | R¹ = methyl, m = 1,<br>X = absent,<br>R² = H,<br>R³ = H,<br>R⁴ = cyclooctyl,<br>Cyc = piperidin-3-yl ((R)-isomer is drawn*) |
| 43 | 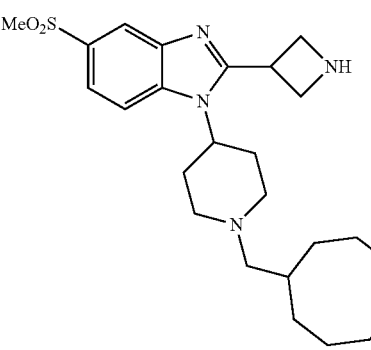 | R¹ = methylsulfonyl, m = 1,<br>X = absent,<br>R² = H,<br>R³ = H,<br>R⁴ = cyclooctyl,<br>Cyc = azetidin-3-yl |
| 44 | 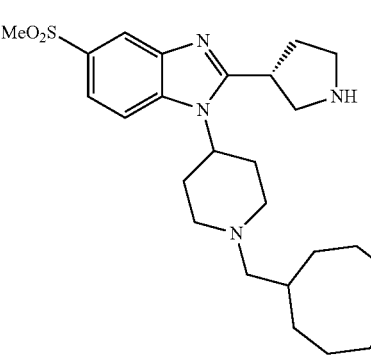 | R¹ = methylsulfonyl, m = 1,<br>X = absent,<br>R² = H,<br>R³ = H,<br>R⁴ = cyclooctyl,<br>Cyc = pyrrolidin-3-yl ((R)-isomer is drawn*) |

TABLE 1-continued

Specifically Claimed Compounds

| # | Structure | Substituents |
|---|---|---|
| 45 | 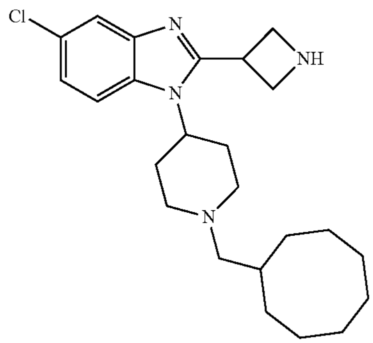 [SMILES: Clc1ccc2c(c1)nc(C1CNC1)n2C1CCN(CC2CCCCCCC2)CC1] | $R^1$ = chloro, m = 1,<br>X = absent,<br>$R^2$ = H,<br>$R^3$ = H,<br>$R^4$ = cyclooctyl,<br>Cyc = azetidin-3-yl |
| 46 | 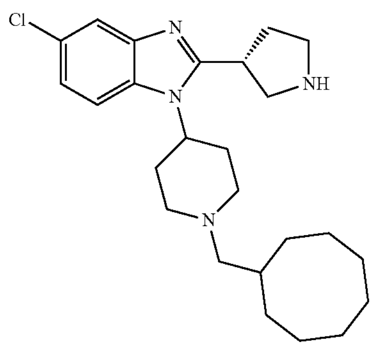 [SMILES: Clc1ccc2c(c1)nc([C@@H]1CCNC1)n2C1CCN(CC2CCCCCCC2)CC1] | $R^1$ = chloro, m = 1,<br>X = absent,<br>$R^2$ = H,<br>$R^3$ = H,<br>$R^4$ = cyclooctyl,<br>Cyc = pyrrolidin-3-yl ((R)-isomer is drawn*) |
| 47 | 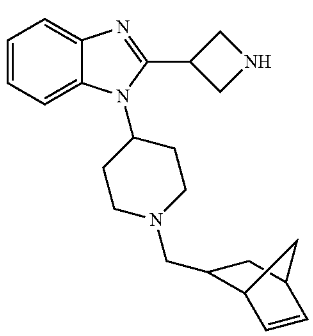 [SMILES: C1=CC2CC1CC2CN1CCC(n2c(C3CNC3)nc3ccccc32)CC1] | $R^1$ = absent,<br>X = absent,<br>$R^2$ = H,<br>$R^3$ = H,<br>$R^4$ = bicyclo[2.2.1]hept-2-en-5-yl,<br>Cyc = azetidin-3-yl |
| 48 | 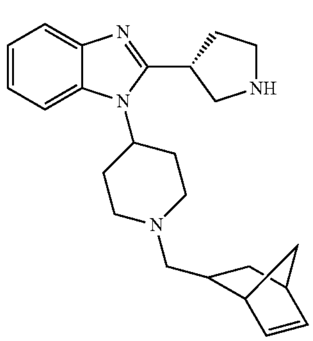 [SMILES: C1=CC2CC1CC2CN1CCC(n2c([C@@H]3CCNC3)nc3ccccc32)CC1] | $R^1$ = absent,<br>X = absent,<br>$R^2$ = H,<br>$R^3$ = H,<br>$R^4$ = bicyclo[2.2.1]hept-2-en-5-yl,<br>Cyc = pyrrolidin-3-yl ((R)-isomer is drawn*) |

TABLE 1-continued

Specifically Claimed Compounds

| # | Structure | Substituents |
|---|-----------|--------------|
| 49 | 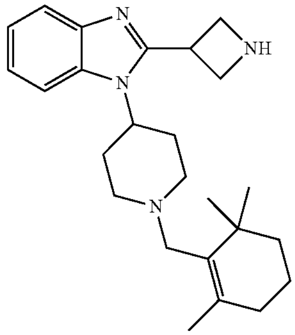 [SMILES: CC1=C(CN2CCC(n3c(C4CNC4)nc4ccccc43)CC2)C(C)(C)CCC1] | $R^1$ = absent,<br>X = absent,<br>$R^2$ = H,<br>$R^3$ = H,<br>$R^4$ = 2,6,6,-trimethylcyclohex-1-enyl,<br>Cyc = azetidin-3-yl |
| 50 | 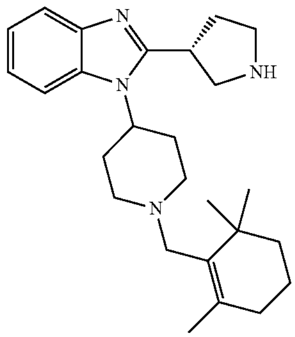 [SMILES: CC1=C(CN2CCC(n3c([C@@H]4CCNC4)nc4ccccc43)CC2)C(C)(C)CCC1] | $R^1$ = absent,<br>X = absent,<br>$R^2$ = H,<br>$R^3$ = H,<br>$R^4$ = 2,6,6,-trimethylcyclohex-1-enyl,<br>Cyc = pyrrolidin-3-yl ((R)-isomer is drawn*) |
| 51 | 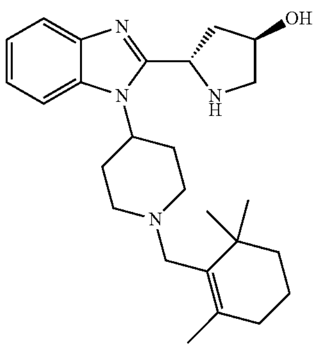 [SMILES: CC1=C(CN2CCC(n3c([C@@H]4C[C@@H](O)CN4)nc4ccccc43)CC2)C(C)(C)CCC1] | $R^1$ = absent,<br>X = absent,<br>$R^2$ = H,<br>$R^3$ = H,<br>$R^4$ = 2,6,6,-trimethylcyclohex-1-enyl,<br>Cyc = 3-hydroxypyrrolidin-5-yl ((3R,5S)-isomer is drawn*) |
| 52 | 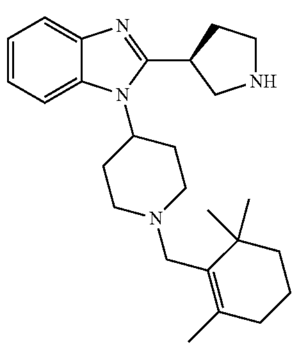 [SMILES: CC1=C(CN2CCC(n3c([C@H]4CCNC4)nc4ccccc43)CC2)C(C)(C)CCC1] | $R^1$ = absent,<br>X = absent,<br>$R^2$ = H,<br>$R^3$ = H,<br>$R^4$ = 2,6,6,-trimethylcyclohex-1-enyl,<br>Cyc = pyrrolidin-3-yl ((S)-isomer is drawn*) |

TABLE 1-continued

Specifically Claimed Compounds

| # | Structure | Substituents |
|---|-----------|--------------|
| 53 | 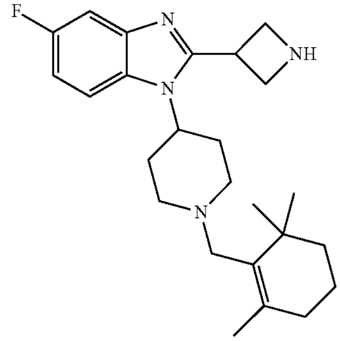 [SMILES: CC1=C(CN2CCC(n3c(C4CNC4)nc4cc(F)ccc43)CC2)C(C)(C)CCC1] | $R^1$ = fluoro, m = 1,<br>X = absent,<br>$R^2$ = H,<br>$R^3$ = H,<br>$R^4$ = 2,6,6,-trimethylcyclohex-1-enyl,<br>Cyc = azetidin-3-yl |
| 54 | 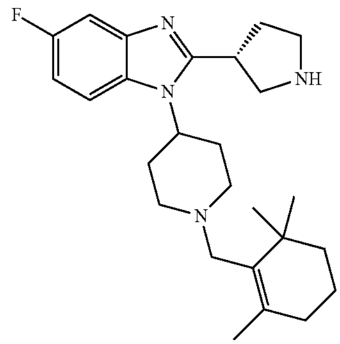 [SMILES: CC1=C(CN2CCC(n3c([C@@H]4CCNC4)nc4cc(F)ccc43)CC2)C(C)(C)CCC1] | $R^1$ = fluoro, m = 1,<br>X = absent,<br>$R^2$ = H,<br>$R^3$ = H,<br>$R^4$ = 2,6,6,-trimethylcyclohex-1-enyl,<br>Cyc = pyrrolidin-3-yl ((R)-isomer is drawn*) |
| 55 | 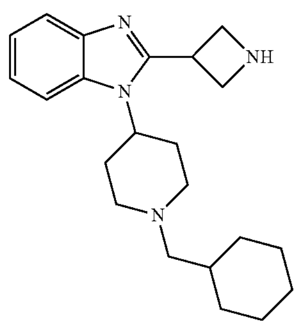 [SMILES: c1ccc2c(c1)nc(C1CNC1)n2C1CCN(CC2CCCCC2)CC1] | $R^1$ = absent,<br>X = absent,<br>$R^2$ = H,<br>$R^3$ = H,<br>$R^4$ = cyclohexyl,<br>Cyc = azetidin-3-yl |
| 56 | 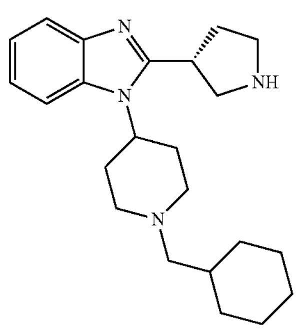 [SMILES: c1ccc2c(c1)nc([C@@H]1CCNC1)n2C1CCN(CC2CCCCC2)CC1] | $R^1$ = absent,<br>X = absent,<br>$R^2$ = H,<br>$R^3$ = H,<br>$R^4$ = cyclohexyl,<br>Cyc = pyrrolidin-3-yl ((R)-isomer is drawn*) |

TABLE 1-continued

Specifically Claimed Compounds

| # | Structure | Substituents |
|---|---|---|
| 57 | 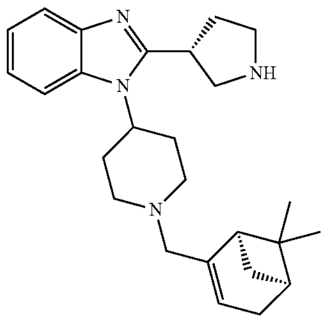 [SMILES: CC1(C)[C@H]2CC=C(CN3CCC(n4c([C@@H]5CCNC5)nc5ccccc54)CC3)[C@@H]1C2] | $R^1$ = absent,<br>X = absent,<br>$R^2$ = H,<br>$R^3$ = H,<br>$R^4$ = 6,6-dimethylbicyclo[3.1.1]-hept-2-en-2-yl,<br>Cyc = pyrrolidin-3-yl ((R)-isomer is drawn*) |
| 58 | 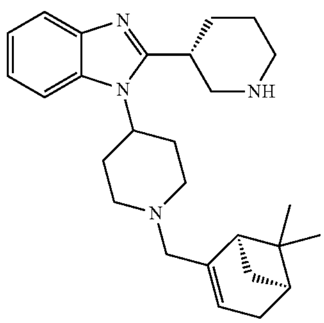 [SMILES: CC1(C)[C@H]2CC=C(CN3CCC(n4c([C@@H]5CCCNC5)nc5ccccc54)CC3)[C@@H]1C2] | $R^1$ = absent,<br>X = absent,<br>$R^2$ = H,<br>$R^3$ = H,<br>$R^4$ = 6,6-dimethylbicyclo[3.1.1]-hept-2-en-2-yl,<br>Cyc = piperidin-3-yl ((R)-isomer is drawn*) |
| 59 | 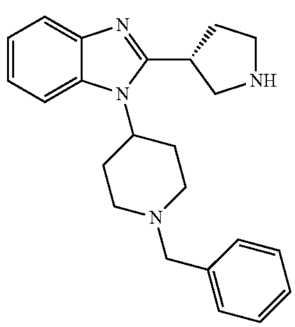 [SMILES: c1ccc(CN2CCC(n3c([C@@H]4CCNC4)nc4ccccc43)CC2)cc1] | $R^1$ = absent,<br>X = absent,<br>$R^2$ = H,<br>$R^3$ = H,<br>$R^4$ = phenyl,<br>Cyc = pyrrolidin-3-yl ((R)-isomer is drawn*) |
| 60 | 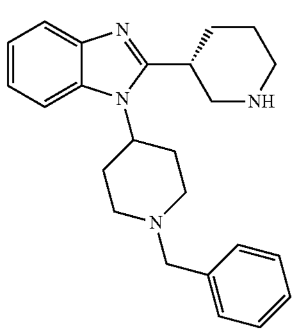 [SMILES: c1ccc(CN2CCC(n3c([C@@H]4CCCNC4)nc4ccccc43)CC2)cc1] | $R^1$ = absent,<br>X = absent,<br>$R^2$ = H,<br>$R^3$ = H,<br>$R^4$ = phenyl,<br>Cyc = piperidin-3-yl ((R)-isomer is drawn*) |

TABLE 1-continued

Specifically Claimed Compounds

| # | Structure | Substituents |
|---|---|---|
| 61 | 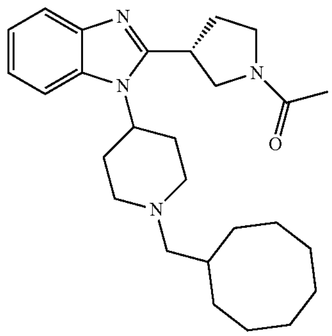 [SMILES: CC(=O)N1CC[C@@H](c2nc3ccccc3n2C2CCN(CC3CCCCCCC3)CC2)C1] | $R^1$ = absent,<br>X = absent,<br>$R^2$ = H,<br>$R^3$ = H,<br>$R^4$ = cyclooctyl,<br>Cyc = 1-acetylpyrrolidin-3-yl ((R)-isomer is drawn*) |
| 62 | 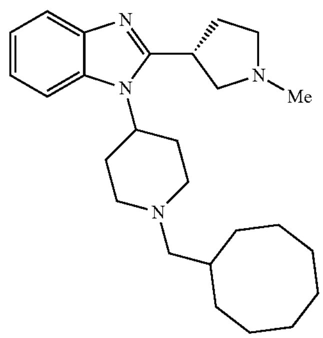 [SMILES: CN1CC[C@@H](c2nc3ccccc3n2C2CCN(CC3CCCCCCC3)CC2)C1] | $R^1$ = absent,<br>X = absent,<br>$R^2$ = H,<br>$R^3$ = H,<br>$R^4$ = cyclooctyl,<br>Cyc = 1-methylpyrrolidin-3-yl ((R)-isomer is drawn*) |
| 63 | 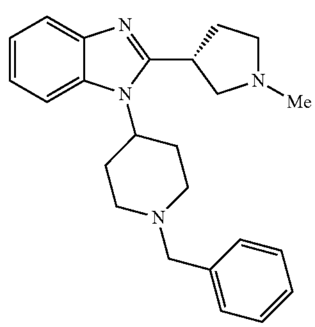 [SMILES: CN1CC[C@@H](c2nc3ccccc3n2C2CCN(Cc3ccccc3)CC2)C1] | $R^1$ = absent,<br>X = absent,<br>$R^2$ = H,<br>$R^3$ = H,<br>$R^4$ = phenyl,<br>Cyc = 1-methylpyrrolidin-3-yl ((R)-isomer is drawn*) |
| 64 | 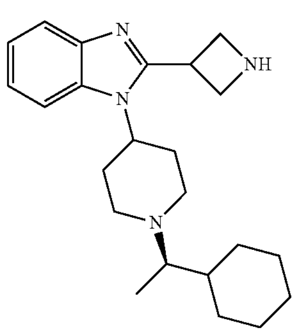 [SMILES: C[C@H](C1CCCCC1)N1CCC(n2c(C3CNC3)nc3ccccc32)CC1] | $R^1$ = absent,<br>X = absent,<br>$R^2$ = (R)-Me*,<br>$R^3$ = H,<br>$R^4$ = cyclohexyl,<br>Cyc = azetidin-3-yl |

TABLE 1-continued

Specifically Claimed Compounds

| # | Structure | Substituents |
|---|-----------|--------------|
| 65 | 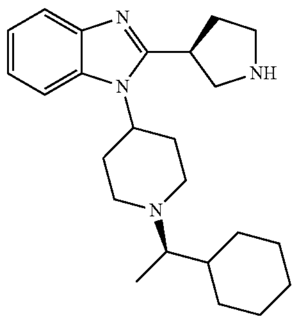 [SMILES: C[C@H](C1CCCCC1)N1CCC(n2c([C@H]3CCNC3)nc3ccccc32)CC1] | R¹ = absent,<br>X = absent,<br>R² = (R)-Me*,<br>R³ = H,<br>R⁴ = cyclohexyl,<br>Cyc = pyrrolidin-3-yl ((S)-isomer is drawn*) |
| 66 | 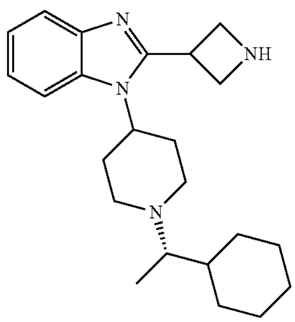 [SMILES: C[C@@H](C1CCCCC1)N1CCC(n2c(C3CNC3)nc3ccccc32)CC1] | R¹ = absent,<br>X = absent,<br>R² = (S)-Me*,<br>R³ = H,<br>R⁴ = cyclohexyl,<br>Cyc = azetidin-3-yl |
| 67 | 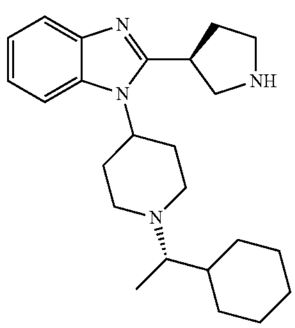 [SMILES: C[C@@H](C1CCCCC1)N1CCC(n2c([C@H]3CCNC3)nc3ccccc32)CC1] | R¹ = absent,<br>X = absent,<br>R² = (S)-Me*,<br>R³ = H,<br>R⁴ = cyclohexyl,<br>Cyc = pyrrolidin-3-yl ((S)-isomer is drawn*) |
| 68 | 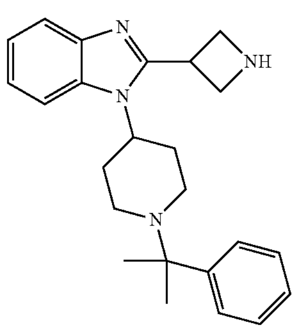 [SMILES: CC(C)(c1ccccc1)N1CCC(n2c(C3CNC3)nc3ccccc32)CC1] | R¹ = absent,<br>X = absent,<br>R² = Me,<br>R³ = Me,<br>R⁴ = phenyl,<br>Cyc = azetidin-3-yl |

TABLE 1-continued

| Specifically Claimed Compounds | | |
|---|---|---|
| # | Structure | Substituents |
| 69 | | $R^1$ = absent,<br>X = absent,<br>$R^2$ = Me,<br>$R^3$ = Me,<br>$R^4$ = phenyl,<br>Cyc = pyrrolidin-3-yl ((R)-isomer is drawn*) |
| 70 | | $R^1$ = absent,<br>X = $CH_2CH_2$ (thus n = 2, R = H),<br>$R^2$ = H,<br>$R^3$ and $R^4$ taken together = cyclooctyl,<br>Cyc = azetidin-3-yl |
| 71 | | $R^1$ = absent,<br>X = $CH_2CH_2$ (thus n = 2, R = H),<br>$R^2$ = H,<br>$R^3$ and $R^4$ taken together = cyclooctyl,<br>Cyc = pyrrolidin-3-yl ((R)-isomer is drawn*) |
| 72 | | $R^1$ = absent,<br>X = $CH_2CH_2$ (thus n = 2, R = H),<br>$R^2$ = H,<br>$R^3$ and $R^4$ taken together = cyclooctyl,<br>Cyc = piperidin-3-yl ((R)-isomer is drawn*) |

TABLE 1-continued

Specifically Claimed Compounds

| # | Structure | Substituents |
|---|---|---|
| 73 | 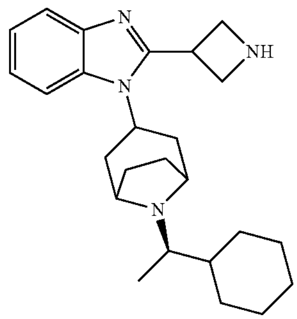 [SMILES: C[C@H](C1CCCCC1)N1C2CCC1CC(n1c(C3CNC3)nc3ccccc31)C2] | $R^1$ = absent, <br> X = $CH_2CH_2$ (thus n = 2, R = H), <br> $R^2$ = (R)-Me*, <br> $R^3$ = H, <br> $R^4$ = cyclohexyl, <br> Cyc = azetidin-3-yl |
| 74 | 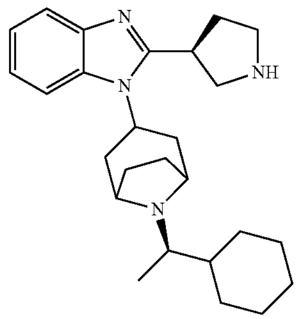 [SMILES: C[C@H](C1CCCCC1)N1C2CCC1CC(n1c([C@H]3CCNC3)nc3ccccc31)C2] | $R^1$ = absent, <br> X = $CH_2CH_2$ (thus n = 2, R = H), <br> $R^2$ = (R)-Me*, <br> $R^3$ = H, <br> $R^4$ = cyclohexyl, <br> Cyc = pyrrolidin-3-yl ((S)-isomer is drawn*) |
| 75 | 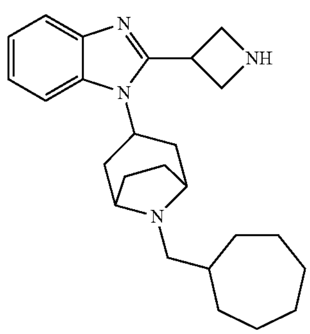 [SMILES: c1ccc2c(c1)nc(C1CNC1)n2C1CC2CCC(C1)N2CC1CCCCCC1] | $R^1$ = absent, <br> X = $CH_2CH_2$ (thus n = 2, R = H), <br> $R^2$ = H, <br> $R^3$ = H, <br> $R^4$ = cycloheptyl, <br> Cyc = azetidin-3-yl |
| 76 | 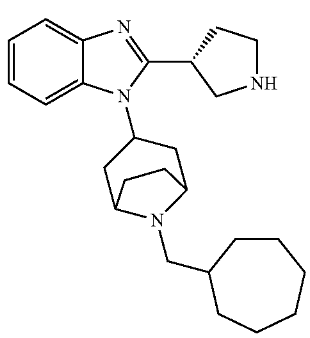 [SMILES: c1ccc2c(c1)nc([C@@H]1CCNC1)n2C1CC2CCC(C1)N2CC1CCCCCC1] | $R^1$ = absent, <br> X = $CH_2CH_2$ (thus n = 2, R = H), <br> $R^2$ = H, <br> $R^3$ = H, <br> $R^4$ = cycloheptyl, <br> Cyc = pyrrolidin-3-yl ((R)-isomer is drawn*) |

TABLE 1-continued

Specifically Claimed Compounds

| # | Structure | Substituents |
|---|---|---|
| 77 | 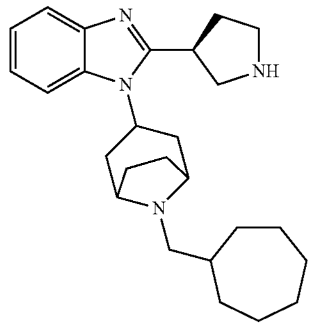 [SMILES: c1ccc2c(c1)nc([C@H]1CCNC1)n2C1CC2CCC(C1)N2CC1CCCCCC1] | $R^1$ = absent,<br>X = $CH_2CH_2$ (thus n = 2, R = H),<br>$R^2$ = H,<br>$R^3$ = H,<br>$R^4$ = cycloheptyl,<br>Cyc = pyrrolidin-3-yl ((S)-isomer is drawn*) |
| 78 | 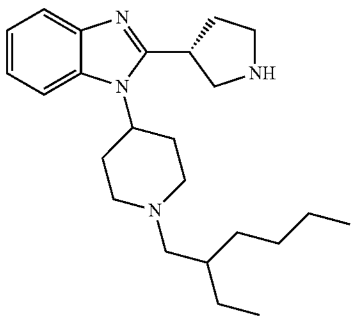 [SMILES: CCCCC(CC)CN1CCC(n2c([C@@H]3CCNC3)nc3ccccc32)CC1] | $R^1$ = absent,<br>X = absent,<br>$R^2$ = H,<br>$R^3$ = H,<br>$R^4$ = Hept-3-yl,<br>Cyc = pyrrolidin-3-yl ((R)-isomer is drawn*) |
| 79 | 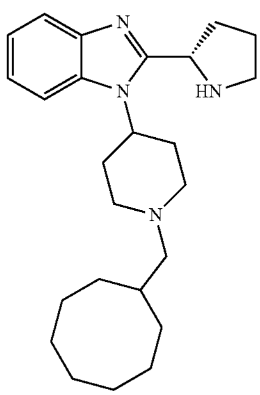 [SMILES: c1ccc2c(c1)nc([C@@H]1CCCN1)n2C1CCN(CC2CCCCCCC2)CC1] | $R^1$ = absent,<br>X = absent,<br>$R^2$ = H,<br>$R^3$ = H,<br>$R^4$ = cyclooctyl,<br>Cyc = pyrrolidin-2-yl ((R)-isomer is drawn*) |
| 80 | 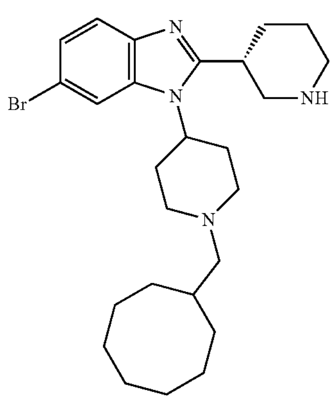 [SMILES: Brc1ccc2nc([C@@H]3CCCNC3)n(C3CCN(CC4CCCCCCC4)CC3)c2c1] | $R^1$ = bromo, m = 1,<br>X = absent,<br>$R^2$ = H,<br>$R^3$ = H,<br>$R^4$ = cyclooctyl,<br>Cyc = piperidin-3-yl ((R)-isomer is drawn*) |

TABLE 1-continued

Specifically Claimed Compounds

| # | Structure | Substituents |
|---|-----------|--------------|
| 81 | 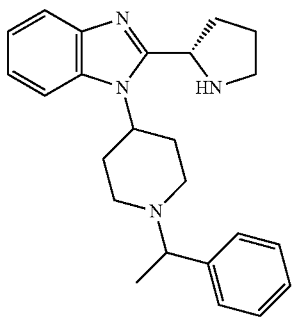 [SMILES: CC(c1ccccc1)N1CCC(n2c([C@@H]3CCCN3)nc3ccccc32)CC1] | R¹ = absent,<br>X = absent,<br>R² = Me,<br>R³ = H,<br>R⁴ = phenyl,<br>Cyc = pyrrolidin-2-yl ((R)-isomer is drawn*) |
| 82 | 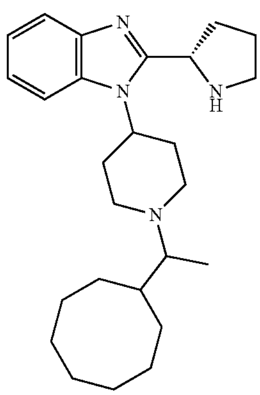 [SMILES: CC(C1CCCCCCC1)N1CCC(n2c([C@@H]3CCCN3)nc3ccccc32)CC1] | R¹ = absent,<br>X = absent,<br>R² = Me,<br>R³ = H,<br>R⁴ = cyclooctyl,<br>Cyc = pyrrolidin-2-yl ((R)-isomer is drawn*) |
| 83 | 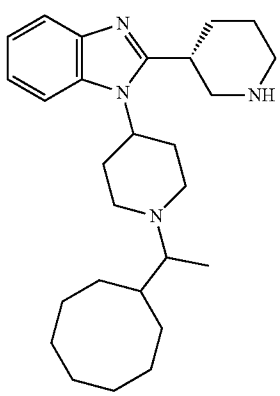 [SMILES: CC(C1CCCCCCC1)N1CCC(n2c([C@@H]3CCCNC3)nc3ccccc32)CC1] | R¹ = absent,<br>X = absent,<br>R² = Me,<br>R³ = H,<br>R⁴ = cyclooctyl,<br>Cyc = piperidin-3-yl ((R)-isomer is drawn*) |
| 84 | 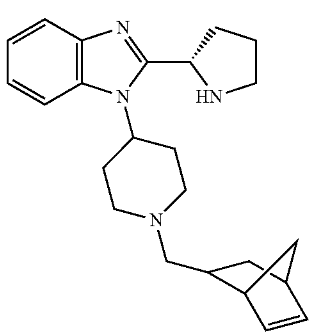 [SMILES: C1=CC2CC1CC2CN1CCC(n2c([C@@H]3CCCN3)nc3ccccc32)CC1] | R¹ = absent,<br>X = absent,<br>R² = H,<br>R³ = H,<br>R⁴ = bicyclo[2.2.1]hept-2-en-5-yl,<br>Cyc = pyrrolidin-2-yl ((R)-isomer is drawn*) |

TABLE 1-continued

Specifically Claimed Compounds

| # | Structure | Substituents |
|---|---|---|
| 85 | 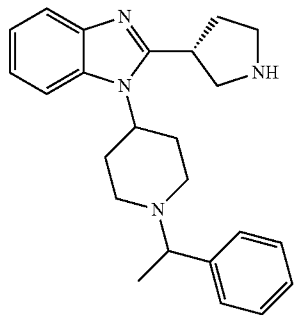 [SMILES: CC(c1ccccc1)N1CCC(n2c([C@@H]3CCNC3)nc3ccccc32)CC1] | R[1] = absent,<br>X = absent,<br>R[2] = Me,<br>R[3] = H,<br>R[4] = phenyl,<br>Cyc = pyrrolidin-3-yl ((R)-isomer is drawn*) |
| 86 | 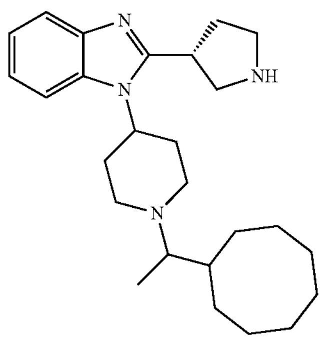 [SMILES: CC(C1CCCCCCC1)N1CCC(n2c([C@@H]3CCNC3)nc3ccccc32)CC1] | R[1] = absent,<br>X = absent,<br>R[2] = Me,<br>R[3] = H,<br>R[4] = cyclooctyl,<br>Cyc = pyrrolidin-3-yl ((R)-isomer is drawn*) |
| 87 | 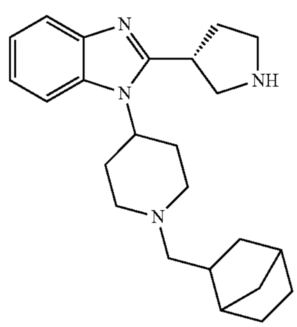 [SMILES: c1ccc2c(c1)nc([C@@H]1CCNC1)n2C1CCN(CC2CC3CCC2C3)CC1] | R[1] = absent,<br>X = absent,<br>R[2] = H,<br>R[3] = H,<br>R[4] = cyclooctyl,<br>Cyc = 2-bicyclo[2.2.1]heptane |
| 88 | 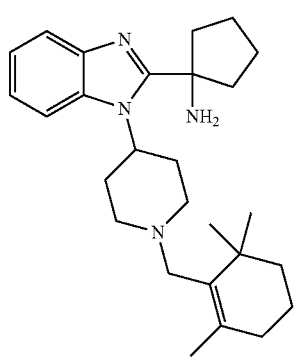 [SMILES: CC1=C(CN2CCC(n3c(C4(N)CCCC4)nc4ccccc43)CC2)C(C)(C)CCC1] | R[1] = absent,<br>X = absent,<br>R[2] = H,<br>R[3] = H,<br>R[4] = 2,6,6,-trimethylcyclohex-1-enyl,<br>Cyc = 1-aminocyclopentyl |

TABLE 1-continued

| Specifically Claimed Compounds | | |
|---|---|---|
| # | Structure | Substituents |
| 89 | | $R^1$ = absent,<br>X = absent,<br>$R^2$ = H,<br>$R^3$ = H,<br>$R^4$ = cyclooctyl,<br>Cyc = pyrrolidin-2-yl ((R)-isomer is drawn*) |
| 90 | | $R^1$ = absent,<br>X = absent,<br>$R^2$ = H,<br>$R^3$ = H,<br>$R^4$ = 3-chlorophenyl<br>Cyc = pyrrolidin-3-yl ((R)-isomer is drawn*) |
| 91 | | $R^1$ = absent,<br>X = absent,<br>$R^2$ = H,<br>$R^3$ = H,<br>$R^4$ = 3-bromophenyl<br>Cyc = pyrrolidin-3-yl ((R)-isomer is drawn*) |
| 92 | | $R^1$ = absent,<br>X = absent,<br>$R^2$ = H,<br>$R^3$ = H,<br>$R^4$ = 2.3-methylenedioxyphenyl<br>Cyc = pyrrolidin-3-yl ((R)-isomer is drawn*) |

TABLE 1-continued

Specifically Claimed Compounds

| # | Structure | Substituents |
|---|-----------|--------------|
| 93 | 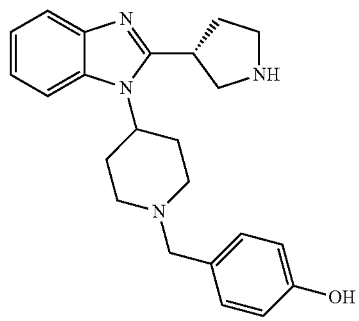 [SMILES: Oc1ccc(CN2CCC(n3c([C@@H]4CCNC4)nc4ccccc43)CC2)cc1] | R$^1$ = absent,<br>X = absent,<br>R$^2$ = H,<br>R$^3$ = H,<br>R$^4$ = 4-hydroxyphenyl<br>Cyc = pyrrolidin-3-yl ((R)-isomer is drawn*) |
| 94 | 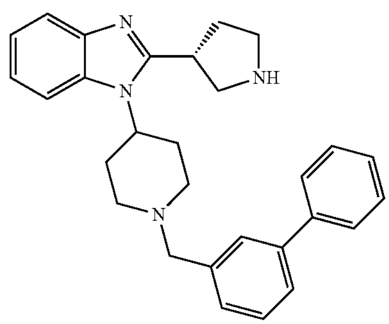 [SMILES: c1ccc(-c2cccc(CN3CCC(n4c([C@@H]5CCNC5)nc5ccccc54)CC3)c2)cc1] | R$^1$ = absent,<br>X = absent,<br>R$^2$ = H,<br>R$^3$ = H,<br>R$^4$ = 3-(1,1')-biphenyl<br>Cyc = pyrrolidin-3-yl ((R)-isomer is drawn*) |
| 95 | 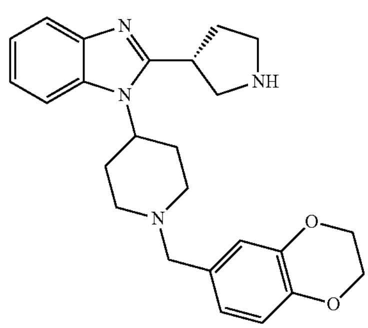 [SMILES: c1ccc2c(c1)nc([C@@H]1CCNC1)n2C1CCN(Cc2ccc3c(c2)OCCO3)CC1] | R$^1$ = absent,<br>X = absent,<br>R$^2$ = H,<br>R$^3$ = H,<br>R$^4$ = 6-(2,3-dihydrobenzo[b][1,4]dioxinyl)<br>Cyc = pyrrolidin-3-yl ((R)-isomer is drawn*) |
| 96 | 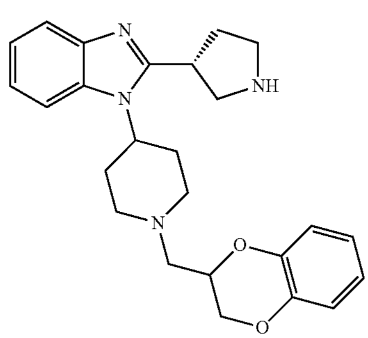 [SMILES: c1ccc2c(c1)OCC(CN1CCC(n3c([C@@H]4CCNC4)nc4ccccc43)CC1)O2] | R$^1$ = absent,<br>X = absent,<br>R$^2$ = H,<br>R$^3$ = H,<br>R$^4$ = 2-(2,3-dihydrobenzo[b][1,4]dioxinyl)<br>Cyc = pyrrolidin-3-yl ((R)-isomer is drawn*) |

TABLE 1-continued

Specifically Claimed Compounds

| # | Structure | Substituents |
|---|---|---|
| 97 | 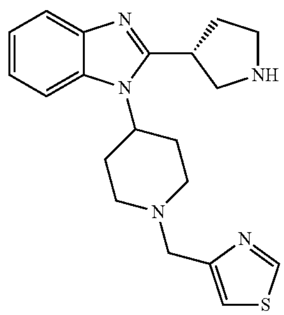 [SMILES: c1ccc2c(c1)nc([C@@H]1CCNC1)n2C1CCN(Cc2cscn2)CC1] | R¹ = absent,<br>X = absent,<br>R² = H,<br>R³ = H,<br>R⁴ = 4-thiazolyl<br>Cyc = pyrrolidin-3-yl ((R)-isomer is drawn*) |
| 98 | 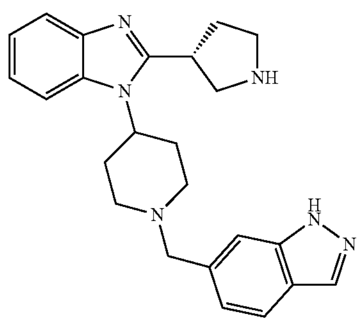 [SMILES: c1ccc2c(c1)nc([C@@H]1CCNC1)n2C1CCN(Cc2ccc3cn[nH]c3c2)CC1] | R¹ = absent,<br>X = absent,<br>R² = H,<br>R³ = H,<br>R⁴ = 6-indazolyl<br>Cyc = pyrrolidin-3-yl ((R)-isomer is drawn*) |
| 99 | 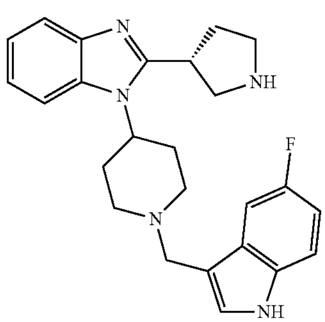 [SMILES: Fc1ccc2[nH]cc(CN3CCC(n4c([C@@H]5CCNC5)nc5ccccc54)CC3)c2c1] | R¹ = absent,<br>X = absent,<br>R² = H,<br>R³ = H,<br>R⁴ = 3-(5-fluoroindolyl)<br>Cyc = pyrrolidin-3-yl ((R)-isomer is drawn*) |
| 100 | 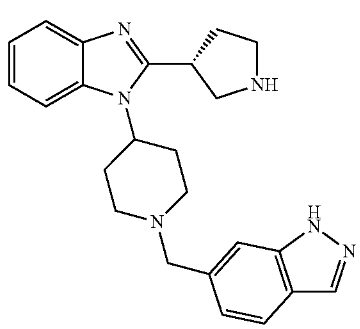 [SMILES: c1ccc2c(c1)nc([C@@H]1CCNC1)n2C1CCN(Cc2ccc3cn[nH]c3c2)CC1] | R¹ = absent,<br>X = absent,<br>R² = H,<br>R³ = H,<br>R⁴ = 6-(1H-benimidazolyl)<br>Cyc = pyrrolidin-3-yl ((R)-isomer is drawn*) |

TABLE 1-continued

Specifically Claimed Compounds

| # | Structure | Substituents |
|---|---|---|
| 101 | 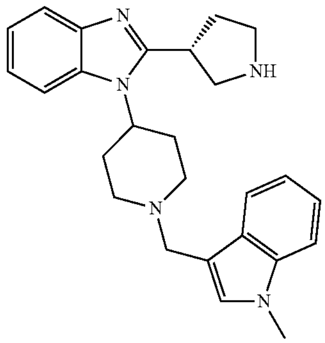 [SMILES: Cn1cc(CN2CCC(n3c([C@@H]4CCNC4)nc4ccccc43)CC2)c2ccccc21] | R¹ = absent,<br>X = absent,<br>R² = H,<br>R³ = H,<br>R⁴ = 3-(1-methylindolyl)<br>Cyc = pyrrolidin-3-yl ((R)-isomer is drawn*) |
| 102 | 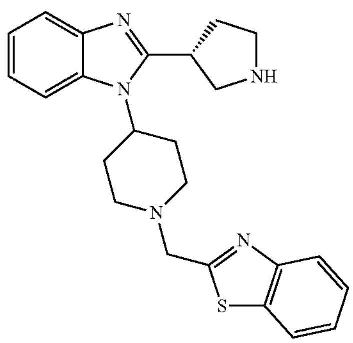 [SMILES: c1ccc2sc(CN3CCC(n4c([C@@H]5CCNC5)nc5ccccc54)CC3)nc2c1] | R¹ = absent,<br>X = absent,<br>R² = H,<br>R³ = H,<br>R⁴ = 2-(benzothiazolyl)<br>Cyc = pyrrolidin-3-yl ((R)-isomer is drawn*) |
| 103 | 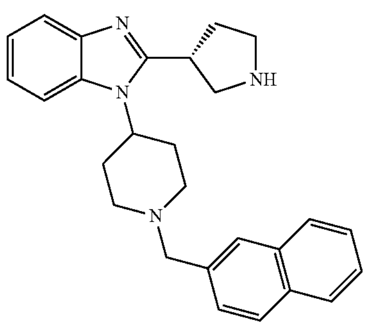 [SMILES: c1ccc2cc(CN3CCC(n4c([C@@H]5CCNC5)nc5ccccc54)CC3)ccc2c1] | R¹ = absent,<br>X = absent,<br>R² = H,<br>R³ = H,<br>R⁴ = 2-naphthyl<br>Cyc = pyrrolidin-3-yl ((R)-isomer is drawn*) |
| 104 | 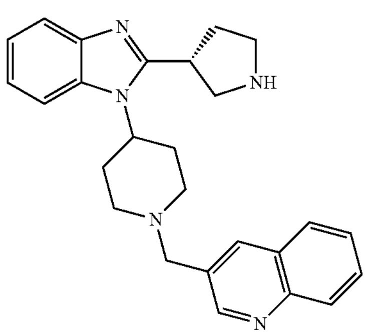 [SMILES: c1ccc2ncc(CN3CCC(n4c([C@@H]5CCNC5)nc5ccccc54)CC3)cc2c1] | R¹ = absent,<br>X = absent,<br>R² = H,<br>R³ = H,<br>R⁴ = 3-(quinolinyl)<br>Cyc = pyrrolidin-3-yl ((R)-isomer is drawn*) |

TABLE 1-continued

Specifically Claimed Compounds

| # | Structure | Substituents |
|---|---|---|
| 105 | 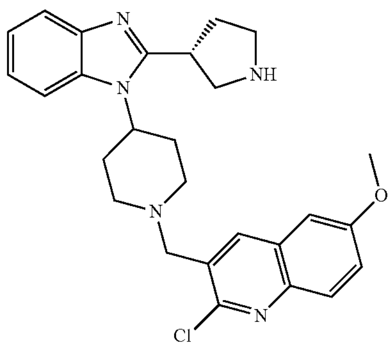 [SMILES: COc1ccc2nc(Cl)c(CN3CCC(n4c([C@@H]5CCNC5)nc5ccccc54)CC3)cc2c1] | R¹ = absent,<br>X = absent,<br>R² = H,<br>R³ = H,<br>R⁴ = 3-(2-chloro,6-methoxyquinolinyl)<br>Cyc = pyrrolidin-3-yl ((R)-isomer is drawn*) |
| 106 | 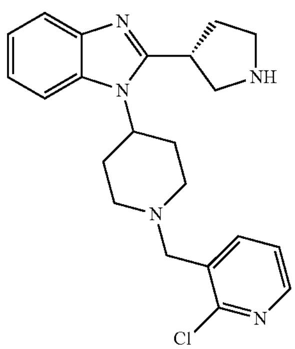 [SMILES: Clc1ncccc1CN1CCC(n2c([C@@H]3CCNC3)nc3ccccc32)CC1] | R¹ = absent,<br>X = absent,<br>R² = H,<br>R³ = H,<br>R⁴ = 3-(2-chloropyridyl)<br>Cyc = pyrrolidin-3-yl ((R)-isomer is drawn*) |
| 107 | 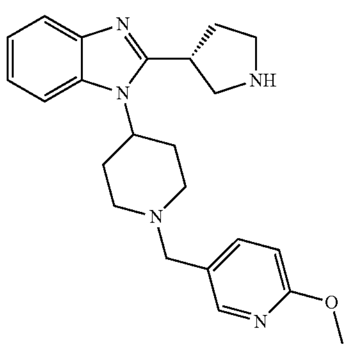 [SMILES: COc1ccc(CN2CCC(n3c([C@@H]4CCNC4)nc4ccccc43)CC2)cn1] | R¹ = absent,<br>X = absent,<br>R² = H,<br>R³ = H,<br>R⁴ = 3-(6-methoxypyridyl)<br>Cyc = pyrrolidin-3-yl ((R)-isomer is drawn*) |
| 108 | 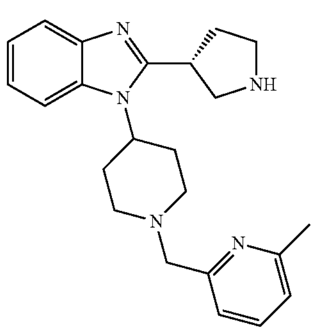 [SMILES: Cc1cccc(CN2CCC(n3c([C@@H]4CCNC4)nc4ccccc43)CC2)n1] | R¹ = absent,<br>X = absent,<br>R² = H,<br>R³ = H,<br>R⁴ = 2-(6-methylpyridyl)<br>Cyc = pyrrolidin-3-yl ((R)-isomer is drawn*) |

TABLE 1-continued

Specifically Claimed Compounds

| # | Structure | Substituents |
|---|---|---|
| 109 | 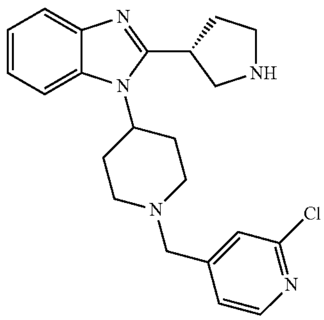 [SMILES: Clc1cc(CN2CCC(n3c([C@@H]4CCNC4)nc4ccccc43)CC2)ccn1] | R¹ = absent,<br>X = absent,<br>R² = H,<br>R³ = H,<br>R⁴ = 4-(2-chloropyridyl)<br>Cyc = pyrrolidin-3-yl ((R)-isomer is drawn*) |
| 110 | 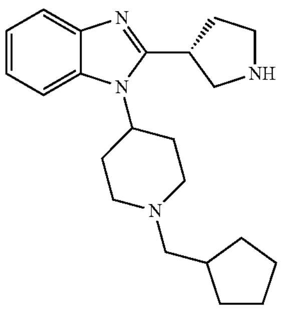 [SMILES: c1ccc2c(c1)nc([C@@H]1CCNC1)n2C1CCN(CC2CCCC2)CC1] | R¹ = absent,<br>X = absent,<br>R² = H,<br>R³ = H,<br>R⁴ = cylcopentanyl<br>Cyc = pyrrolidin-3-yl ((R)-isomer is drawn*) |
| 111 | 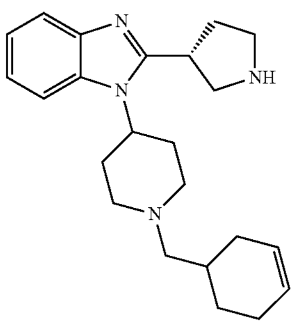 [SMILES: C1=CCC(CN2CCC(n3c([C@@H]4CCNC4)nc4ccccc43)CC2)CC1] | R¹ = absent,<br>X = absent,<br>R² = H,<br>R³ = H,<br>R⁴ = 4-(1,2-cyclohexenyl)<br>Cyc = pyrrolidin-3-yl ((R)-isomer is drawn*) |
| 112 | 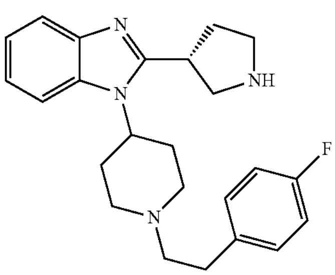 [SMILES: Fc1ccc(CCN2CCC(n3c([C@@H]4CCNC4)nc4ccccc43)CC2)cc1] | R¹ = absent,<br>X = absent,<br>R² = H,<br>R³ = H,<br>R⁴ = 4-fluorobenzyl<br>Cyc = pyrrolidin-3-yl ((R)-isomer is drawn*) |
| 113 | 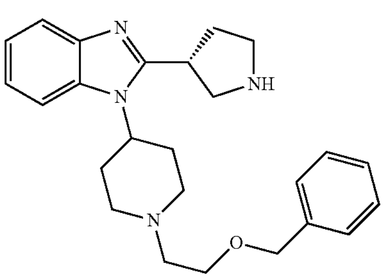 [SMILES: c1ccc(COCCN2CCC(n3c([C@@H]4CCNC4)nc4ccccc43)CC2)cc1] | R¹ = absent,<br>X = absent,<br>R² = H,<br>R³ = H,<br>R⁴ = phenylmethoxy<br>Cyc = pyrrolidin-3-yl ((R)-isomer is drawn*) |

TABLE 1-continued

Specifically Claimed Compounds

| # | Structure | Substituents |
|---|-----------|--------------|
| 114 | 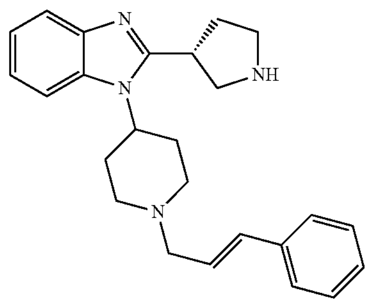 [SMILES: C(=C\c1ccccc1)/CN1CCC(n2c([C@@H]3CCNC3)nc3ccccc32)CC1] | $R^1$ = absent,<br>X = absent,<br>$R^2$ = H,<br>$R^3$ = H,<br>$R^4$ = trans-phenylethylenyl<br>Cyc = pyrrolidin-3-yl ((R)-isomer is drawn*) |
| 115 | 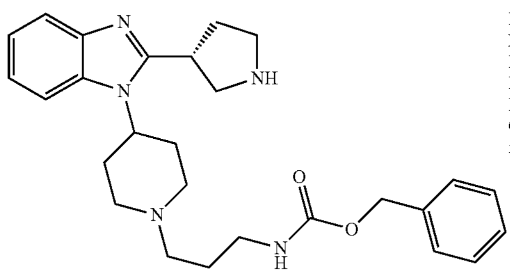 | $R^1$ = absent,<br>X = absent,<br>$R^2$ = H,<br>$R^3$ = H,<br>$R^4$ = N-Cbz-2-aminoethyl<br>Cyc = pyrrolidin-3-yl ((R)-isomer is drawn*) |
| 116 | 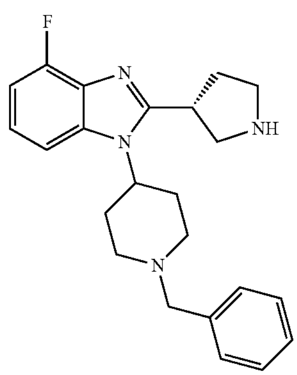 [SMILES: Fc1cccc2c1nc([C@@H]1CCNC1)n2C1CCN(Cc2ccccc2)CC1] | $R^1$ = 4-fluoro,<br>X = absent,<br>$R^2$ = H,<br>$R^3$ = H,<br>$R^4$ = phenyl<br>Cyc = pyrrolidin-3-yl ((R)-isomer is drawn*) |
| 117 | 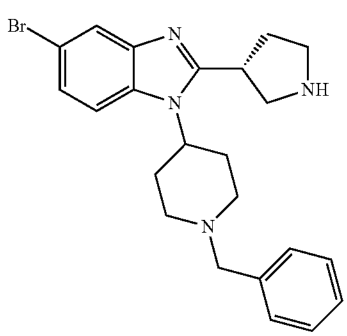 | $R^1$ = 5-bromo,<br>X = absent,<br>$R^2$ = H,<br>$R^3$ = H,<br>$R^4$ = phenyl<br>Cyc = pyrrolidin-3-yl ((R)-isomer is drawn*) |

TABLE 1-continued

Specifically Claimed Compounds

| # | Structure | Substituents |
|---|-----------|--------------|
| 118 | 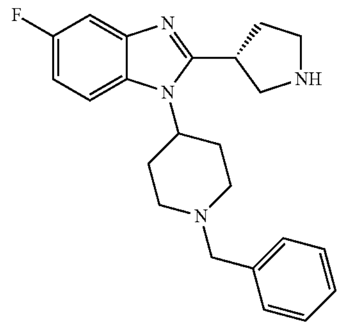 [SMILES: Fc1ccc2c(c1)nc([C@@H]1CCNC1)n2C1CCN(Cc2ccccc2)CC1] | R¹ = 5-fluoro,<br>X = absent,<br>R² = H,<br>R³ = H,<br>R⁴ = phenyl<br>Cyc = pyrrolidin-3-yl ((R)-isomer is drawn*) |
| 119 | 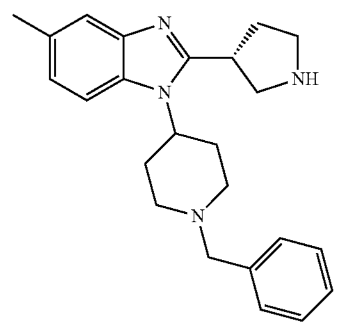 [SMILES: Cc1ccc2c(c1)nc([C@@H]1CCNC1)n2C1CCN(Cc2ccccc2)CC1] | R¹ = 5-methyl,<br>X = absent,<br>R² = H,<br>R³ = H,<br>R⁴ = phenyl<br>Cyc = pyrrolidin-3-yl ((R)-isomer is drawn*) |
| 120 | 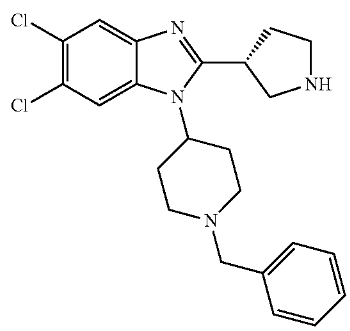 [SMILES: Clc1cc2nc([C@@H]3CCNC3)n(C3CCN(Cc4ccccc4)CC3)c2cc1Cl] | R¹ = 5,6-dichloro,<br>X = absent,<br>R² = H,<br>R³ = H,<br>R⁴ = phenyl<br>Cyc = pyrrolidin-3-yl ((R)-isomer is drawn*) |
| 121 | 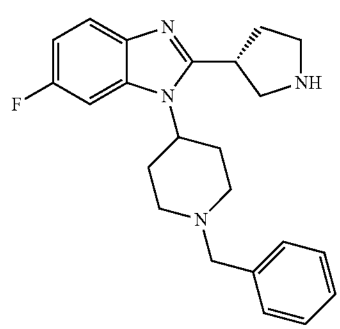 [SMILES: Fc1ccc2nc([C@@H]3CCNC3)n(C3CCN(Cc4ccccc4)CC3)c2c1] | R¹ = 6-fluoro,<br>X = absent,<br>R² = H,<br>R³ = H,<br>R⁴ = phenyl<br>Cyc = pyrrolidin-3-yl ((R)-isomer is drawn*) |

TABLE 1-continued

Specifically Claimed Compounds

| # | Structure | Substituents |
|---|-----------|--------------|
| 122 | 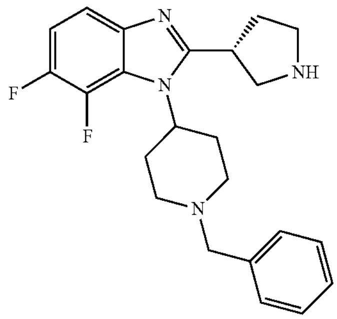 [SMILES: Fc1ccc2nc([C@@H]3CCNC3)n(C3CCN(Cc4ccccc4)CC3)c2c1F] | $R^1$ = 6,7-difluoro, X = absent, $R^2$ = H, $R^3$ = H, $R^4$ = phenyl, Cyc = pyrrolidin-3-yl ((R)-isomer is drawn*) |
| 123 | 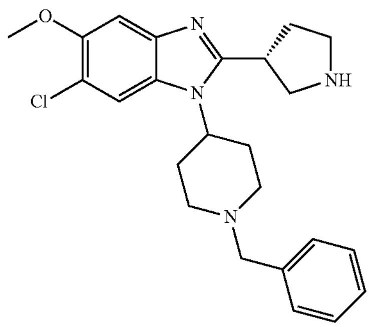 [SMILES: COc1cc2nc([C@@H]3CCNC3)n(C3CCN(Cc4ccccc4)CC3)c2cc1Cl] | $R^1$ = 5-methoxy6-chloro, X = absent, $R^2$ = H, $R^3$ = H, $R^4$ = phenyl, Cyc = pyrrolidin-3-yl ((R)-isomer is drawn*) |

*All chiral, diastereomeric, racemic forms of a structure are intended in Table 1.

In several instances an individual stereoisomer is depicted (see compound 3 for one example), but this does not imply that alternate isomeric forms are less preferred, undesired, or not claimed. In other instances the configuration of one or more stereocenters is not depicted (see compound 87 for one example), but this does not imply that single isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

Synthetic Methods

Three general methods are illustrated for the synthesis of compounds of the current invention. In some instances more than one method can be used for the preparation of the same compound and thus the illustration of one particular method does not imply that another method might not also be used.

Method 1

In this general method, N-ethyl piperidine-4-one A is used to form a N,N-dialkylated piperidin-4-one salt B. This salt is used in an exchange reaction with amine C to form an N-alkylated piperidin-4-one D. Condensation of the C=O group with an α-amino aniline E and reduction of the intermediate imine forms intermediate F. (The reducing agent NaBH(OAc)₃ is shown, though other agents may alternatively be used). Standard coupling of an amine group in F with a carboxylic acid G installs the Cyc group of the invention, in protected form if applicable (the carbodiimide coupling agent EDC is shown, though other agents may alternatively be used). Dehydrative closure of the benzimidazole ring and finally removal of acid labile N- or O-protecting groups (if present) gives the test compounds H. If alternative non acid-labile N- or O-protecting groups are present in carboxylic acid G, reaction conditions standard for their removal are used in place of the final acidic step shown, such has hydrogenolysis of Cbz groups, as one example. If no N- or O-protecting groups are present in carboxylic acid G, the final acidic step shown is omitted.

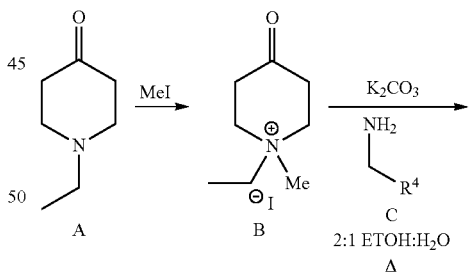

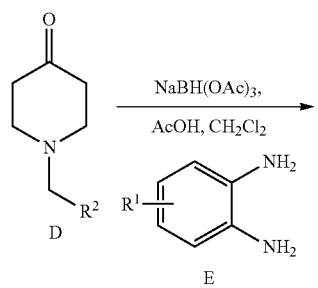

-continued

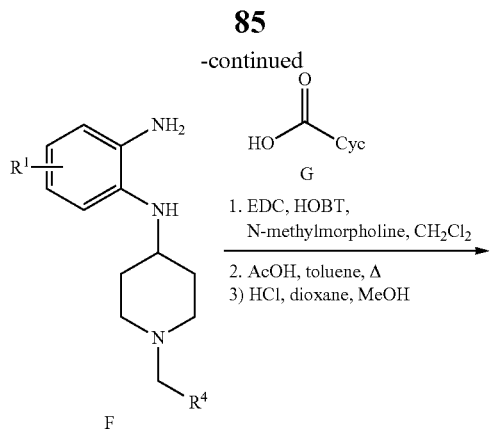

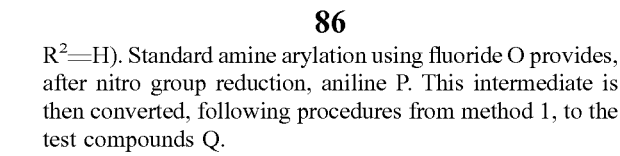

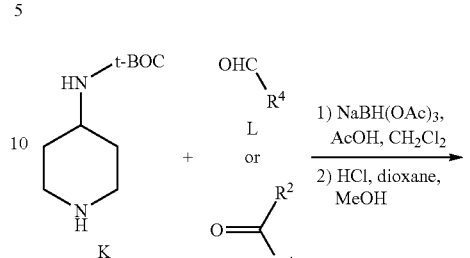

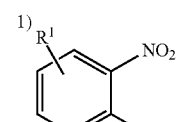

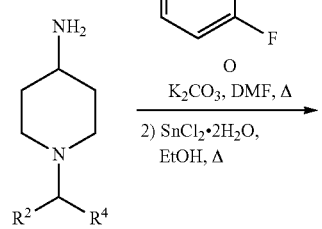

$R^2$=H). Standard amine arylation using fluoride O provides, after nitro group reduction, aniline P. This intermediate is then converted, following procedures from method 1, to the test compounds Q.

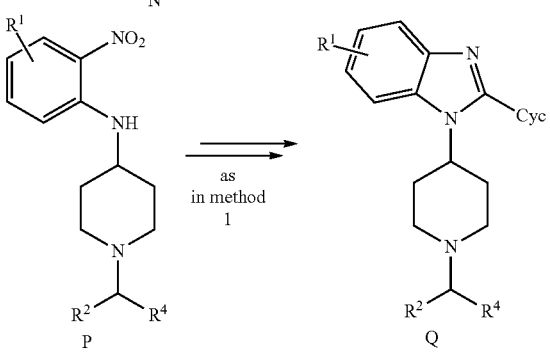

Method 2

In this general method the test compounds wherein the bridging X group is present may be prepared. For example, in the case where X=CH$_2$CH$_2$ the salt I is used in place of salt B, but generally following the procedures of method 1. Test compound J results. Alternatively, the product J can have a suitable protecting group on the piperidine nitrogen atom. This protecting group is removed by standard means and the resultant amine is converted to test compound K.

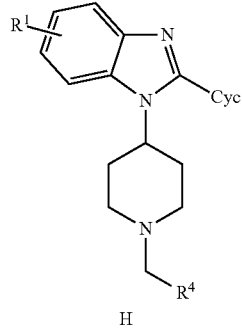

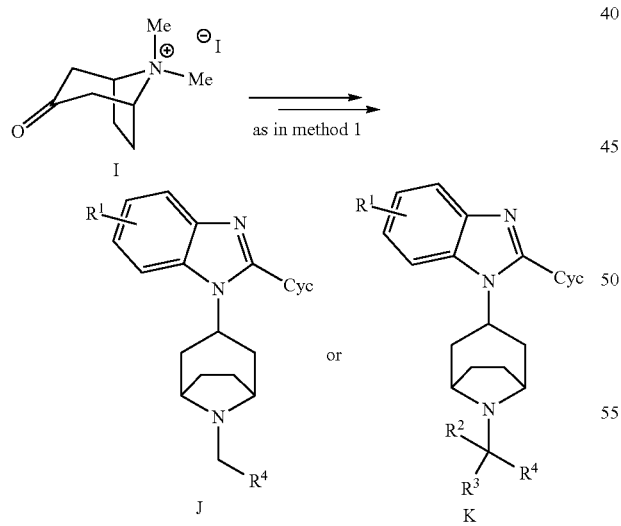

Willand, et al. Tetrahedron Lett. 2007, 48, 5007.

Method 3

In this general method the protected amino piperidine K is used in an alkylation reaction with either an aldehyde L or a ketone M to give, after protecting group removal, amine N (in the case of an aldehyde L, the resulting product N has

SYNTHETIC EXAMPLES

Example 1

2-(Azetidin-3-yl)-1-(1-(cycloheptylmethyl)piperidin-4-yl)-1H-benzo[d]imidazole

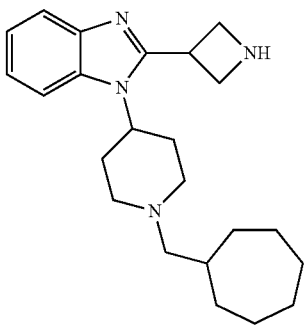 [SMILES: c1ccc2c(c1)nc(C1CNC1)n2C1CCN(CC2CCCCCC2)CC1]

(a) 1-Ethyl-1-methyl-4-oxopiperidinium iodide

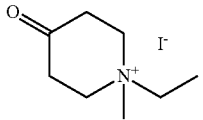

To a solution of 1-ethyl-4-piperidone (10 g, 78.6 mmol) in acetone (100 mL) was added methyl iodide (6.5 mL, 100 mmol) and the mixture was stirred at rt for 4 h. The precipitate was filtered, washed with acetone, and dried under vacuum to yield 19.76 g (93%) of the title compound as a beige solid.

(b) 1-(Cycloheptylmethyl)piperidin-4-one

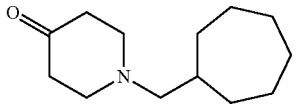 [SMILES: O=C1CCN(CC2CCCCCC2)CC1]

To solution of 1-ethyl-1-methyl-4-oxopiperidinium iodide (4.5 g, 16.7 mmol) in ethanol (60 mL) and water (30 mL) was added aminomethylcycloheptane (2.12 g, 16.7 mmol) and $K_2CO_3$ (3.30 g, 23.9 mmol). After the resulting mixture was stirred at 80° C. for 3 h, the organic solvent was removed by rotary evaporation and extracted three times with methylene chloride (30 mL). The organic layers were combined, dried over sodium sulfate, and concentrated. The residue was purified by flash column chromatography (2 to 25% ethyl acetate in hexanes) to yield the 2.10 g (60%) title compound as a pale yellow oil: $^1$H NMR (CDCl$_3$, 400 MHz) δ 2.67 (t, J=6.0 Hz, 4H), 2.43 (t, J=6.0 Hz, 4H), 2.20 (d, J=7.6 Hz, 2H), 1.87-1.77 (m, 2H), 1.71-1.38 (m, 9H), 1.15 (m, 2H). LRMS (ES+) m/z for $C_{13}H_{24}NO$ [M+H]$^+$ calc'd 210. found 210.

(c) $N^1$-(1-(cycloheptylmethyl)piperidin-4-yl)benzene-1,2-diamine

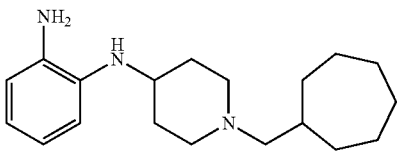 [SMILES: Nc1ccccc1NC1CCN(CC2CCCCCC2)CC1]

Sodium triacetoxyborohydride (0.850 g, 4.01 mmol) was added to a mixture of 1,2-phenylenediamine (0.300 g, 2.77 mmol), the product from Example 1b (0.420 g, 2.01 mmol), and acetic acid (0.5 mL) in methylene chloride (30 mL) and the resulting reaction was stirred overnight. The solvent was removed by rotary evaporation, treated with a saturated aqueous solution of NaHCO$_3$ (25 mL), and extracted three times with methylene chloride (15 mL). The organic layers were combined, dried over sodium sulfate, and concentrated. The residue was purified by flash column chromatography (1 to 9% methanol in methylene chloride with 0.1% NH$_4$OH) to yield 0.39 g (65%) of the title compound as a purple oil: $^1$H NMR (CDCl$_3$, 400 MHz) δ 6.79 (ddd, J=8.0, 7.2, 1.6 Hz, 1H), 6.72 (dd, J=8.0, 1.6 Hz, 1H), 6.67 (d, J=7.6 Hz, 2H), 3.30 (br s, 2H), 3.25 (tt, J=10.4, 4.0 Hz, 1H), 2.81 (m, 2H), 2.10 (d, J=7.2 Hz, 2H), 2.04 (t, J=10.0 Hz, 4H), 1.77 (m, 2H), 1.69-1.37 (m, 12H), 1.11 (m, 2H). LRMS (ES+) m/z for $C_{19}H_{32}N_3$ [M+H]$^+$ calc'd 302. found 302.

(d) 2-(Azetidin-3-yl)-1-(1-(cycloheptylmethyl)piperidin-4-yl)-1H-benzo[d]imidazole To a solution of the product from Example 1c (40 mg, 0.133 mmol) in methylene chloride (5 mL) was added 1-(tert-butoxycarbonyl)azetidine-3-carboxylic acid (27 mg, 0.134 mmol, (prepared as described in Antonsson et al, WO 2008/004946), N-hydroxybenzotriazole (HOBT, 22 mg, 0.144 mmol), N-methylmorpholine (0.03 mL, 0.265 mmol), and 1-ethyl-3-(3'-dimethylaminopropyl)carbodiimide hydrochloride (EDC, 51 mg, 0.265 mmol). The resulting mixture was stirred at room temperature overnight. After removal of solvent by rotary evaporation, the residue was dissolved in methylene chloride (10 mL) and washed with a saturated aqueous solution of NaHCO$_3$ (10 mL). The aqueous layer was extracted twice with additional methylene chloride (5 mL) and the combined organic layers were dried over Na$_2$SO$_4$, filtered, and concentrated in vacuo. Without further purification, the brown residue was dissolved in toluene (1.5 mL) and acetic acid (0.5 mL) and stirred at 100° C. overnight. The solution was cooled, concentrated, and partitioned between a saturated aqueous solution of NaHCO$_3$ (10 mL) and methylene chloride (10 mL). The layers were separated, and the aqueous layer was extracted with two additional portions of methylene chloride (10 mL). The organic layers were combined, dried over Na$_2$SO$_4$, filtered, concentrated in vacuo, and purified by flash column chromatography (8 to 45% ethyl acetate in hexanes). The obtained oil was dissolved in methanol (1.5 mL) and to this solution was added 4 M HCl in dioxane (0.5 mL). After stirring at room temperature overnight, the solvent was removed, treated with a saturated aqueous solution of NaHCO$_3$ (10 mL), and extracted three times with methylene chloride (10 mL). The organic layers were combined, dried over Na$_2$SO$_4$, filtered, and concentrated in vacuo. The residue was purified by flash column chromatography (2-15% methanol in CH$_2$Cl$_2$ with 0.1% NH$_4$OH) provided the title compound as a colorless oil. This free amine was converted to HCl salt (33 mg, 52%). LRMS (ES+) m/z for $C_{23}H_{35}N_4$ [M+H]$^+$ calc'd 367. found 367.

Example 2

2-(azetidin-3-yl)-1-(1-(cyclooctylmethyl)piperidin-4-yl)-1H-benzo[d]imidazole

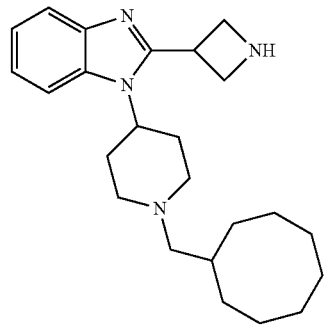 [SMILES: c1ccc2c(c1)nc(C1CNC1)n2C1CCN(CC2CCCCCCC2)CC1]

(a) 1-(cyclooctylmethyl)piperidin-4-amine

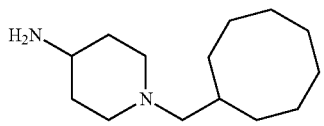 [SMILES: NC1CCN(CC2CCCCCCC2)CC1]

Sodium triacetoxyborohydride (2.60 g, 12.3 mmol) was added to a solution of cyclooctanecarbaldehyde (1.55 g, 11.1 mmol), 4-Boc-aminopiperidine (2.00 g, 10.0 mmol), and acetic acid (1.5 mL) in methylene chloride (75 mL). The resulting mixture was stirred at room temperature overnight. The solvent was removed and the residue was treated with an aqueous solution of NaHCO$_3$ and extracted with methylene chloride. The organic layers were combined, washed with brine, dried over Na$_2$SO$_4$, and concentrated to dryness. Without further purification, the residue was dissolved in methanol (10 mL) and to this solution was added 4 M HCl in dioxane (6 mL). The mixture was stirred at rt overnight. The solvent was removed and dried under vacuum overnight to afford the title compound as a hydrochloride salt (2.60 g, 88%): LRMS (ES+) m/z for C$_{14}$H$_{29}$N$_2$ [M+H]$^+$ calc'd 225. found 225.

(b) N$^1$-(1-(octan-3-yl)piperidin-4-yl)benzene-1,2-diamine

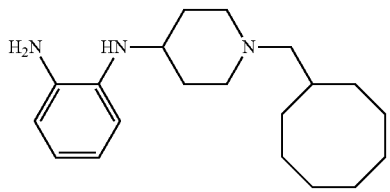 [SMILES: Nc1ccccc1NC1CCN(CC2CCCCCCC2)CC1]

To a solution of the product from Example 2a (1.10 g, 3.70 mmol) in DMF (10 mL) was added 1-fluoro-2-nitrobenzene (0.55 g, 3.9 mmol) and K$_2$CO$_3$ (1.80 g, 13.0 mmol) and the resulting suspension was stirred at 70° C. overnight. After removal of solvent by rotary evaporation, the residue was partitioned between methylene chloride (50 mL) and water (30 mL). The aqueous layer was extracted with three additional portions of methylene chloride (30 mL). The organic layers were combined, washed with brine, dried over Na$_2$SO$_4$, and concentrated to dryness. Without further purification, the residue was dissolved in ethanol (50 mL), treated with stannous chloride (4.40 g, 19.4 mmol), and the resulting mixture was stirred at 70° C. for 3 h. The solvent was removed by rotary evaporation and the residue was dissolved in methylene chloride (50 mL) and an aqueous solution of 10% NaOH (40 mL). The layers were separated and the aqueous phase was washed with two additional portions of methylene chloride (40 mL). The organic layers were combined, washed with brine, dried over Na$_2$SO$_4$, and concentrated to dryness. The residue was purified by flash column chromatography (1-9% methanol in methylene chloride with 0.1% NH$_4$OH) to afford the title compound as a purple oil: $^1$H NMR (CDCl$_3$, 400 MHz) δ 6.79 (ddd, J=8.0, 7.2, 1.6 Hz, 1H), 6.72 (dd, J=8.0, 1.6 Hz, 1H), 6.67 (d, J=7.6 Hz, 2H), 3.32 (br s, 2H), 3.24 (tt, J=10.0, 4.0 Hz, 1H), 2.81 (m, 2H), 2.08 (d, J=7.2 Hz, 2H), 2.04 (m, 4H), 1.71-1.40 (m, 16H), 1.11 (m, 2H). LRMS (ES+) m/z for C$_{20}$H$_{34}$N$_3$ [M+H]$^+$ calc'd 316. found 316.

(c) 2-(azetidin-3-yl)-1-(1-(cyclooctylmethyl)piperidin-4-yl)-1H-benzo[d]imidazole The title compound was prepared from 1-(tert-butoxycarbonyl)azetidine-3-carboxylic acid and the product from Example 2b according to the method described in Example 1d (32 mg, 72% over three steps): $^1$H NMR (DMSO-d$_6$, 400 MHz) δ 7.60 (d, J=8.0 Hz, 1H), 7.55 (d, J=8.0 Hz, 1H), 7.16 (m, 2H), 4.27 (m, 1H), 4.04 (m, 1H), 3.96 (t, J=7.2 Hz, 2H), 3.74 (d, J=7.2 Hz, 2H), 2.96 (d, J=11.6 Hz, 2H), 2.33 (m, 2H), 2.09 (m, 4H), 1.69 (m, 7H), 1.51 (9H), 1.22 (m, 2H). LRMS (ES+) m/z for C$_{24}$H$_{37}$N$_4$ [M+H]$^+$ calc'd 381. found 381.

Example 3

(R)-1-(1-(cycloheptylmethyl)piperidin-4-yl)-2-(pyrrolidin-3-yl))-1H-benzo[d]imidazole

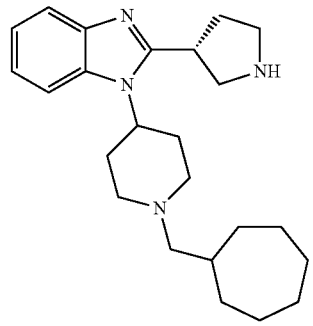 [SMILES: c1ccc2c(c1)nc([C@@H]1CCNC1)n2C1CCN(CC2CCCCCC2)CC1]

The title compound was prepared from N-Boc-β-proline and the product from Example 1c according to the method described in Example 1d (26 mg, 52% over three steps). LRMS (ES+) m/z for C$_{24}$H$_{37}$N$_4$ [M+H]$^+$ calc'd 381. found 381.

Example 4

(S)-1-(1-(cycloheptylmethyl)piperidin-4-yl)-2-(pyrrolidin-3-yl)-1H-benzo[d]imidazole

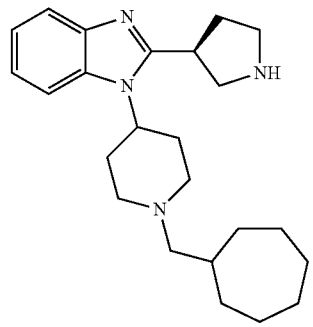 [SMILES: c1ccc2c(c1)nc([C@H]1CCNC1)n2C1CCN(CC2CCCCCC2)CC1]

The title compound was prepared using (S)—N-Boc-β-proline and the product from Example 1c and converted to HCl salt according to the procedure described in Example 1d (41 mg, 63% over three steps). LRMS (ES+) m/z for $C_{24}H_{37}N_4$ [M+H]$^+$ calc'd 381. found 381.

Example 5

(R)-1-1-(1-(cycloheptylmethyl)piperidin-4-yl)-2-(piperidin-3-yl)-1H-benzo[d]imidazole

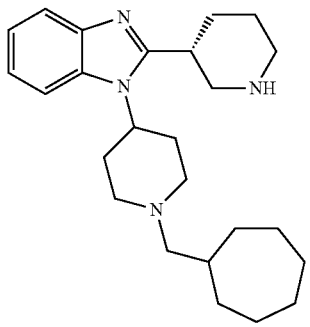 [SMILES: c1ccc2c(c1)nc([C@@H]1CCCNC1)n2C1CCN(CC2CCCCCC2)CC1]

The title compound was prepared using (R)—N-Boc-nipecotic acid and the product from Example 1c according to the procedure described in Example 1d (28 mg, 32% over three steps). LRMS (ES+) m/z for $C_{25}H_{39}N_4$ [M+H]$^+$ calc'd 395. found 395.

Example 6

(S)-1-(1-(cycloheptylmethyl)piperidin-4-yl)-2-(piperidin-3-yl)-1H-benzo[d]imidazole

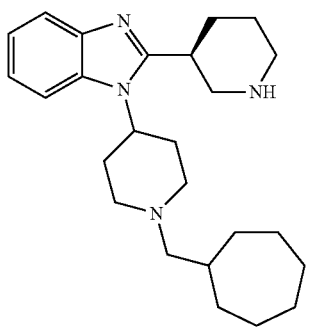 [SMILES: c1ccc2c(c1)nc([C@H]1CCCNC1)n2C1CCN(CC2CCCCCC2)CC1]

The title compound was prepared using (S)—N-Boc-nipecotic acid and the product from Example 1c and converted to HCl salt according to the procedure described in Example 1d (37 mg, 55% over three steps). LRMS (ES+) m/z for $C_{25}H_{39}N_4$ [M+H]$^+$ calc'd 395. found 395.

Example 7

1-(1-(1-(cycloheptylmethyl)piperidin-4-yl)-1H-benzo[d]imidazol-2-yl)cyclopropanamine

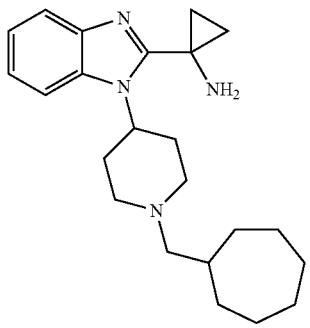 [SMILES: NC1(c2nc3ccccc3n2C2CCN(CC3CCCCCC3)CC2)CC1]

The title compound was prepared using N-Boc-1-aminocyclopropanecarboxylic acid and the product from Example 1c and converted to HCl salt according to the procedure described in Example 1d (29 mg, 25% over three steps). LRMS (ES+) m/z for $C_{23}H_{35}N_4$ [M+H]$^+$ calc'd 367. found 367.

Example 8

1-(1-(1-(cycloheptylmethyl)piperidin-4-yl)-1H-benzo[d]imidazol-2-yl)cyclopentanamine

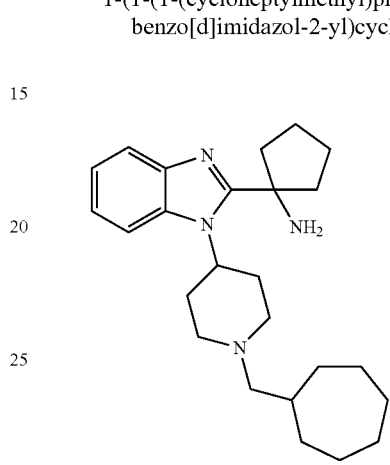

To a solution of the product from Example 1c (50 mg, 0.166 mmol) in methylene chloride (5 mL) was added N-Cbz-1-aminocyclopentanecarboxylic acid (50 mg, 0.190 mmol, prepared as described in Johnson et al, Org. Proc. Res. Dev. 1998, 2, 238), N-hydroxybenzotriazole (HOBT, 30 mg, 0.196 mmol), N-methylmorpholine (0.04 mL, 0.364 mmol), 4-dimethylaminopyridine (5 mg), and 1-ethyl-3-(3'-dimethylaminopropyl)carbodiimide hydrochloride (EDC, 64 mg, 0.335 mmol). The resulting mixture was stirred at room temperature for 36 h. After removal of solvent by rotary evaporation, the residue was dissolved in methylene chloride (10 mL) and washed with a saturated aqueous solution of NaHCO$_3$ (10 mL). The aqueous layer was extracted twice with additional methylene chloride (5 mL) and the combined organic layers were dried over Na$_2$SO$_4$, filtered, and concentrated in vacuo. Without further purification, the residue was dissolved in acetic acid (1.5 mL) and stirred at 100° C. for 72 h. The solution was cooled, concentrated, and partitioned between a saturated aqueous solution of NaHCO$_3$ (10 mL) and methylene chloride (10 mL). The layers were separated, and the aqueous layer was extracted with two additional portions of methylene chloride (10 mL). The organic layers were combined, dried over Na$_2$SO$_4$, filtered, concentrated in vacuo, and purified by flash column chromatography (5 to 60% ethyl acetate in hexanes). The obtained oil was dissolved in ethyl acetate (5 mL). To this solution was added 10% palladium on carbon (0.25 g) and the reaction was stirred under a hydrogen atmosphere using a balloon filled with hydrogen gas for 12 h at room temperature. After removal of catalyst by filtration through a pad of Celite™, the filtrate was concentrated in vacuo. The residue was purified by flash column chromatography (0.4-5% methanol in CH$_2$Cl$_2$ with 0.1% NH$_4$OH) and converted to HCl salt to provide the title compound as a colorless solid (9.7 mg, 12%). LRMS (ES+) m/z for $C_{25}H_{39}N_4$ [M+H]$^+$ calc'd 395. found 395.

Example 9

1-(1-(1-(cycloheptylmethyl)piperidin-4-yl)-1H-benzo[d]imidazol-2-yl)cyclohexanamine

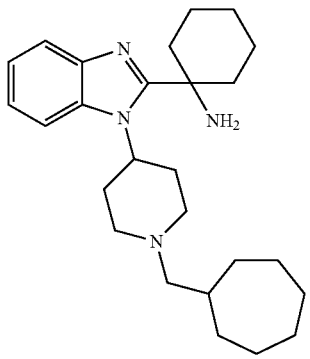 [SMILES: NC1(c2nc3ccccc3n2C2CCN(CC3CCCCCC3)CC2)CCCCC1]

The title compound was prepared using N-Cbz-1-aminocyclohexanecarboxylic acid and the product from Example 1c according to the procedure described in Example 8 (19 mg, 7% over three steps). LRMS (ES+) m/z for $C_{26}H_{41}N_4$ [M+H]$^+$ calc'd 409. found 409.

Example 10

1-(1-(cyclooctylmethyl)piperidin-4-yl)-2-(piperidin-4-yl)-1H-benzo[d]imidazole

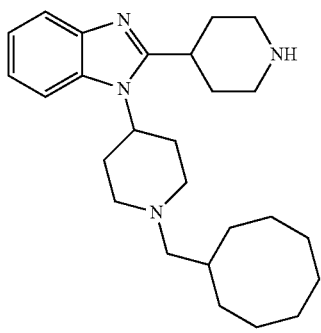 [SMILES: c1ccc2c(c1)nc(C1CCNCC1)n2C1CCN(CC2CCCCCCC2)CC1]

The title compound was prepared using N-Boc-isonipecotic acid and the product from Example 2b according to the procedure described in Example 1d (4 mg, 15% over three steps). LRMS (ES+) m/z for $C_{26}H_{41}N_4$ [M+H]$^+$ calc'd 409. found 409.

Example 11

(R)-1-1-(1-(cyclooctylmethyl)piperidin-4-yl)-2-(pyrrolidin-3-yl)-1H-benzo[d]imidazole

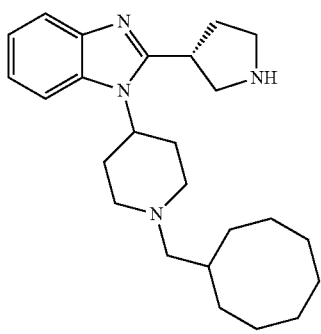 [SMILES: c1ccc2c(c1)nc([C@@H]1CCNC1)n2C1CCN(CC2CCCCCCC2)CC1]

The title compound was prepared using (R)—N-Boc-β-proline and the product from Example 2b according to the procedure described in Example 1d (710 mg, 78% over three steps). LRMS (ES+) m/z for $C_{26}H_{39}N_4$ [M+H]$^+$ calc'd 395. found 395.

Example 12

(S)-1-(1-(cyclooctylmethyl)piperidin-4-yl)-2-(pyrrolidin-3-yl)-1H-benzo[d]imidazole

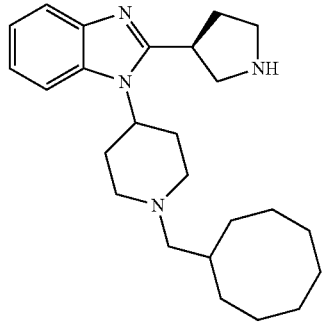 [SMILES: c1ccc2c(c1)nc([C@H]1CCNC1)n2C1CCN(CC2CCCCCCC2)CC1]

The title compound was prepared using (S)—N-Boc-β-proline and the product from Example 2b according to the procedure described in Example 1d (28 mg, 68% over three steps). LRMS (ES+) m/z for $C_{26}H_{39}N_4$ [M+H]$^+$ calc'd 395. found 395.

Example 13

(S)-1-1-(1-(cyclooctylmethyl)piperidin-4-yl)-2-(pyrrolidin-2-yl)-1H-benzo[d]imidazole

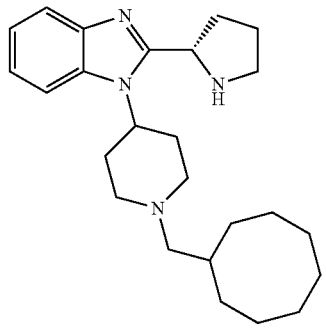 [SMILES: c1ccc2c(c1)nc([C@@H]1CCCN1)n2C1CCN(CC2CCCCCCC2)CC1]

The title compound was prepared using (S)—N-Boc-proline and the product from Example 2b according to the procedure described in Example 1d (7 mg, 14% over three steps). LRMS (ES+) m/z for $C_{26}H_{39}N_4$ [M+H]$^+$ calc'd 395. found 395.

Example 14

(R)-1-1-(1-(cyclooctylmethyl)piperidin-4-yl)-2-(piperidin-3-yl)-1H-benzo[d]imidazole

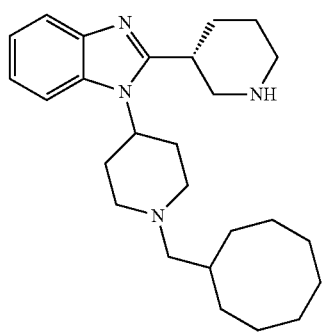 [SMILES: c1ccc2c(c1)nc([C@@H]1CCCNC1)n2C1CCN(CC2CCCCCCC2)CC1]

The title compound was prepared using (R)—N-Boc-nipecotic acid and the product from Example 2b according to the procedure described in Example 1d (18 mg, 45% over three steps). LRMS (ES+) m/z for $C_{26}H_{41}N_4$ [M+H]$^+$ calc'd 409. found 409.

Example 15

2-(1-(1-(cyclooctylmethyl)piperidin-4-yl)-1H-benzo[d]imidazol-2-yl)ethanamine

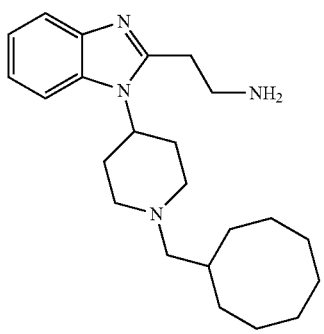 [SMILES: NCCc1nc2ccccc2n1C1CCN(CC2CCCCCCC2)CC1]

The title compound was prepared using N-Boc-β-alanine and the product from Example 2b according to the procedure described in Example 1d (37 mg, 85% over three steps). LRMS (ES+) m/z for $C_{23}H_{37}N_4$ [M+H]$^+$ calc'd 369. found 369.

Example 16

3-(1-(1-(cyclooctylmethyl)piperidin-4-yl)-1H-benzo[d]imidazol-2-yl)propan-1-amine

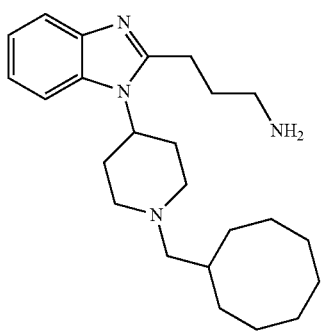 [SMILES: NCCCc1nc2ccccc2n1C1CCN(CC2CCCCCCC2)CC1]

The title compound was prepared using N-Boc-γ-aminobutyric acid and the product from Example 2b according to the procedure described in Example 1d (14 mg, 22% over three steps). LRMS (ES+) m/z for $C_{24}H_{39}N_4$ [M+H]$^+$ calc'd 383. found 383.

Example 17

(R)-1-4-(1-(1-(cyclooctylmethyl)piperidin-4-yl)-1H-benzo[d]imidazol-2-yl)thiazolidine

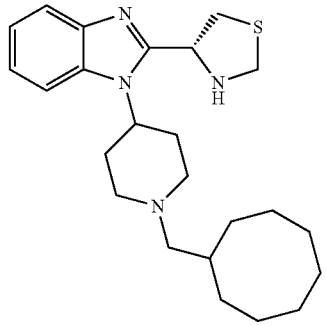 [SMILES: c1ccc2c(c1)nc([C@@H]1CSCN1)n2C1CCN(CC2CCCCCCC2)CC1]

The title compound was prepared using N-Boc-(R)-thiazolidine-4-carboxylic acid and the product from Example 2b according to the procedure described in Example 1d (12 mg, 23% over three steps). LRMS (ES+) m/z for $C_{24}H_{37}N_4S$ [M+H]$^+$ calc'd 413. found 413.

Example 18

(3R,5S)-5-(1-(1-(cyclooctylmethyl)piperidin-4-yl)-1H-benzo[d]imidazol-2-yl)pyrrolidin-3-ol

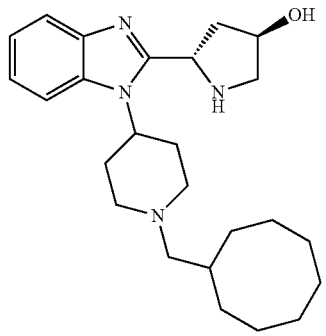 [SMILES: O[C@H]1CN[C@H](c2nc3ccccc3n2C2CCN(CC3CCCCCCC3)CC2)C1]

The title compound was prepared using N-Boc-(2S,4R)-4-hydroxypyrrolidine-2-carboxylic acid and the product from Example 2b according to the procedure described in Example 1d (12 mg, 28% over three steps). LRMS (ES+) m/z for $C_{25}H_{39}N_4O$ [M+H]$^+$ calc'd 411. found 411.

Example 19

1-(1-(1-(cyclooctylmethyl)piperidin-4-yl)-1H-benzo[d]imidazol-2-yl)cyclopentanamine

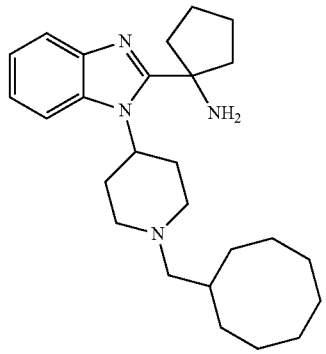 [SMILES: NC1(c2nc3ccccc3n2C2CCN(CC3CCCCCCC3)CC2)CCCC1]

The title compound was prepared using N-Cbz-1-amino-cyclopentanecarboxyic acid and the product from Example 2b and converted to HCl salt according to the procedure described in Example 8 (200 mg, 24% over three steps). LRMS (ES+) m/z for $C_{26}H_{41}N_4$ [M+H]$^+$ calc'd 409. found 409.

Example 20

1-(1-(1-(cyclooctylmethyl)piperidin-4-yl)-1H-benzo[d]imidazol-2-yl)cyclohexanamine

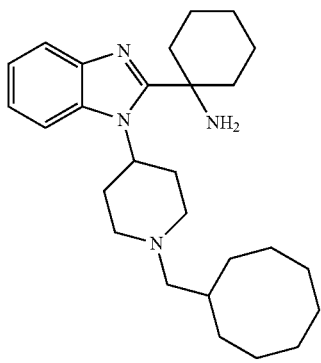 [SMILES: NC1(c2nc3ccccc3n2C2CCN(CC3CCCCCCC3)CC2)CCCCC1]

The title compound was prepared using N-Cbz-1-amino-cyclohexanecarboxyic acid and the product from Example 2b according to the procedure described in Example 8 (11 mg, 5% over three steps). LRMS (ES+) m/z for $C_{27}H_{43}N_4$ [M+H]$^+$ calc'd 423. found 423.

Example 21

1-(1-(((1S,2R,5S)-6,6-dimethylbicyclo[3.1.1]heptan-2-yl)methyl)piperidin-4-yl)-2-((R)-pyrrolidin-3-yl)-1H-benzo[d]imidazole

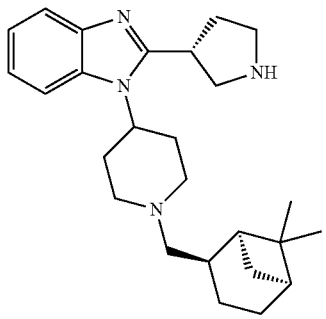 [SMILES: CC1(C)[C@H]2CC[C@@H](CN3CCC(n4c([C@@H]5CCNC5)nc5ccccc54)CC3)[C@@H]1C2]

(a) 1-(((1R,3S,5S)-6,6-dimethylbicyclo[3.1.1]heptan-3-yl)methyl)piperidin-4-one

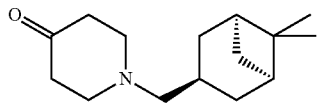 [SMILES: CC1(C)[C@@H]2C[C@H](CN3CCC(=O)CC3)C[C@H]1C2]

The title compound was prepared according to the procedure described in Example 1b (2.14 g, 74%). LRMS (ES+) m/z for $C_{15}H_{26}NO$ [M+H]$^+$ calc'd 236. found 236.

(b) N$^1$-(1-(((1R,3S,5S)-6,6-dimethylbicyclo[3.1.1]heptan-3-yl)methyl)piperidin-4-yl)benzene-1,2-diamine

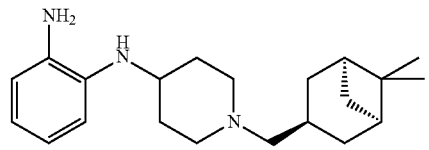 [SMILES: CC1(C)[C@@H]2C[C@H](CN3CCC(Nc4ccccc4N)CC3)C[C@H]1C2]

The title compound was prepared using the product from Example 23a according to the procedure described in Example 1c (0.48 g, 95%). LRMS (ES+) m/z for $C_{21}H_{34}N_3$ [M+H]$^+$ calc'd 328. found 328.

(c) 1-(1-(((1S,2R,5S)-6,6-dimethylbicyclo[3.1.1]heptan-2-yl)methyl)piperidin-4-yl)-2-((R)-pyrrolidin-3-yl)-1H-benzo[c]imidazole The title compound was prepared using (R)—N-Boc-β-proline and the product from Example 21b according to the procedure described in Example 1d (31 mg, 58% over three steps). LRMS (ES+) m/z for $C_{26}H_{39}N_4$ [M+H]$^+$ calc'd 407. found 407.

Example 22

1-(1-(((1S,2R,5S)-6,6-dimethylbicyclo[3.1.1]heptan-2-yl)methyl)piperidin-4-yl)-2-((S)-piperidin-3-yl)-1H-benzo[d]imidazole

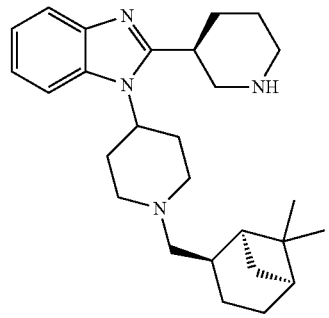 [SMILES: CC1(C)[C@H]2CC[C@@H](CN3CCC(n4c([C@H]5CCCNC5)nc5ccccc54)CC3)[C@@H]1C2]

The title compound was prepared using (S)—N-Boc-nipecotic acid and the product from Example 21b according to the procedure described in Example 1d (28 mg, 45% over three steps). LRMS (ES+) m/z for $C_{27}H_{41}N_4$ [M+H]$^+$ calc'd 421. found 421.

Example 23

1-(1-(((1S,2R,5S)-6,6-dimethylbicyclo[3.1.1]heptan-2-yl)methyl)piperidin-4-yl)-2-((S)-pyrrolidin-3-yl)-1H-benzo[d]imidazole

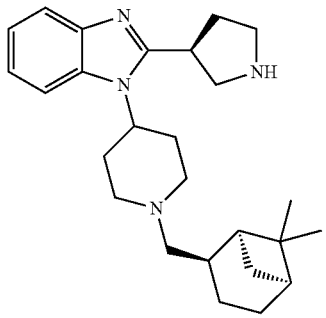 [SMILES: CC1(C)[C@H]2CC[C@@H](CN3CCC(n4c([C@H]5CCNC5)nc5ccccc54)CC3)[C@@H]1C2]

The title compound was prepared using (S)—N-Boc-β-proline and the product from Example 21b according to the procedure described in Example 1d (28 mg, 53% over three steps). LRMS (ES+) m/z for $C_{26}H_{39}N_4$ [M+H]$^+$ calc'd 407. found 407.

Example 24

1-(1-(((1S,2R,5S)-6,6-dimethylbicyclo[3.1.1]heptan-2-yl)methyl)piperidin-4-yl)-2-((R)-piperidin-3-yl)-1H-benzo[d]imidazole

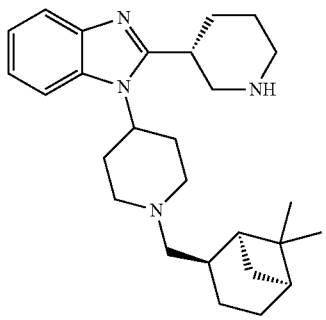 [SMILES: CC1(C)[C@H]2CC[C@@H](CN3CCC(n4c([C@@H]5CCCNC5)nc5ccccc54)CC3)[C@@H]1C2]

The title compound was prepared using (R)—N-Boc-nipecotic acid and the product from Example 21b according to the procedure described in Example 1d (27 mg, 49% over three steps). LRMS (ES+) m/z for $C_{27}H_{41}N_4$ [M+H]$^+$ calc'd 421. found 421.

Example 25

1-(1-(1-(((1S,2R,5S)-6,6-dimethylbicyclo[3.1.1]heptan-2-yl)methyl)piperidin-4-yl)-1H-benzo[d]imidazol-2-yl)cyclopentanamine

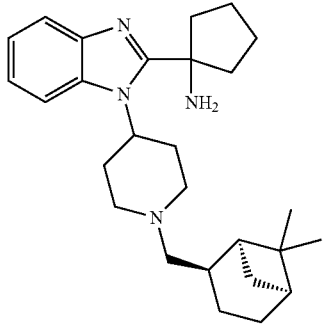 [SMILES: CC1(C)[C@H]2CC[C@@H](CN3CCC(n4c(C5(N)CCCC5)nc5ccccc54)CC3)[C@@H]1C2]

The title compound was prepared using N-Cbz-1-aminocyclopentanecarboxlyic acid and the product from Example 21b and converted to HCl salt according to the procedure described in Example 8 (14 mg, 23% over three steps). LRMS (ES+) m/z for $C_{27}H_{41}N_4$ [M+H]$^+$ calc'd 421. found 421.

Example 26

1-(1-(((1S,2R,5S)-6,6-dimethylbicyclo[3.1.1]heptan-2-yl)methyl)piperidin-4-yl)-5-fluoro-2-((R)-pyrrolidin-3-yl)-1H-benzo[d]imidazole

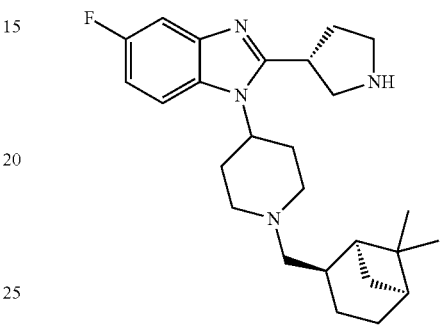

(a) 1-(((1R,3S,5S)-6,6-dimethylbicyclo[3.1.1]heptan-3-yl)methyl)piperidin-4-amine

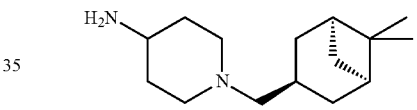

To a solution of the product from Example 21a (0.60 g, 2.55 mmol) and ammonium acetate (1.96 g, 25.5 mmol) in methanol (30 mL) was added sodium cyanoborohydride (0.24 g, 3.8 mmol). The reaction mixture was stirred at rt for 72 h, and the solvent was removed in vacuo. The residue was partitioned between methylene chloride (50 mL) and a saturated solution of sodium bicarbonate, and the aqueous layer was further extracted with methylene chloride (2×25 mL). The organic layers were combined, washed with brine, dried over sodium sulfate, and concentrated by rotary evaporation to afford the title compound as colorless oil (0.50 g, 84%). LRMS (ES+) m/z for $C_{15}H_{29}N_2$ [M+H]$^+$ calc'd 237. found 237.

(b) $N^1$-(1-(((1R,3S,5S)-6,6-dimethylbicyclo[3.1.1]heptan-3-yl)methyl)piperidin-4-yl)-4-fluorobenzene-1,2-diamine

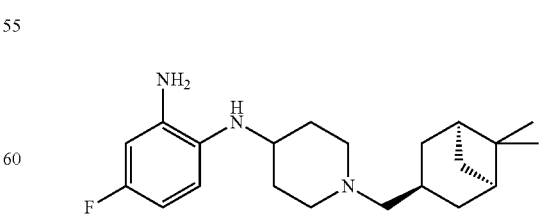

The title compound was prepared using the product from Example 26a and 2,5-difluoronitrobenzene according to the procedure described in Example 2b (0.33 g, 52%). LRMS (ES+) m/z for $C_{21}H_{33}FN_3$ [M+H]$^+$ calc'd 346. found 346.

(c) 1-(1-(((1S,2R,5S)-6,6-dimethylbicyclo[3.1.1]
heptan-2-yl)methyl)piperidin-4-yl)-5-fluoro-2-((R)-
pyrrolidin-3-yl)-1H-benzo[d]imidazole

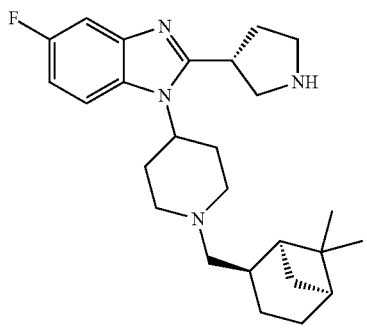

The title compound was prepared using (R)—N-Boc-β-proline and the product from Example 26b according to the procedure described in Example 1d (23 mg, 42% over three steps). LRMS (ES+) m/z for $C_{26}H_{38}FN_4$ [M+H]$^+$ calc'd 425. found 425.

Example 27

1-(1-(((1S,2R,5S)-6,6-dimethylbicyclo[3.1.1]heptan-2-yl)methyl)piperidin-4-yl)-5-fluoro-2-((R)-piperidin-3-yl)-1H-benzo[d]imidazole

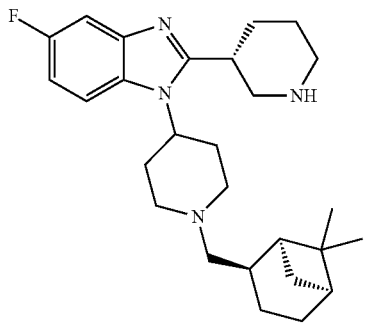

The title compound was prepared using (R)—N-Boc-nipecotic acid and the product from Example 26b according to the procedure described in Example 1d (18 mg, 31% over three steps). LRMS (ES+) m/z for $C_{27}H_{40}FN_4$ [M+H]$^+$ calc'd 439. found 439.

Example 28

(R)-2-(pyrrolidin-3-yl)-1-(1-((tetrahydro-2H-pyran-4-yl)methyl)piperidin-4-yl)-1H-benzo[d]imidazole

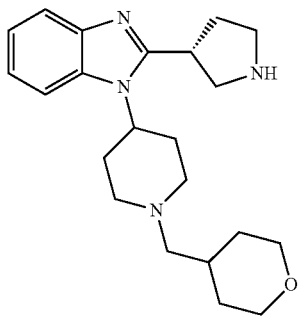 [SMILES: c1ccc2c(c1)nc([C@@H]1CCNC1)n2C1CCN(CC2CCOCC2)CC1]

(a) 1-((tetrahydro-2H-pyran-4-yl)methyl)piperidin-4-one

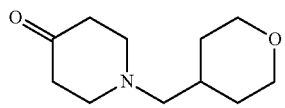 [SMILES: O=C1CCN(CC2CCOCC2)CC1]

The title compound was prepared according to the procedure described in Example 1b (0.34 g, 70%). LRMS (ES+) m/z for $C_{15}H_{26}NO$ [M+H]$^+$ calc'd 198. found 198.

(b) N$^1$-(1-((tetrahydro-2H-pyran-4-yl)methyl)piperidin-4-yl)benzene-1,2-diamine

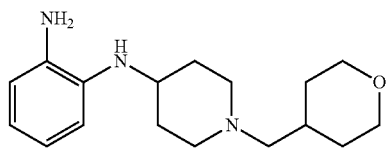 [SMILES: Nc1ccccc1NC1CCN(CC2CCOCC2)CC1]

The title compound was prepared using the product from Example 30a according to the procedure described in Example 1c (2.14 g, 74%). LRMS (ES+) m/z for $C_{17}H_{28}N_3O$ [M+H]$^+$ calc'd 290. found 290.

(c) (R)-2-(pyrrolidin-3-yl)-1-(1-((tetrahydro-2H-pyran-4-yl)methyl)piperidin-4-yl)-1H-benzo[d]imidazole The title compound was prepared using (R)—N-Boc-β-proline and the product from Example 30b and converted to HCl salt according to the procedure described in Example 1d (29 mg, 44% over three steps). LRMS (ES+) m/z for $C_{22}H_{33}N_4O$ [M+H]$^+$ calc'd 369. found 369.

Example 29

(R)-1-(1-(cyclooctylmethyl)piperidin-4-yl)-5-fluoro-2-(pyrrolidin-3-yl)-1H-benzo[d]imidazole

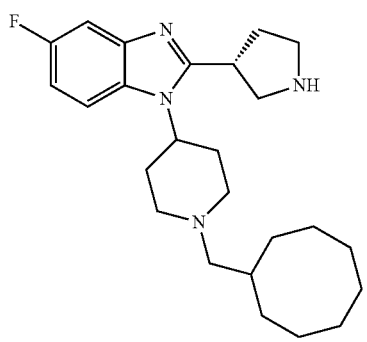 [SMILES: Fc1ccc2c(c1)nc([C@@H]1CCNC1)n2C1CCN(CC2CCCCCCC2)CC1]

(a) N¹-(1-(cyclooctylmethyl)piperidin-4-yl)-4-fluorobenzene-1,2-diamine

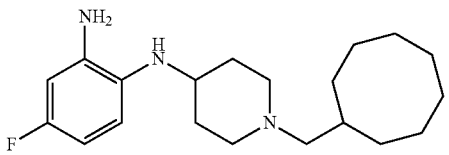 [SMILES: Nc1cc(F)ccc1NC1CCN(CC2CCCCCCC2)CC1]

The title compound was prepared using the product from Example 2a and 2,5-difluoronitrobenzene according to the procedure described in Example 2b (0.67 g, 79%): ¹H NMR (CDCl$_3$, 400 MHz) δ 6.61 (dd, J=8.4, 5.2 Hz, 1H), 6.43 (m, 2H), 3.61 (br s, 2H), 3.10 (m, 1H), 2.80 (m, 2H), 2.02 (m, 6H), 1.68 (6H), 1.59-1.43 (m, 10H), 1.21 (m, 2H). LRMS (ES+) m/z for C$_{20}$H$_{33}$FN$_3$ [M+H]$^+$ calc'd 334. found 334.

(b) (R)-1-(1-(cyclooctylmethyl)piperidin-4-yl)-5-fluoro-2-(pyrrolidin-3-yl)-1H-benzo[d]imidazole The title compound was prepared using (R)—N-Boc-β-proline and the product from Example 29a according to the procedure described in Example 1d (26 mg, 47% over three steps). LRMS (ES+) m/z for C$_{25}$H$_{38}$FN$_4$ [M+H]$^+$ calc'd 413. found 413.

Example 30

(R)-1-(1-(cyclooctylmethyl)piperidin-4-yl)-5-fluoro-2-(piperidin-3-yl)-1H-benzo[d]imidazole

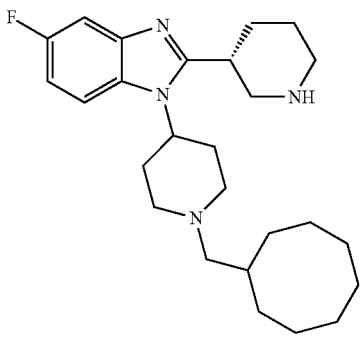 [SMILES: Fc1ccc2c(c1)nc([C@@H]1CCCNC1)n2C1CCN(CC2CCCCCCC2)CC1]

The title compound was prepared using (R)—N-Boc-nipecotic acid and the product from Example 29a according to the procedure described in Example 1d (25 mg, 48% over three steps). LRMS (ES+) m/z for C$_{26}$H$_{40}$FN$_4$ [M+H]$^+$ calc'd 427. found 427.

Example 31

2-(1-(1-(cyclooctylmethyl)piperidin-4-yl)-5-fluoro-1H-benzo[d]imidazol-2-yl)ethanamine

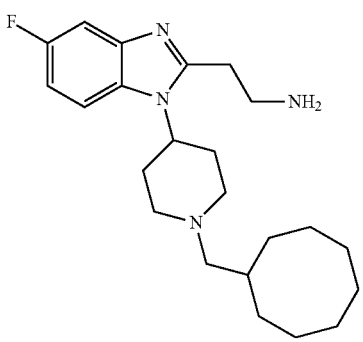 [SMILES: NCCc1nc2cc(F)ccc2n1C1CCN(CC2CCCCCCC2)CC1]

The title compound was prepared using N-Boc-β-alanine and the product from Example 29a according to the procedure described in Example 1d (29 mg, 60% over three steps). LRMS (ES+) m/z for C$_{23}$H$_{36}$FN$_4$ [M+H]$^+$ calc'd 387. found 387.

Example 32

2-(azetidin-3-yl)-1-(1-(cyclooctylmethyl)piperidin-4-yl)-5-fluoro-1H-benzo[d]imidazole

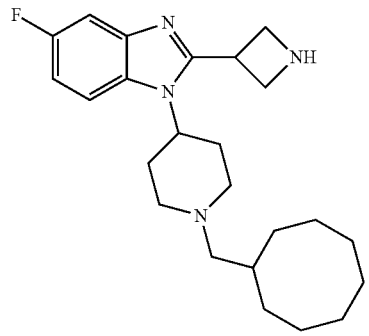 [SMILES: Fc1ccc2c(c1)nc(C1CNC1)n2C1CCN(CC2CCCCCCC2)CC1]

The title compound was prepared using N-Boc-azetidine-3-carboxylic acid and the product from Example 29a according to the procedure described in Example 1d (33 mg, 67% over three steps). LRMS (ES+) m/z for C$_{24}$H$_{36}$FN$_4$ [M+H]$^+$ calc'd 399. found 399.

Example 33

(3R,5S)-5-(1-(1-(cyclooctylmethyl)piperidin-4-yl)-5-fluoro-1H-benzo[d]imidazol-2-yl)pyrrolidin-3-ol

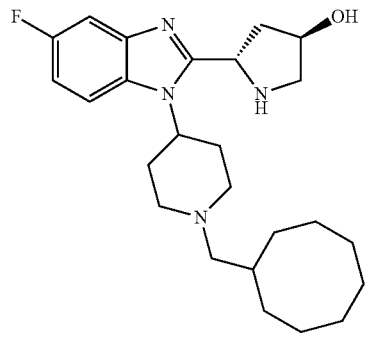 [SMILES: O[C@H]1CN[C@H](c2nc3cc(F)ccc3n2C2CCN(CC3CCCCCCC3)CC2)C1]

The title compound was prepared using N-Boc-(2S,4R)-4-hydroxypyrrolidine-2-carboxylic acid and the product from Example 29a according to the procedure described in Example 1d (8 mg, 14% over three steps). LRMS (ES+) m/z for C$_{25}$H$_{38}$FN$_4$O [M+H]$^+$ calc'd 429. found 429.

Example 34

(S)-1-(1-(cyclooctylmethyl)piperidin-4-yl)-5-fluoro-2-(pyrrolidin-3-yl)-1H-benzo[d]imidazole

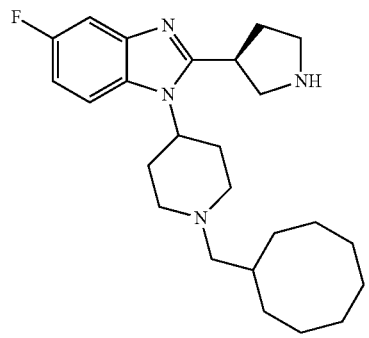 [SMILES: Fc1ccc2c(c1)nc([C@H]1CCNC1)n2C1CCN(CC2CCCCCCC2)CC1]

The title compound was prepared using (S)—N-Boc-β-proline and the product from Example 29a according to the procedure described in Example 1d (44 mg, 84% over three steps). LRMS (ES+) m/z for $C_{25}H_{38}FN_4$ [M+H]$^+$ calc'd 413. found 413.

Example 35

(R)-1-(1-(cyclooctylmethyl)piperidin-4-yl)-4-fluoro-2-(pyrrolidin-3-yl)-1H-benzo[d]imidazole (a) $N^1$-(1-(cyclooctylmethyl)piperidin-4-yl)-3-fluorobenzene-1,2-diamine

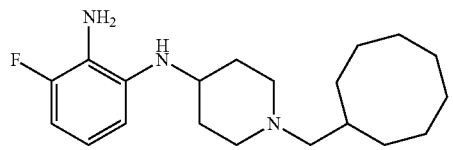 [SMILES: Nc1c(F)cccc1NC1CCN(CC2CCCCCCC2)CC1]

The title compound was prepared using the product from Example 2a and 2,6-difluoronitrobenzene according to the procedure described in Example 2b (0.230 g, 41%): $^1$H NMR (CDCl$_3$, 400 MHz) δ 6.72 (td, J=8.0, 6.0 Hz, 1H), 6.49 (ddd, J=9.6, 8.4, 1.2 Hz, 1H), 6.43 (d, J=8.0 Hz, 1H), 3.25 (m, J=3H), 2.81 (m, 2H), 2.05 (m, 6H), 1.71-1.41 (m, 16H), 1.21 (m, 2H). LRMS (ES+) m/z for $C_{20}H_{33}FN_3$ [M+H]$^+$ calc'd 334. found 334.

(b) 1-(1-(cyclooctylmethyl)piperidin-4-yl)-4-fluoro-2-(pyrrolidin-3-yl)-1H-benzo[d]imidazole The title compound was prepared using N-Boc-β-proline and the product from Example 35a and converted to HCl salt according to the procedure described in Example 1d (23 mg, 37% over three steps). LRMS (ES+) m/z for $C_{25}H_{38}FN_4$ [M+H]$^+$ calc'd 413. found 413.

Example 36

2-(azetidin-3-yl)-1-(1-(cyclooctylmethyl)piperidin-4-yl)-6-fluoro-1H-benzo[d]imidazole

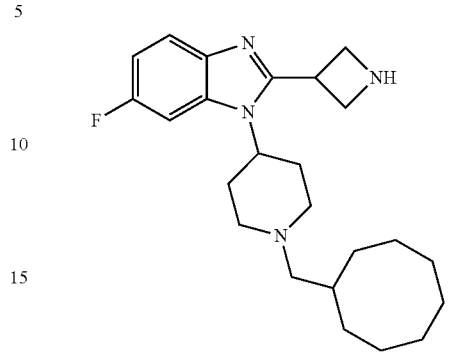

(a) $N^1$-(1-(cyclooctylmethyl)piperidin-4-yl)-5-fluorobenzene-1,2-diamine

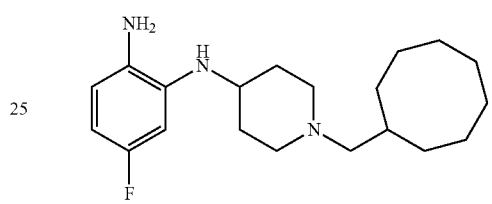

The title compound was prepared using the product from Example 2a and 2,4-difluoronitrobenzene according to the procedure described in Example 2b (0.16 g, 28%): $^1$H NMR (CDCl$_3$, 400 MHz) δ 6.63 (dd, J=8.4, 5.6 Hz, 1H), 6.35 (dd, J=11.2, 2.8 Hz, 1H), 6.29 (td, J=8.4, 2.8 Hz, 1H), 3.20 (tt, J=10.0, 4.0 Hz, 1H), 2.82 (m, 2H), 2.06 (m, 6H), 1.71-1.41 (m, 16H), 1.21 (m, 2H). LRMS (ES+) m/z for $C_{20}H_{33}FN_3$ [M+H]$^+$ calc'd 334. found 334.

(b) 2-(azetidin-3-yl)-1-(1-(cyclooctylmethyl)piperidin-4-yl)-6-fluoro-1H-benzo[d]imidazole The title compound was prepared using N-Boc-azetidine-3-carboxylic acid and the product from Example 36a and converted to HCl salt according to the procedure described in Example 1d (33 mg, 52% over three steps). LRMS (ES+) m/z for $C_{24}H_{36}FN_4$ [M+H]$^+$ calc'd 399. found 399.

Example 37

(R)-1-(1-(cyclooctylmethyl)piperidin-4-yl)-6-fluoro-2-(pyrrolidin-3-yl)-1H-benzo[d]imidazole

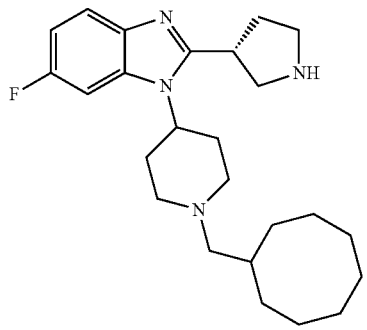 [SMILES: Fc1ccc2nc([C@@H]3CCNC3)n(C3CCN(CC4CCCCCCC4)CC3)c2c1]

The title compound was prepared using (R)—N-Boc-β-proline and the product from Example 36a according to the procedure described in Example 1d (23 mg, 46% over three steps). LRMS (ES+) m/z for $C_{25}H_{38}FN_4$ [M+H]$^+$ calc'd 413. found 413.

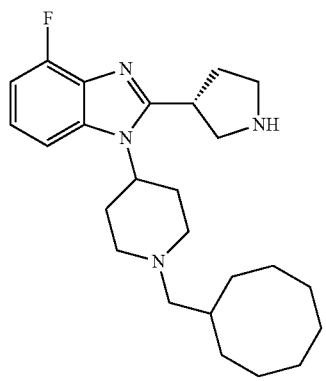

Example 38

(S)-1-(1-(cyclooctylmethyl)piperidin-4-yl)-6-fluoro-2-(pyrrolidin-3-yl)-1H-benzo[d]imidazole

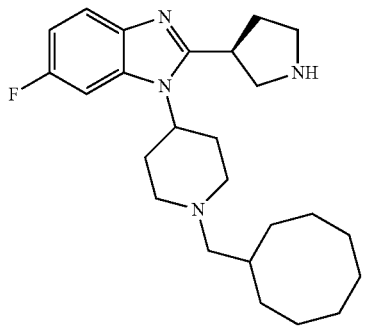 [SMILES: Fc1ccc2nc([C@H]3CCNC3)n(C3CCN(CC4CCCCCCC4)CC3)c2c1]

The title compound was prepared using (S)—N-Boc-β-proline and the product from Example 36a and converted to HCl salt according to the procedure described in Example 1d (11 mg, 18% over three steps). LRMS (ES+) m/z for $C_{25}H_{38}FN_4$ [M+H]$^+$ calc'd 413. found 413.

Example 39

2-(azetidin-3-yl)-1-(1-(cyclooctylmethyl)piperidin-4-yl)-6,7-difluoro-1H-benzo[d]imidazole

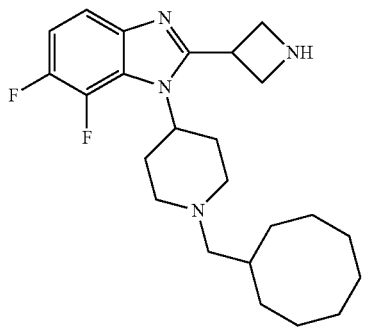 [SMILES: Fc1ccc2nc(C3CNC3)n(C3CCN(CC4CCCCCCC4)CC3)c2c1F]

(a) N$^1$-(1-(cyclooctylmethyl)piperidin-4-yl)-5,6-difluorobenzene-1,2-diamine

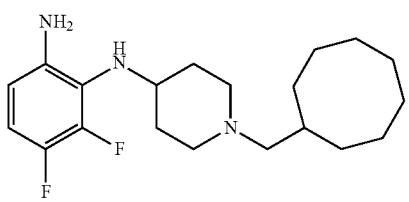 [SMILES: Nc1ccc(F)c(F)c1NC1CCN(CC2CCCCCCC2)CC1]

The title compound was prepared using the product from Example 2a and 2,3,4-trifluoronitrobenzene according to the procedure described in Example 2b (0.23 g, 42%): $^1$H NMR (CDCl$_3$, 400 MHz) δ 6.65 (ddd, J=9.6, 8.8, 8.8 Hz, 1H), 6.37 (ddd, J=8.8, 4.4, 2.0 Hz, 1H), 3.68 (br s, 2H), 3.00 (tt, J=10.4, 6.0 Hz, 1H), 2.82 (m, 2H), 2.06 (d, J=7.2 Hz, 2H), 1.95 (t, J=11.6 Hz, 2H), 1.87 (d, J=12.4 Hz, 2H), 1.68-1.40 (m, 16H), 1.21 (m, 2H). LRMS (ES+) m/z for $C_{20}H_{32}F_2N_3$ [M+H]$^+$ calc'd 352. found 352.

(b) 2-(azetidin-3-yl)-1-(1-(cyclooctylmethyl)piperidin-4-yl)-6,7-difluoro-1H-benzo[d]imidazole The title compound was prepared using N-Boc-azetidine-3-carboxylic acid and the product from Example 39a according to the procedure described in Example 1d (30 mg, 61% over three steps). LRMS (ES+) m/z for $C_{24}H_{35}F_2N_4$ [M+H]$^+$ calc'd 417. found 417.

Example 40

(R)-1-(1-(cyclooctylmethyl)piperidin-4-yl)-6,7-difluoro-2-(pyrrolidin-3-yl)-1H-benzo[d]imidazole

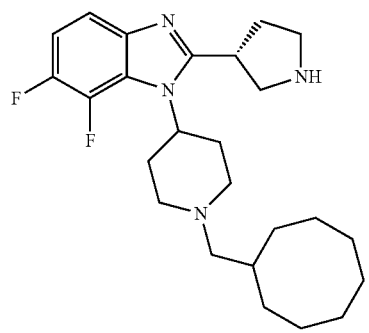 [SMILES: Fc1ccc2nc([C@@H]3CCNC3)n(C3CCN(CC4CCCCCCC4)CC3)c2c1F]

The title compound was prepared using (R)—N-Boc-β-proline and the product from Example 39a according to the procedure described in Example 1d (15 mg, 31% over three steps). LRMS (ES+) m/z for $C_{25}H_{37}F_2N_4$ [M+H]$^+$ calc'd 431. found 431.

Example 41

(R)-1-(1-(cyclooctylmethyl)piperidin-4-yl)-5-methyl-2-(pyrrolidin-3-yl)-1H-benzo[d]imidazole

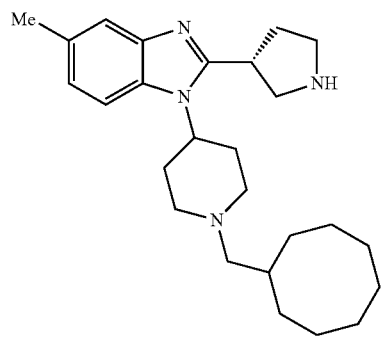 [SMILES: Cc1ccc2c(c1)nc([C@@H]1CCNC1)n2C1CCN(CC2CCCCCCC2)CC1]

(a) N¹-(1-(cyclooctylmethyl)piperidin-4-yl)-4-methylbenzene-1,2-diamine

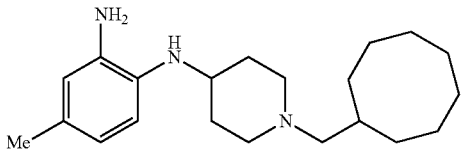 [SMILES: Cc1ccc(NC2CCN(CC3CCCCCCC3)CC2)c(N)c1]

The title compound was prepared using the product from Example 2a and 1-fluoro-4-methyl-2-nitrobenzene according to the procedure described in Example 2b (0.11 g, 28%): $^1$H NMR (CDCl$_3$, 400 MHz) δ 6.58 (s, 1H), 6.57 (d, J=8.8 Hz, 2H), 3.36 (br s, 2H), 3.18 (m, 1H), 2.79 (m, 2H), 2.21 (s, 3H), 2.03 (m, 6H), 1.69-1.45 (m, 16H), 1.22 (m, 2H). LRMS (ES+) m/z for C$_{21}$H$_{36}$N$_3$ [M+H]$^+$ calc'd 330. found 330.

(b) (R)-1-(1-(cyclooctylmethyl)piperidin-4-yl)-5-methyl-2-(pyrrolidin-3-yl)-1H-benzo[d]imidazole The title compound was prepared using N-Boc-β-proline and the product from Example 41a according to the procedure described in Example 1d (42 mg, 90% over three steps). LRMS (ES+) m/z for C$_{26}$H$_{41}$N$_4$ [M+H]$^+$ calc'd 409. found 409.

Example 42

(R)-1-(1-(cyclooctylmethyl)piperidin-4-yl)-5-methyl-2-(piperidin-3-yl)-1H-benzo[d]imidazole

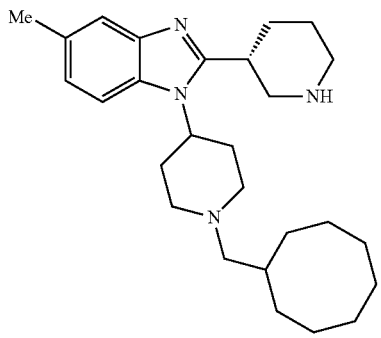 [SMILES: Cc1ccc2c(c1)nc([C@@H]1CCCNC1)n2C1CCN(CC2CCCCCCC2)CC1]

The title compound was prepared using (R)—N-Boc-nipecotic acid and the product from Example 41a according to the procedure described in Example 1d (29 mg, 59% over three steps). LRMS (ES+) m/z for C$_{27}$H$_{43}$N$_4$ [M+H]$^+$ calc'd 423. found 423.

Example 43

2-(azetidin-3-yl)-1-(1-(cyclooctylmethyl)piperidin-4-yl)-5-(methylsulfonyl)-1H-benzo[d]imidazole

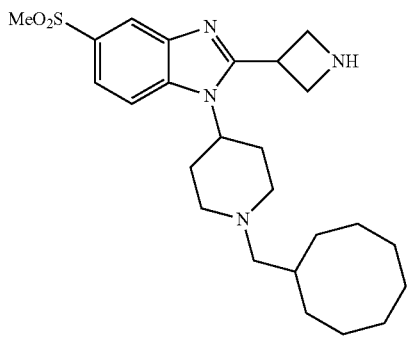 [SMILES: CS(=O)(=O)c1ccc2c(c1)nc(C1CNC1)n2C1CCN(CC2CCCCCCC2)CC1]

(a) N¹-(1-(cyclooctylmethyl)piperidin-4-yl)-4-(methylsulfonyl)benzene-1,2-diamine

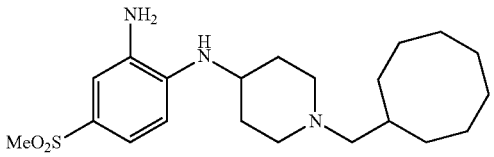 [SMILES: CS(=O)(=O)c1ccc(NC2CCN(CC3CCCCCCC3)CC2)c(N)c1]

The title compound was prepared using the product from Example 2a and 1-fluoro-4-(methylsulfonyl)-2-nitrobenzene according to the procedure described in Example 1d (0.28 g, 63%): $^1$H NMR (CDCl$_3$, 400 MHz) δ 7.40 (dd, J=8.4, 2.0 Hz, 1H), 7.23 (d, J=2.4 Hz, 1H), 6.66 (d, J=8.8 Hz, 1H), 3.95 (d, J=6.8 Hz, 1H), 3.36 (m, 1H), 3.31 (br s, 2H), 2.99 (s, 3H), 2.82 (m, 2H), 2.08 (m, 5H), 1.69 (m, 4H), 1.59-1.41 (m, 12H), 1.21 (m, 2H). LRMS (ES+) m/z for C$_{21}$H$_{35}$N$_3$O$_2$S [M+H]$^+$ calc'd 393. found 393.

(b) 2-(azetidin-3-yl)-1-(1-(cyclooctylmethyl)piperidin-4-yl)-5-(methylsulfonyl)-1H-benzo[d]imidazole The title compound was prepared using N-Boc-azetidine-3-carboxylic acid and the product from Example 41a according to the procedure described in Example 1d (26 mg, 55% over three steps). LRMS (ES+) m/z for C$_{25}$H$_{39}$N$_4$O$_2$S [M+H]$^+$ calc'd 459. found 459.

Example 44

(R)-1-(1-(cyclooctylmethyl)piperidin-4-yl)-5-(methylsulfonyl)-2-(pyrrolidin-3-yl)-1H-benzo[d]imidazole

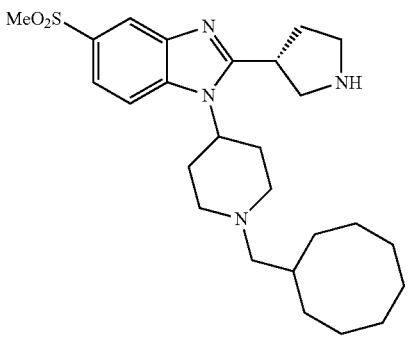 [SMILES: CS(=O)(=O)c1ccc2c(c1)nc([C@@H]1CCNC1)n2C1CCN(CC2CCCCCCC2)CC1]

The title compound was prepared using (R)—N-Boc-β-proline and the product from Example 43a and converted to HCl salt according to the procedure described in Example 1d (28 mg, 47% over three steps). LRMS (ES+) m/z for C$_{26}$H$_{41}$N$_4$O$_2$S [M+H]$^+$ calc'd 473. found 473.

Example 45

2-(azetidin-3-yl)-1-(1-(cyclooctylmethyl)piperidin-4-yl)-5-chloro-1H-benzo[d]imidazole

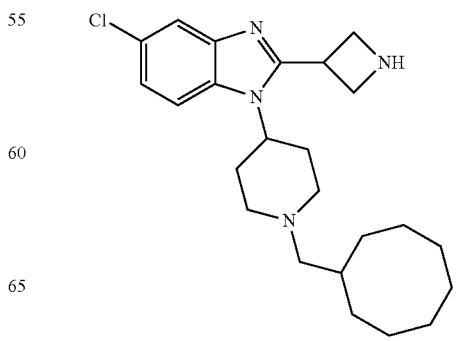

(a) N¹-(1-(cyclooctylmethyl)piperidin-4-yl)-4-chlorobenzene-1,2-diamine

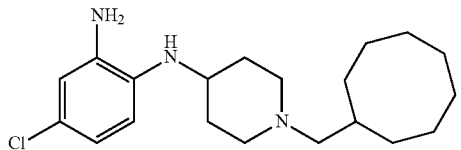 [SMILES: Nc1cc(Cl)ccc1NC1CCN(CC2CCCCCCC2)CC1]

The title compound was prepared using the product from Example 2a and 1-fluoro-4-chloro-2-nitrobenzene according to the procedure described in Example 2b (0.156 g, 28%): $^1$H NMR (CDCl$_3$, 400 MHz) δ 6.73 (dd, J=8.4, 2.4 Hz, 1H), 6.69 (d, J=2.0 Hz, 1H), 6.56 (d, J=8.4 Hz, 1H), 3.40 (br s, 2H), 3.19 (tt, J=10.0, 4.0 Hz, 1H), 2.81 (m, 2H), 2.09 (d, J=7.2 Hz, 2H), 2.04 (d, J=12.0 Hz, 2H), 2.00 (d, J=13.6 Hz, 2H), 1.71-1.41 (m, 16H), 1.21 (m, 2H). LRMS (ES+) m/z for C$_{20}$H$_{33}$ClN$_3$ [M+H]$^+$ calc'd 350. found 350.

(b) 2-(azetidin-3-yl)-1-(1-(cyclooctylmethyl)piperidin-4-yl)-5-chloro-1H-benzo[d]imidazole The title compound was prepared using N-Boc-azetidine-3-carboxylic acid and the product from Example 47a and converted to HCl salt according to the procedure described in Example 1d (38 mg, 85% over three steps). LRMS (ES+) m/z for C$_{24}$H$_{36}$ClN$_4$ [M+H]$^+$ calc'd 415. found 415.

Example 46

(R)-5-chloro-1-(1-(cyclooctylmethyl)piperidin-4-yl)-2-(pyrrolidin-3-yl)-1H-benzo[d]imidazole

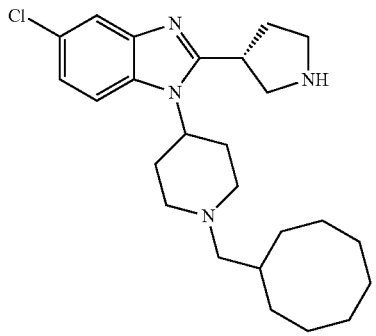 [SMILES: Clc1ccc2c(c1)nc([C@@H]1CCNC1)n2C1CCN(CC2CCCCCCC2)CC1]

The title compound was prepared using (R)—N-Boc-β-proline and the product from Example 45a and converted to HCl salt according to the procedure described in Example 1d (39 mg, 62% over three steps). LRMS (ES+) m/z for C$_{25}$H$_{38}$ClN$_4$ [M+H]$^+$ calc'd 429. found 429.

Example 47

2-(azetidin-3-yl)-1-(1-(((1R,4R)-bicyclo[2.2.1]hept-5-en-2-ylmethyl)piperidin-4-yl)-1H-benzo[d]imidazole

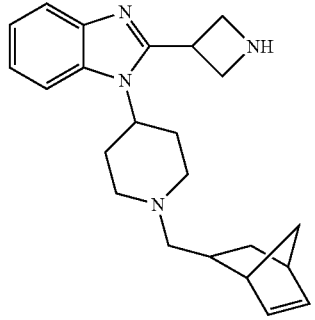 [SMILES: C1=CC2CC1CC2CN1CCC(n2c(C3CNC3)nc3ccccc32)CC1]

(a) 1-((1R,4R)-bicyclo[2.2.1]hept-5-en-2-ylmethyl)piperidin-4-amine

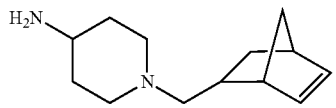 [SMILES: NC1CCN(CC2CC3C=CC2C3)CC1]

The title compound was prepared using 5-norbornene-2-carboxaldehyde according to the procedure described in Example 2a (1.58 g, quant.). LRMS (ES+) m/z for C$_{13}$H$_{23}$N$_2$ [M+H]$^+$ calc'd 207. found 207.

(b) N¹-(1-((1R,4R)-bicyclo[2.2.1]hept-5-en-2-ylmethyl)piperidin-4-yl)benzene-1,2-diamine

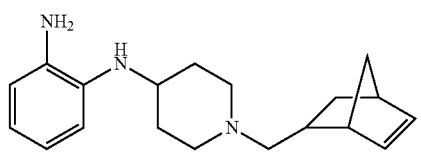 [SMILES: Nc1ccccc1NC1CCN(CC2CC3C=CC2C3)CC1]

The title compound was prepared using the product from Example 47a and 1-fluoro-2-nitrobenzene according to the procedure described in Example 2b (0.340 g, 62%). LRMS (ES+) m/z for C$_{19}$H$_{28}$N$_3$ [M+H]$^+$ calc'd 298. found 298.

(c) 2-(azetidin-3-yl)-1-(1-(((1R,4R)-bicyclo[2.2.1]hept-5-en-2-ylmethyl)piperidin-4-yl)-1H-benzo[d]imidazole The title compound was prepared using N-Boc-azetidine-3-carboxylic acid and the product from Example 47a according to the procedure described in Example 1d (34 mg, 73% over three steps). LRMS (ES+) m/z for C$_{23}$H$_{31}$N$_4$ [M+H]$^+$ calc'd 363. found 363.

Example 48

1-(1-((1R,4R)-bicyclo[2.2.1]hept-5-en-2-ylmethyl)piperidin-4-yl)-2-((R)-pyrrolidin-3-yl)-1H-benzo[d]imidazole

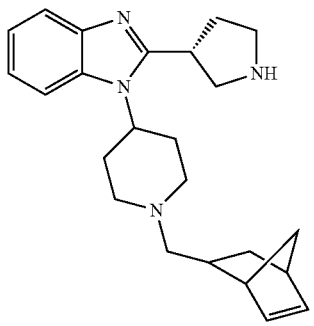 [SMILES: C1=CC2CC1CC2CN1CCC(n2c([C@@H]3CCNC3)nc3ccccc32)CC1]

The title compound was prepared using (R)—N-Boc-β-proline and the product from Example 47b according to the procedure described in Example 1d (34 mg, 59% over three steps). LRMS (ES+) m/z for $C_{24}H_{33}N_4$ [M+H]$^+$ calc'd 377. found 377.

Example 49

2-(azetidin-3-yl)-1-(1-((2,6,6-trimethylcyclohex-1-en-1-yl)methyl)piperidin-4-yl)-1H-benzo[d]imidazole

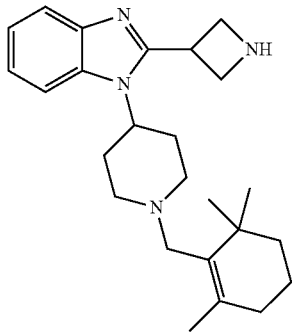 [SMILES: CC1=C(CN2CCC(n3c(C4CNC4)nc4ccccc43)CC2)C(C)(C)CCC1]

(a) 1-((2,6,6-trimethylcyclohex-1-en-1-yl)methyl)piperidin-4-amine

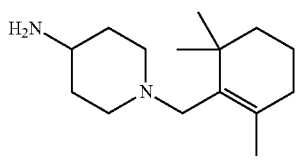 [SMILES: CC1=C(CN2CCC(N)CC2)C(C)(C)CCC1]

The title compound was prepared using β-cyclocitral according to the procedure described in Example 2a (0.93 g, 36%). LRMS (ES+) m/z for $C_{15}H_{29}N_2$ [M+H]$^+$ calc'd 237. found 237.

(b) N$^1$-(1-((2,6,6-trimethylcyclohex-1-en-1-yl)methyl)piperidin-4-yl)benzene-1,2-diamine

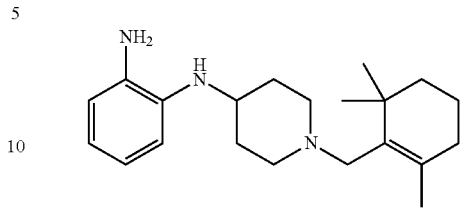

The title compound was prepared using the product from Example 49a according to the procedure described in Example 2b (0.33 g, 68%): $^1$H NMR (CDCl$_3$, 400 MHz) δ 6.80 (ddd, J=8.0, 7.2, 1.6 Hz, 1H), 6.72 (dd, J=7.6, 1.6 Hz, 1H), 6.66 (m, 2H), 3.30 (br s, 2H), 3.24 (m, 2H), 2.97 (s, 2H), 2.81 (m, 2H), 2.01 (m, 6H), 1.67 (s, 3H), 1.63 (m, 2H), 1.45 (m, 1H), 1.40 (m, 3H), 1.08 (s, 6H). LRMS (ES+) m/z for $C_{21}H_{34}N_3$ [M+H]$^+$ calc'd 328. found 328.

(c) 2-(azetidin-3-yl)-1-(1-((2,6,6-trimethylcyclohex-1-en-1-yl)methyl)piperidin-4-yl)-1H-benzo[d]imidazole The title compound was prepared using N-Boc-azetidine-3-carboxylic acid and the product from Example 49b according to the procedure described in Example 1d (27 mg, 56% over three steps): $^1$H NMR (DMSO-d$_6$, 400 MHz) δ 7.61 (d, J=7.2 Hz, 1H), 7.48 (d, J=7.2 Hz, 1H), 7.18 (qd, J=7.2, 1.2 Hz, 1H), 7.16 (qd, J=7.2, 1.2 Hz, 1H), 4.30 (quint, J=8.0 Hz, 1H), 4.05 (m, 1H), 4.00 (t, J=8.0 Hz, 2H), 3.81 (t, J=8.0 Hz, 2H), 3.03 (s, 2H), 2.98 (d, J=11.2 Hz, 2H), 2.28 (m, 2H), 2.06 (t, J=11.2 Hz, 2H), 1.97 (t, J=6.0 Hz, 2H), 1.75 (d, J=9.2 Hz, 2H), 1.69 (s, 3H), 1.61 (m, 2H), 1.41 (m, 2H), 1.14 (s, 6H). LRMS (ES+) m/z for $C_{25}H_{37}N_4$ [M+H]$^+$ calc'd 393. found 393.

Example 50

(R)-2-(pyrrolidin-3-yl)-1-(1-((2,6,6-trimethylcyclohex-1-en-1-yl)methyl)piperidin-4-yl)-1H-benzo[d]imidazole

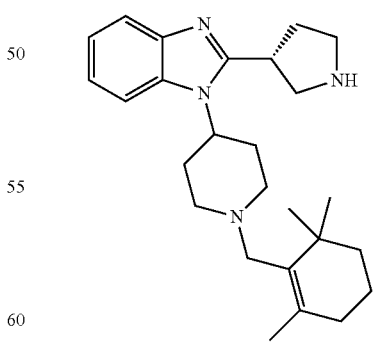

The title compound was prepared using (R)—N-Boc-β-proline and the product from Example 49b according to the procedure described in Example 1d (37 mg, 66% over three steps). LRMS (ES+) m/z for $C_{26}H_{39}N_4$ [M+H]$^+$ calc'd 407. found 407.

Example 51

(3R,5S)-5-(1-(1-((2,6,6-trimethylcyclohex-1-en-1-yl)methyl)piperidin-4-yl)-1H-benzo[d]imidazol-2-yl)pyrrolidin-3-ol

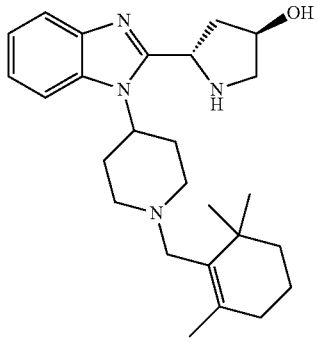 [SMILES: CC1=C(CN2CCC(n3c([C@@H]4C[C@@H](O)CN4)nc4ccccc43)CC2)C(C)(C)CCC1]

The title compound was prepared using N-Boc-(2S,4R)-4-hydroxypyrrolidine-2-carboxylic acid and the product from Example 49b according to the procedure described in Example 1d (9 mg, 17% over three steps). LRMS (ES+) m/z for $C_{26}H_{39}N_4O$ [M+H]$^+$ calc'd 423. found 423.

Example 52

(S)-2-(pyrrolidin-3-yl)-1-(1-((2,6,6-trimethylcyclohex-1-en-1-yl)methyl)piperidin-4-yl)-1H-benzo[d]imidazole

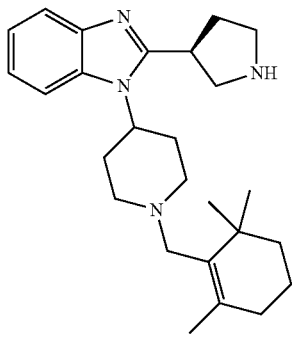 [SMILES: CC1=C(CN2CCC(n3c([C@H]4CCNC4)nc4ccccc43)CC2)C(C)(C)CCC1]

The title compound was prepared using (S)—N-Boc-β-proline and the product from Example 49b according to the procedure described in Example 1d (30 mg, 60% over three steps). LRMS (ES+) m/z for $C_{26}H_{39}N_4$ [M+H]$^+$ calc'd 407. found 407.

Example 53

2-(azetidin-3-yl)-5-fluoro-1-(1-((2,6,6-trimethylcyclohex-1-en-1-yl)methyl)piperidin-4-yl)-1H-benzo[d]imidazole

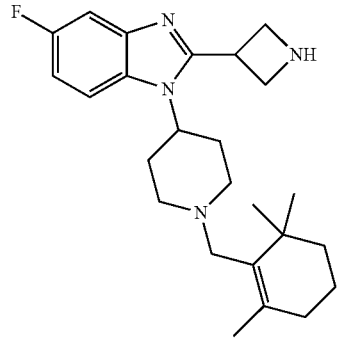 [SMILES: CC1=C(CN2CCC(n3c(C4CNC4)nc4cc(F)ccc43)CC2)C(C)(C)CCC1]

(a) 4-fluoro-N$^1$-(1-((2,6,6-trimethylcyclohex-1-en-1-yl)methyl)piperidin-4-yl)benzene-1,2-diamine

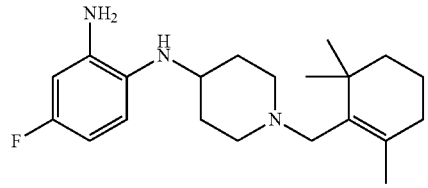 [SMILES: CC1=C(CN2CCC(Nc3ccc(F)cc3N)CC2)C(C)(C)CCC1]

The title compound was prepared using the product from Example 49a and 2,5-difluoro-nitrobenzene according to the procedure described in Example 2b (0.43 g, 86%). LRMS (ES+) m/z for $C_{20}H_{33}FN_3$ [M+H]$^+$ calc'd 346. found 346.

(b) 2-(azetidin-3-yl)-5-fluoro-1-(1-((2,6,6-trimethyl-cyclohex-1-en-1-yl)methyl)piperidin-4-yl)-1H-benzo[d]imidazole The title compound was prepared using N-Boc-azetidine-3-carboxylic acid and the product from Example 49a according to the procedure described in Example 1d (33 mg, 70% over three steps): $^1$H NMR (CDCl$_3$, 400 MHz) δ 7.41 (m, 2H), 6.97 (td, J=9.2, 2.4 Hz, 1H), 4.24 (m, 3H), 3.95 (m, 3H), 3.07 (m, 4H), 2.40 (qd, J=12.0, 4.0 Hz, 2H), 2.01 (m, 4H), 1.74 (dd, J=12.0, 2.4 Hz, 2H), 1.71 (s, 3H), 1.67-1.62 (m, 3H), 1.45 (m, 2H), 1.15 (s, 6H). LRMS (ES+) m/z for $C_{25}H_{36}FN_4$ [M+H]$^+$ calc'd 411. found 411.

Example 54

(R)-5-fluoro-2-(pyrrolidin-3-yl)-1-(1-((2,6,6-trimethylcyclohex-1-en-1-yl)methyl)piperidin-4-yl)-1H-benzo[d]imidazole

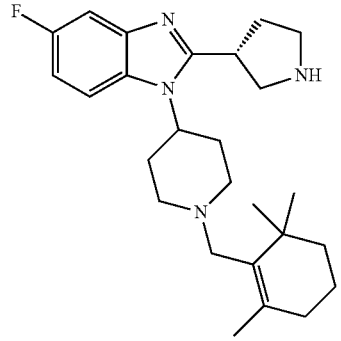 [SMILES: CC1=C(CN2CCC(n3c([C@@H]4CCNC4)nc4cc(F)ccc43)CC2)C(C)(C)CCC1]

The title compound was prepared using (R)—N-Boc-β-proline and the product from Example 49a according to the procedure described in Example 1d (20 mg, 42% over three steps): $^1$H NMR (CDCl$_3$, 400 MHz) δ 7.42 (dd, J 9.2 Hz, 4.8 Hz, 1H), 7.37 (dd, J=9.2, 2.8 Hz, 1H), 6.95 (td, J=9.2, 2.8 Hz, 1H), 4.24 (tt, J=12.4, 4.4 Hz, 1H), 3.50 (m, 1H), 3.37 (dd, J=11.2, 5.6 Hz, 1H), 3.28 (m, 2H), 3.06 (m, 5H), 2.48 (m, 2H), 2.25 (m, 2H), 2.03 (m, 4H), 1.80 (m, 2H), 1.71 (s, 3H), 1.67-1.63 (m, 3H), 1.45 (m, 2H), 1.15 (s, 6H). LRMS (ES+) m/z for C$_{25}$H$_{38}$FN$_4$ [M+H]$^+$ calc'd 425. found 425.

Example 55

2-(azetidin-3-yl)-1-(1-(cyclohexylmethyl)piperidin-4-yl)-1H-benzo[d]imidazole

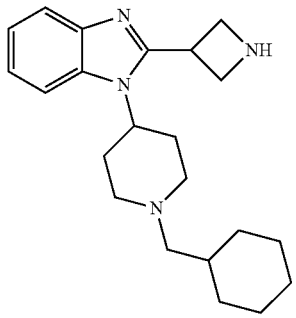 [SMILES: c1ccc2c(c1)nc(C1CNC1)n2C1CCN(CC2CCCCC2)CC1]

(a) 1-(cyclohexylmethyl)piperidin-4-amine

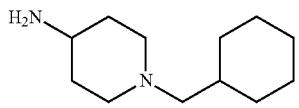 [SMILES: NC1CCN(CC2CCCCC2)CC1]

The title compound was prepared using cyclohexanecarboxaldehyde according to the procedure described in Example 2a (1.24 g, 54%). LRMS (ES+) m/z for C$_{12}$H$_{25}$N$_2$ [M+H]$^+$ calc'd 197. found 197.

(b) N$^1$-(1-(cyclohexylmethyl)piperidin-4-yl)benzene-1,2-diamine

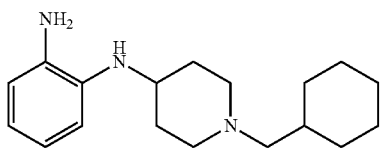 [SMILES: Nc1ccccc1NC1CCN(CC2CCCCC2)CC1]

The title compound was prepared using the product from Example 55a according to the procedure described in Example 49b (0.45 g, 94%): $^1$H NMR (CDCl$_3$, 400 MHz) δ 6.79 (ddd, J=8.0, 7.2, 1.6 Hz, 1H), 6.72 (dd, J=8.0, 1.6 Hz, 1H), 6.66 (m, 2H), 3.32 (br s, 2H), 3.25 (tt, J=10.0, 4.0 Hz, 1H), 2.81 (m, 2H), 2.14 (d, J=6.8 Hz, 2H), 2.05 (t, J=12.4 Hz, 4H), 1.77 (d, J=13.6 Hz, 2H), 1.69 (m, 4H), 1.51 (m, 3H), 1.21 (m, 3H), 0.87 (m, 2H). LRMS (ES+) m/z for C$_{18}$H$_{30}$N$_3$ [M+H]$^+$ calc'd 288. found 288.

(c) 2-(azetidin-3-yl)-1-(1-(cyclohexylmethyl)piperidin-4-yl)-1H-benzo[d]imidazole The title compound was prepared using N-Boc-azetidine-3-carboxylic acid and the product from Example 55b according to the procedure described in Example 1d (40 mg, 65% over three steps). LRMS (ES+) m/z for C$_{22}$H$_{33}$N$_4$ [M+H]$^+$ calc'd 353. found 353.

Example 56

(R)-1-(1-(cyclohexylmethyl)piperidin-4-yl)-2-(pyrrolidin-3-yl)-1H-benzo[d]imidazole

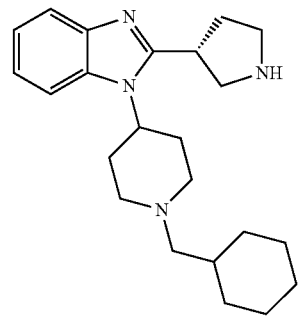 [SMILES: c1ccc2c(c1)nc([C@@H]1CCNC1)n2C1CCN(CC2CCCCC2)CC1]

The title compound was prepared using (R)—N-Boc-β-proline and the product from Example 55b according to the procedure described in Example 1d (27 mg, 72% over three steps). LRMS (ES+) m/z for C$_{23}$H$_{35}$N$_4$ [M+H]$^+$ calc'd 367. found 367.

Example 57

1-(1-(((1R,5S)-6,6-dimethylbicyclo[3.1.1]hept-2-en-2-yl)methyl)piperidin-4-yl)-2-((R)-pyrrolidin-3-yl)-1H-benzo[d]imidazole

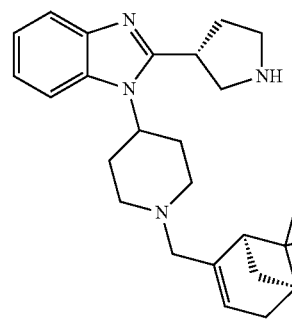

(a) 1-(((1R,5S)-6,6-dimethylbicyclo[3.1.1]hept-2-en-2-yl)methyl)piperidin-4-amine

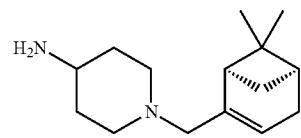 [SMILES: CC1(C)[C@H]2CC=C(CN3CCC(N)CC3)[C@@H]1C2]

The title compound was prepared using cyclohexanecarboxaldehyde according to the procedure described in Example 2a (1.21 g, 54%). LRMS (ES+) m/z for $C_{15}H_{27}N_2$ [M+H]$^+$ calc'd 235. found 235.

(b) $N^1$-(1-(((1R,5S)-6,6-dimethylbicyclo[3.1.1]hept-2-en-3-yl)methyl)piperidin-4-yl)benzene-1,2-diamine

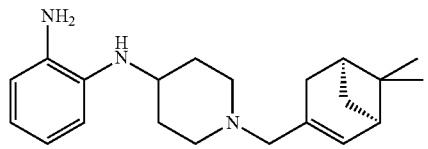 [SMILES: CC1(C)[C@@H]2CC(CN3CCC(Nc4ccccc4N)CC3)=C[C@H]1C2]

The title compound was prepared using the product from Example 57a according to the procedure described in Example 49b (0.08 g, 22%). LRMS (ES+) m/z for $C_{21}H_{31}N_3$ [M+H]$^+$ calc'd 326. found 326.

(c) 1-(1-(((1R,5S)-6,6-dimethylbicyclo[3.1.1]hept-2-en-2-yl)methyl)piperidin-4-yl)-2-((R)-pyrrolidin-3-yl)-1H-benzo[d]imidazole The title compound was prepared using (R)—N-Boc-β-proline and the product from Example 57b according to the procedure described in Example 1d (40 mg, 65% over three steps). LRMS (ES+) m/z for $C_{26}H_{37}N_4$ [M+H]$^+$ calc'd 405. found 405.

Example 58

1-(1-((1R,5S)-6,6-dimethylbicyclo[3.1.1]hept-2-en-2-yl)methyl)piperidin-4-yl)-2-((R)-piperidin-3-yl)-1H-benzo[d]imidazole

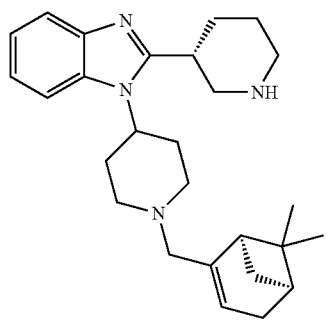 [SMILES: CC1(C)[C@H]2CC=C(CN3CCC(n4c([C@@H]5CCCNC5)nc5ccccc54)CC3)[C@@H]1C2]

The title compound was prepared using (R)—N-Boc-nipecotic acid and the product from Example 57b according to the procedure described in Example 1d (32 mg, 62% over three steps). LRMS (ES+) m/z for $C_{27}H_{39}N_4$ [M+H]$^+$ calc'd 419. found 419.

Example 59

(R)-1-(1-benzylpiperidin-4-yl)-2-(pyrrolidin-3-yl)-1H-benzo[d]imidazole

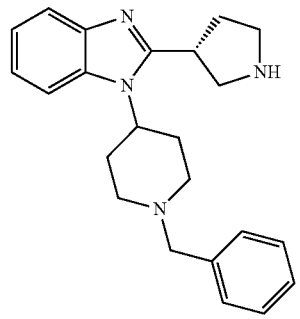 [SMILES: c1ccc(CN2CCC(n3c([C@@H]4CCNC4)nc4ccccc43)CC2)cc1]

(a) $N^1$-(1-benzylpiperidin-4-yl)benzene-1,2-diamine

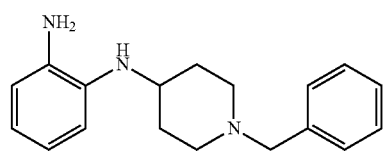 [SMILES: Nc1ccccc1NC1CCN(Cc2ccccc2)CC1]

The title compound was prepared using 1-benzyl 4-amino piperidine according to the procedure described in Example 49b (1.01 g, 72%): LRMS (ES+) m/z for $C_{18}H_{24}N_3$ [M+H]$^+$ calc'd 282. found 282.

(b) 1-(1-benzylpiperidin-4-yl)-2-(pyrrolidin-3-yl)-1H-benzo[d]imidazole

The title compound was prepared using N-Boc-β-proline and the product from Example 59a according to the procedure described in Example 1d (43 mg, 28% over three steps). LRMS (ES+) m/z for $C_{23}H_{29}N_4$ [M+H]$^+$ calc'd 361. found 361.

Example 60

(R)-1-(1-benzylpiperidin-4-yl)-2-(piperidin-3-yl)-1H-benzo[d]imidazole

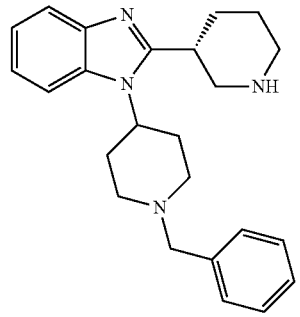 [SMILES: c1ccc(CN2CCC(n3c([C@@H]4CCCNC4)nc4ccccc43)CC2)cc1]

The title compound was prepared using (R)—N-Boc-nipecotic acid and the product from Example 59a according to the procedure described in Example 1d (37 mg, 28% over three steps). LRMS (ES+) m/z for $C_{24}H_{31}N_4$ [M+H]$^+$ calc'd 375. found 375.

Example 61

(R)-1-(3-(1-(1-(cyclooctylmethyl)piperidin-4-yl)-1H-benzo[d]imidazol-2-yl)pyrrolidin-1-yl)ethanone

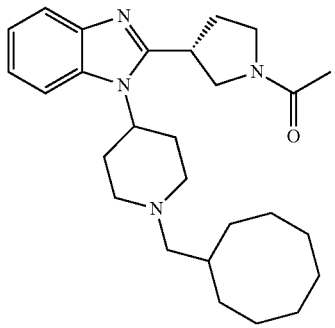 [SMILES: CC(=O)N1CC[C@@H](c2nc3ccccc3n2C2CCN(CC3CCCCCCC3)CC2)C1]

To a solution of the product from Example 11 (38 mg, 0.096 mmol) in methylene chloride (5 mL) at 0° C. was added triethylamine (12 mg, 0.12 mmol), acetyl chloride (12 mg, 0.15 mmol), and DMAP (5 mg). The reaction mixture was stirred overnight, quenched by addition of methanol (3 mL) and the solvent was removed. The residue was partitioned between methylene chloride (10 mL) and an aqueous solution of sodium bicarbonate, and the aqueous layer was washed with two additional portions of methylene chloride (5 mL). The organic layers were combined, dried, filtered, and concentrated to dryness. The residue was purified by flash column chromatography (1-9% methanol in methylene chloride) to afford the title compound as a colorless solid (33 mg, 79%): LRMS (ES+) m/z for $C_{27}H_{41}N_4O$ [M+H]$^+$ calc'd 437. found 437.

Example 62

(R)-1-(1-(cyclooctylmethyl)piperidin-4-yl)-2-(1-methylpyrrolidin-3-yl)-1H-benzo[d]imidazole

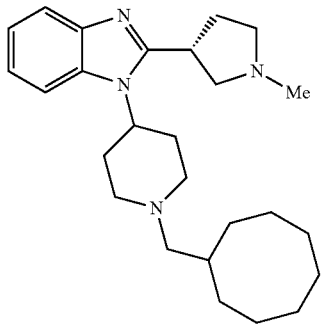 [SMILES: CN1CC[C@@H](c2nc3ccccc3n2C2CCN(CC3CCCCCCC3)CC2)C1]

To a solution of (R)-tert-butyl 3-(1-(1-(cyclooctylmethyl)piperidin-4-yl)-1H-benzo[d]imidazol-2-yl)pyrrolidine-1-carboxylate (43 mg, 0.087 mmol) in THF (5 mL) was carefully added lithium aluminum hydride (38 mg, 1.0 mmol) at 0° C. The reaction mixture was heated to 60° C. and stirred overnight. After the reaction was determined to be complete by LC/MS, the mixture was cooled, treated with water (5 mL), and the organic solvent was removed in vacuo. The aqueous layer was extracted three times with methylene chloride (5 mL) and the combined organic layers were washed with brine, dried over sodium sulfate, filtered, and concentrated to dryness. The residue was purified by flash column chromatography (5-18% methanol in methylene chloride with 0.1% NH$_4$OH) to afford the title compound as a colorless solid (6 mg, 18%): LRMS (ES+) m/z for $C_{27}H_{41}N_4$ [M+H]$^+$ calc'd 409. found 409.

Example 63

(R)-1-(1-benzylpiperidin-4-yl)-2-(1-methylpyrrolidin-3-yl)-1H-benzo[d]imidazole

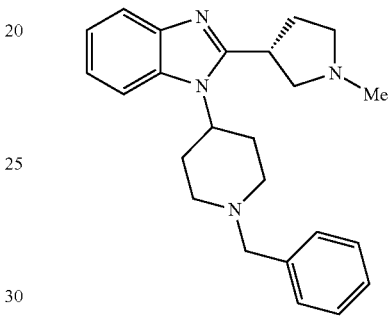

The title compound was prepared according to the procedure described in Example 62 (15 mg, 26%). LRMS (ES+) m/z for $C_{24}H_{31}N_4$ [M+H]$^+$ calc'd 375. found 375.

Example 64

(R)-2-(azetidin-3-yl)-1-(1-(1-cyclohexylethyl)piperidin-4-yl)-1H-benzo[d]imidazole

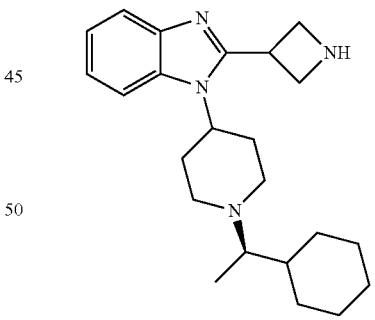

(a) (R)-1-(1-cyclohexylethyl)piperidin-4-one

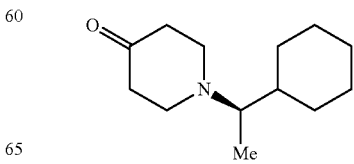

The title compound was prepared according to the procedure described in Example 1b (0.78 g, 37%). LRMS (ES+) m/z for $C_{13}H_{25}NO$ [M+H]$^+$ calc'd 210. found 210.

(b) (R)—N1-(1-(1-cyclohexylethyl)piperidin-4-yl)benzene-1,2-diamine

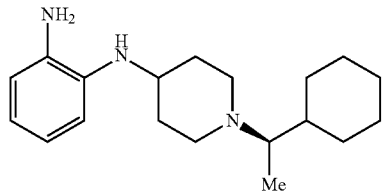 [SMILES: C[C@H](C1CCCCC1)N1CCC(Nc2ccccc2N)CC1]

The title compound was prepared using the product from Example 64a according to the procedure described in Example 1c (0.58 g, 94%). LRMS (ES+) m/z for $C_{19}H_{32}N_3$ [M+H]$^+$ calc'd 302. found 302.

(c) (R)-2-(azetidin-3-yl)-1-(1-(1-cyclohexylethyl)piperidin-4-yl)-1H-benzo[d]imidazole The title compound was prepared using N-Boc-azetidine-3-carboxylic acid and the product from Example 64b according to the procedure described in Example 1d (28 mg, 56% over three steps). LRMS (ES+) m/z for $C_{23}H_{35}N_4$ [M+H]$^+$ calc'd 367. found 367.

Example 65

1-(1-((R)-1-cyclohexylethyl)piperidin-4-yl)-2-((S)-pyrrolidin-3-yl)-1H-benzo[d]imidazole

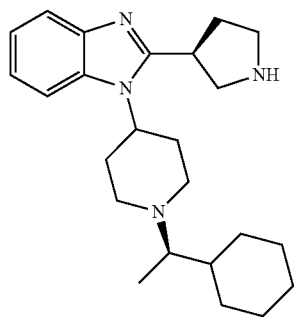 [SMILES: C[C@H](C1CCCCC1)N1CCC(n2c([C@H]3CCNC3)nc3ccccc32)CC1]

The title compound was prepared using (S)—N-Boc-β-proline and the product from Example 64b according to procedure described in Example 1d (31 mg, 61% over three steps). LRMS (ES+) m/z for $C_{24}H_{37}N_4$ [M+H]$^+$ calc'd 381. found 381.

Example 66

(S)-2-(azetidin-3-yl)-1-(1-(1-cyclohexylethyl)piperidin-4-yl)-1H-benzo[d]imidazole

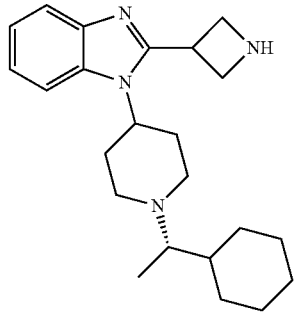 [SMILES: C[C@@H](C1CCCCC1)N1CCC(n2c(C3CNC3)nc3ccccc32)CC1]

(a) (S)-1-(1-cyclohexylethyl)piperidin-4-one

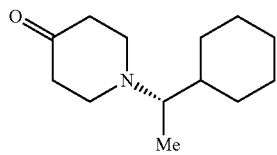 [SMILES: C[C@@H](C1CCCCC1)N1CCC(=O)CC1]

The title compound was prepared according to the procedure described in Example 1b (0.30 g, 19%). LRMS (ES+) m/z for $C_{13}H_{25}NO$ [M+H]$^+$ calc'd 210. found 210.

(b) (S)—N$^1$-(1-(1-cyclohexylethyl)piperidin-4-yl)benzene-1,2-diamine

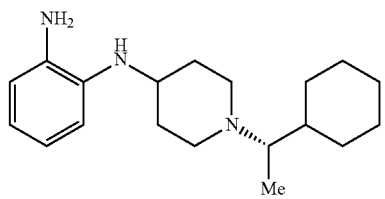 [SMILES: C[C@@H](C1CCCCC1)N1CCC(Nc2ccccc2N)CC1]

The title compound was prepared using the product from Example 64a according to the procedure described in Example 1c (0.35 g, 66%). LRMS (ES+) m/z for $C_{19}H_{32}N_3$ [M+H]$^+$ calc'd 302. found 302.

(c) (S)-2-(azetidin-3-yl)-1-(1-(1-cyclohexylethyl)piperidin-4-yl)-1H-benzo[d]imidazole The title compound was prepared using N-Boc-azetidine-3-carboxylic acid and the product from Example 64b according to the procedure described in Example 1d (32 mg, 69% over three steps). LRMS (ES+) m/z for $C_{23}H_{35}N_4$ [M+H]$^+$ calc'd 367. found 367.

Example 67

1-(1-((S)-1-cyclohexylethyl)piperidin-4-yl)-2-((S)-pyrrolidin-3-yl)-1H-benzo[d]imidazole

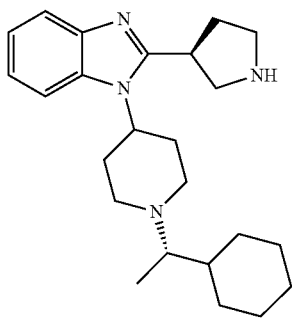 [SMILES: C[C@@H](C1CCCCC1)N1CCC(n2c([C@H]3CCNC3)nc3ccccc32)CC1]

The title compound was prepared using (S)—N-Boc-β-proline and the product from Example 64b according to the procedure described in Example 1d (33 mg, 70% over three steps). LRMS (ES+) m/z for $C_{24}H_{37}N_4$ [M+H]$^+$ calc'd 381. found 381.

Example 68

2-(azetidin-3-yl)-1-(1-(1-cyclohexylethyl)piperidin-4-yl)-1H-benzo[d]imidazole

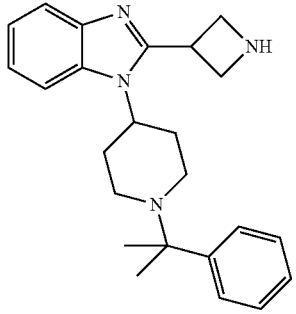 [SMILES: CC(C)(c1ccccc1)N1CCC(n2c(C3CNC3)nc3ccccc32)CC1]

(a) 1-(2-phenylpropan-2-yl)piperidin-4-one

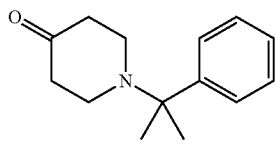 [SMILES: CC(C)(c1ccccc1)N1CCC(=O)CC1]

The title compound was prepared according to the procedure described in Example 1b (0.64 g, 53%). LRMS (ES+) m/z for $C_{14}H_{20}NO$ [M+H]$^+$ calc'd 218. found 218.

(b) N$^1$-(1-(2-phenylpropan-2-yl)piperidin-4-yl)benzene-1,2-diamine

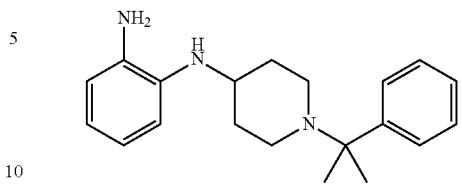

The title compound was prepared using the product from Example 68a according to the procedure described in Example 1c (0.25 g, 81%). LRMS (ES+) m/z for $C_{20}H_{28}N_3$ [M+H]$^+$ calc'd 302. found 302.

(c) 2-(azetidin-3-yl)-1-(1-(1-cyclohexylethyl)piperidin-4-yl)-1H-benzo[d]imidazole The title compound was prepared using N-Boc-azetidine-3-carboxylic acid and the product from Example 68b according to the procedure described in Example 1d (28 mg, 44% over three steps). LRMS (ES+) m/z for $C_{24}H_{31}N_4$ [M+H]$^+$ calc'd 375. found 375.

Example 69

(R)-1-(1-(2-phenylpropan-2-yl)piperidin-4-yl)-2-(pyrrolidin-3-yl)-1H-benzo[d]imidazole

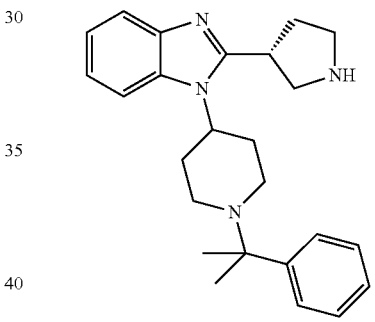

The title compound was prepared using (S)—N-Boc-β-proline and the product from Example 68b according to the procedure described in Example 1d (10 mg, 21% over three steps). LRMS (ES+) m/z for $C_{25}H_{33}N_4$ [M+H]$^+$ calc'd 389. found 389.

Example 70

2-(azetidin-3-yl)-1-(8-cyclooctyl-8-azabicyclo[3.2.1]octan-3-yl)-1H-benzo[d]imidazole

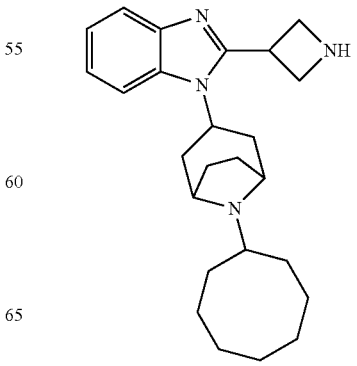

(a) 8,8-dimethyl-3-oxo-8-azabicyclo[3.2.1]octan-8-ium

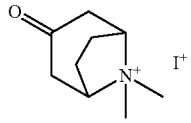

The title compound was prepared according to the procedure described in Example 1a or in Willand, et al. *Tetrahedron Lett.* 2007, 48, 5007. (20 g, 94%).

(b) 8-cyclooctyl-8-azabicyclo[3.2.1]octan-3-one

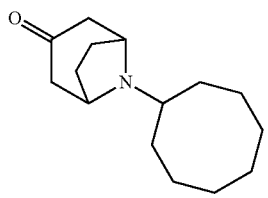 [SMILES: O=C1CC2CCC(C1)N2C1CCCCCCC1]

The title compound was prepared using cyclooctylamine and the product from Example 70a according to the procedure described in Example 1b (0.93 g, 37%). LRMS (ES+) m/z for $C_{15}H_{26}NO$ [M+H]$^+$ calc'd 236. found 236.

(c) $N^1$-(8-cyclooctyl-8-azabicyclo[3.2.1]octan-3-yl)benzene-1,2-diamine

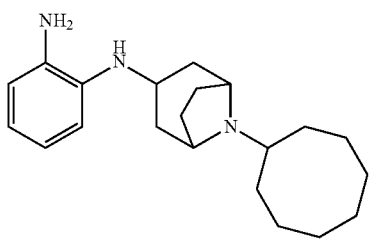 [SMILES: Nc1ccccc1NC1CC2CCC(C1)N2C1CCCCCCC1]

The title compound was prepared using the product from Example 70b according to the procedure described in Example 1c (0.89 g, 68%). LRMS (ES+) m/z for $C_{21}H_{34}N_3$ [M+H]$^+$ calc'd 328. found 328.

(d) 2-(azetidin-3-yl)-1-(8-cyclooctyl-8-azabicyclo[3.2.1]octan-3-yl)-1H-benzo[d]imidazole The title compound was prepared using N-Boc-azetidine-3-carboxylic acid and the product from Example 70c and converted to HCl salt according to the procedure described in Example 1d (17 mg, 22% over three steps). LRMS (ES+) m/z for $C_{25}H_{33}N_4$ [M+H]$^+$ calc'd 393. found 393.

Example 71

1-(8-cyclooctyl-8-azabicyclo[3.2.1]octan-3-yl)-2-((R)-pyrrolidin-3-yl)-1H-benzo[d]imidazole

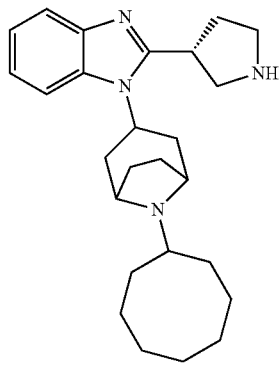 [SMILES: c1ccc2c(c1)nc([C@@H]1CCNC1)n2C1CC2CCC(C1)N2C1CCCCCCC1]

The title compound was prepared using (R)—N-Boc-β-proline and the product from Example 70c and converted to HCl salt according to the procedure described in Example 1d (5 mg, 6% over three steps). LRMS (ES+) m/z for $C_{26}H_{39}N_4$ [M+H]$^+$ calc'd 407. found 407.

Example 72

1-(8-cyclooctyl-8-azabicyclo[3.2.1]octan-3-yl)-2-((R)-piperidin-3-yl)-1H-benzo[d]imidazole

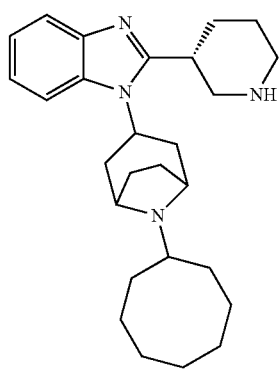 [SMILES: c1ccc2c(c1)nc([C@@H]1CCCNC1)n2C1CC2CCC(C1)N2C1CCCCCCC1]

The title compound was prepared using N-Boc-nipecotic acid and the product from Example 70c and converted to HCl salt according to the procedure described in Example 1d (13 mg, 16% over three steps). LRMS (ES+) m/z for $C_{27}H_{41}N_4$ [M+H]$^+$ calc'd 421. found 421.

Example 73

2-(azetidin-3-yl)-1-(8-((R)-1-cyclohexylethyl)-8-azabicyclo[3.2.1]octan-3-yl)-1H-benzo[d]imidazole

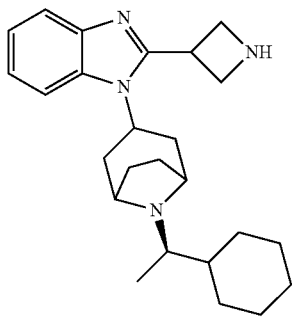 [SMILES: C[C@H](C1CCCCC1)N1C2CCC1CC(n1c(C3CNC3)nc3ccccc31)C2]

8-((R)-1-cyclohexylethyl)-8-azabicyclo[3.2.1]octan-3-one

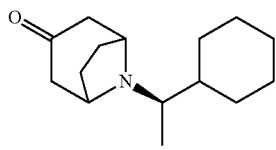 [SMILES: C[C@H](C1CCCCC1)N1C2CCC1CC(=O)C2]

The title compound was prepared using 1-cyclohexylethanamine and the product from Example 70a according to the procedure described in Example 1b (0.37 g, 52%). LRMS (ES+) m/z for $C_{15}H_{26}NO$ [M+H]$^+$ calc'd 236. found 236.

(b) N1-(8-((R)-1-cyclohexylethyl)-8-azabicyclo[3.2.1]octan-3-yl)benzene-1,2-diamine

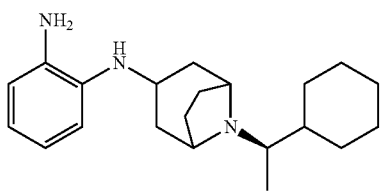 [SMILES: C[C@H](C1CCCCC1)N1C2CCC1CC(Nc1ccccc1N)C2]

The title compound was prepared using the product from Example 73a according to the procedure described in Example 1c (0.17 g, 60%). LRMS (ES+) m/z for $C_{21}H_{34}N_3$ [M+H]$^+$ calc'd 328. found 328.

(c) 2-(azetidin-3-yl)-1-(8-((R)-1-cyclohexylethyl)-8-azabicyclo[3.2.1]octan-3-yl)-1H-benzo[d]imidazole The title compound was prepared using N-Boc-azetidine-3-carboxylic acid and the product from Example 73b according to the procedure described in Example 1d (10 mg, 21% over two steps). LRMS (ES+) m/z for $C_{25}H_{37}N_4$ [M+H]$^+$ calc'd 393. found 393.

Example 74

1-(8-((R)-1-cyclohexylethyl)-8-azabicyclo[3.2.1]octan-3-yl)-2-((S)-pyrrolidin-3-yl)-1H-benzo[d]imidazole

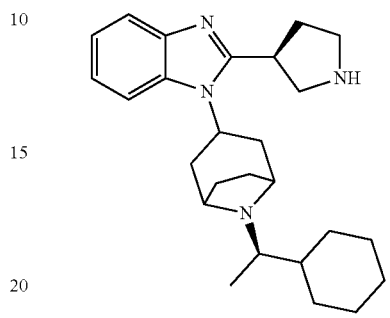

The title compound was prepared using (S)—N-Boc-β-proline and the product from Example 73b and converted to HCl salt according to the procedure described in Example 1d (34 mg, 54% over three steps). LRMS (ES+) m/z for $C_{26}H_{39}N_4$ [M+H]$^+$ calc'd 407. found 407.

Example 75

2-(azetidin-3-yl)-1-(8-(cycloheptylmethyl)-8-azabicyclo[3.2.1]octan-3-yl)-1H-benzo[d]imidazole

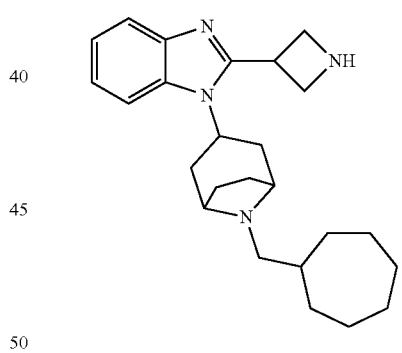

(a) 8-(cycloheptylmethyl)-8-azabicyclo[3.2.1]octan-3-one

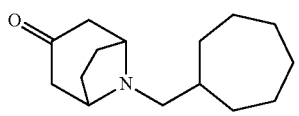 [SMILES: O=C1CC2CCC(C1)N2CC1CCCCCC1]

The title compound was prepared using cycloheptylmethanamine and the product from Example 70a according to the procedure described in Example 1b (1.41 g, 60%). LRMS (ES+) m/z for $C_{15}H_{26}NO$ [M+H]$^+$ calc'd 236. found 236.

(b) N¹-(8-(cycloheptylmethyl)-8-azabicyclo[3.2.1]octan-3-yl)benzene-1,2-diamine

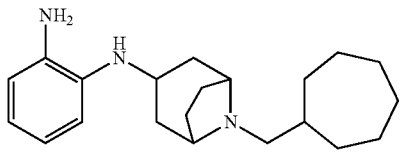 [SMILES: Nc1ccccc1NC1CC2CCC(C1)N2CC1CCCCCC1]

The title compound was prepared using the product from Example 75a according to the procedure described in Example 1c (0.44 g, 57%). LRMS (ES+) m/z for $C_{21}H_{34}N_3$ [M+H]⁺ calc'd 328. found 328.

(c) 2-(azetidin-3-yl)-1-(8-(cycloheptylmethyl)-8-azabicyclo[3.2.1]octan-3-yl)-1H-benzo[d]imidazole The title compound was prepared using N-Boc-azetidine-3-carboxylic acid and the product from Example 75b and converted to HCl salt according to the procedure described in Example 1d (33 mg, 43% over two steps). LRMS (ES+) m/z for $C_{25}H_{37}N_4$ [M+H]⁺ calc'd 393. found 393.

Example 76

1-(8-(cycloheptylmethyl)-8-azabicyclo[3.2.1]octan-3-yl)-2-((R)-pyrrolidin-3-yl)-1H-benzo[d]imidazole

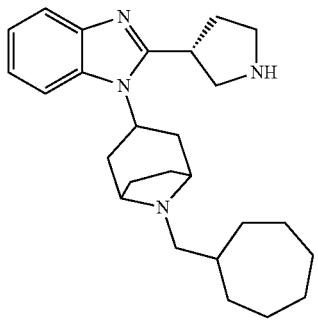 [SMILES: c1ccc2c(c1)nc([C@@H]1CCNC1)n2C1CC2CCC(C1)N2CC1CCCCCC1]

The title compound was prepared using (R)—N-Boc-β-proline and the product from Example 75b and converted to HCl salt according to the procedure described in Example 1d (33 mg, 42% over three steps). LRMS (ES+) m/z for $C_{26}H_{39}N_4$ [M+H]⁺ calc'd 407. found 407.

Example 77

1-(8-(cycloheptylmethyl)-8-azabicyclo[3.2.1]octan-3-yl)-2-((S)-pyrrolidin-3-yl)-1H-benzo[d]imidazole

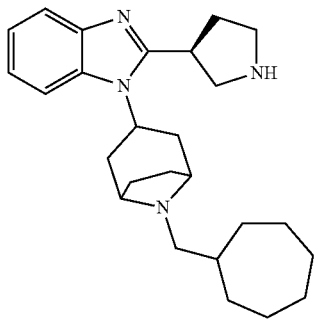 [SMILES: c1ccc2c(c1)nc([C@H]1CCNC1)n2C1CC2CCC(C1)N2CC1CCCCCC1]

The title compound was prepared using (S)—N-Boc-β-proline and the product from Example 75b and converted to HCl salt according to the procedure described in Example 1d (26 mg, 33% over three steps). LRMS (ES+) m/z for $C_{26}H_{39}N_4$ [M+H]⁺ calc'd 407. found 407.

Example 78

1-(1-(2-ethylhexyl)piperidin-4-yl)-2-((R)-pyrrolidin-3-yl)-1H-benzo[d]imidazole

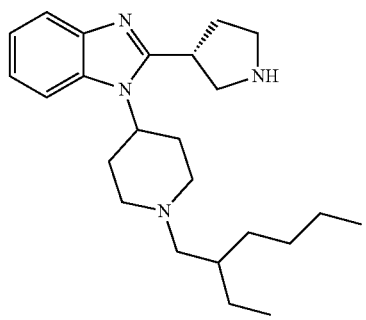 [SMILES: CCCCC(CC)CN1CCC(n2c([C@@H]3CCNC3)nc3ccccc32)CC1]

(a) 8-(cycloheptylmethyl)-8-azabicyclo[3.2.1]octan-3-one

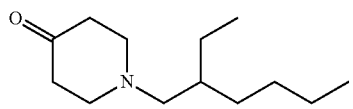

The title compound was prepared using 2-ethylhexan-1-amine and the product from Example 1a according to the procedure described in Example 1b (0.72 g, 48%). LRMS (ES+) m/z for $C_{13}H_{26}NO$ [M+H]⁺ calc'd 212. found 212.

(b) N¹-(8-(cycloheptylmethyl)-8-azabicyclo[3.2.1]octan-3-yl)benzene-1,2-diamine

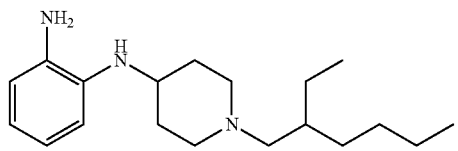 [SMILES: CCCCC(CC)CN1CCC(Nc2ccccc2N)CC1]

The title compound was prepared using the product from Example 78a according to the procedure described in Example 1c (0.11 g, 36%). LRMS (ES+) m/z for $C_{19}H_{34}N_3$ [M+H]⁺ calc'd 304. found 304.

(c) 2-(azetidin-3-yl)-1-(8-(cycloheptylmethyl)-8-azabicyclo[3.2.1]octan-3-yl)-1H-benzo[d]imidazole The title compound was prepared using (R)—N-Boc-β-proline and the product from Example 78b and converted to HCl salt according to the procedure described in Example 1d (33 mg, 43% over two steps). LRMS (ES+) m/z for $C_{24}H_{39}N_4$ [M+H]⁺ calc'd 383. found 383.

Example 79

(S)-1-(1-(cyclooctylmethyl)piperidin-4-yl)-2-(pyrrolidin-2-yl)-1H-benzo[d]imidazole

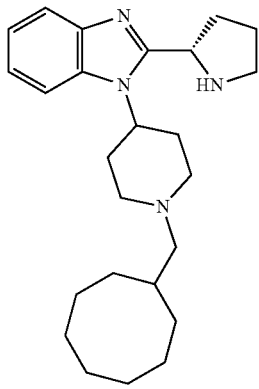 [SMILES: c1ccc2c(c1)nc([C@@H]1CCCN1)n2C1CCN(CC2CCCCCCC2)CC1]

The title compound was prepared following the procedure of Example 11 using (R)—N-Boc-proline instead of the β-proline isomer (67% over three steps). LRMS (ES+) m/z for $C_{26}H_{39}N_4$ [M+H]$^+$ calc'd 395. found 395.

Example 80

(R)-6-bromo-1-(1-(cyclooctylmethyl)piperidin-4-yl)-2-(piperidin-3-yl)-1H-benzo[d]imidazole

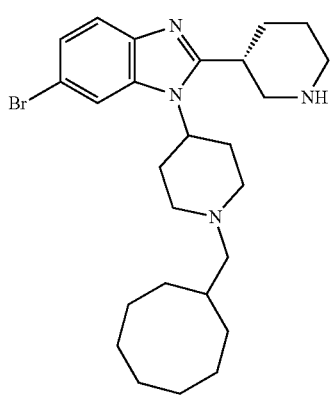 [SMILES: Brc1ccc2nc([C@@H]3CCCNC3)n(C3CCN(CC4CCCCCCC4)CC3)c2c1]

The title compound was prepared following the procedure of Example 14 using 4-bromobenzene-1,2-diamine in place of 1,2-diaminobenzene (11 mg, 48% over three steps). LRMS (ES+) m/z for $C_{26}H_{40}BrN_4$ [M+H]$^+$ calc'd 487 and 489 (Br isotopes). found 487 and 489.

Example 81

1-(1-(1-phenylethyl)piperidin-4-yl)-2-((S)-pyrrolidin-2-yl)-1H-benzo[d]imidazole

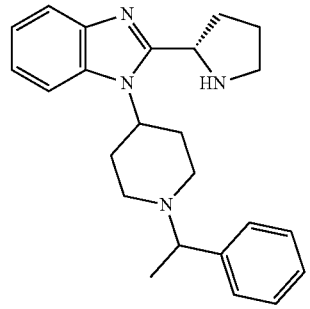 [SMILES: CC(c1ccccc1)N1CCC(n2c([C@@H]3CCCN3)nc3ccccc32)CC1]

The title compound was prepared according to the procedure described in Example 69 using (S)—N-Boc-proline in place of the β-proline isomer (7 mg, 28% over three steps), with the necessary intermediate 1-(1-phenylethyl)piperidin-4-one prepared according to the procedures described in Example 1b using phenethylamine as starting material. LRMS (ES+) m/z for $C_{24}H_{31}N_4$ [M+H]$^+$ calc'd 375. found 375.

Example 82

1-(1-(1-cyclooctylethyl)piperidin-4-yl)-2-((S)-pyrrolidin-2-yl)-1H-benzo[d]imidazole

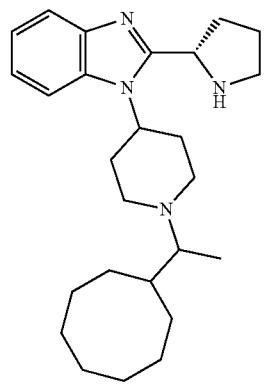 [SMILES: CC(C1CCCCCCC1)N1CCC(n2c([C@@H]3CCCN3)nc3ccccc32)CC1]

1-(1-(1-cyclooctylethyl)piperidin-4-yl)-2-((S)-pyrrolidin-2-yl)-1H-benzo[d]imidazole The title compound was prepared according to the general methods of Hayashi et. al. (J. Med. Chem. 2009, 52, 610-62), by Strecker reaction of a substituted piperidine with cyclooctane carboxaldehyde and KCN, followed by displacement of the nitrile group using MeMgBr (27% overall yield). LRMS (ES+) m/z for $C_{26}H_{41}N_4$ [M+H]$^+$ calc'd 409. found 409.

Example 83

1-(1-(1-cyclooctylethyl)piperidin-4-yl)-2-((R)-piperidin-3-yl)-1H-benzo[d]imidazole

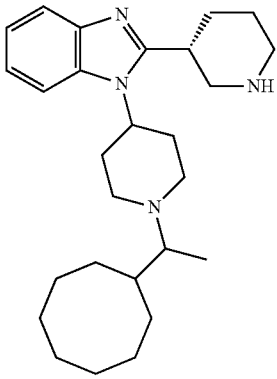 [SMILES: CC(C1CCCCCCC1)N1CCC(n2c([C@@H]3CCCNC3)nc3ccccc32)CC1]

The title compound was prepared as in Example 82. LRMS (ES+) m/z for $C_{27}H_{43}N_4$ [M+H]$^+$ calc'd 423. found 423.

Example 84

1-(1-((1R,4R)-bicyclo[2.2.1]hept-5-en-2-ylmethyl)piperidin-4-yl)-2-((S)-pyrrolidin-2-yl)-1H-benzo[d]imidazole

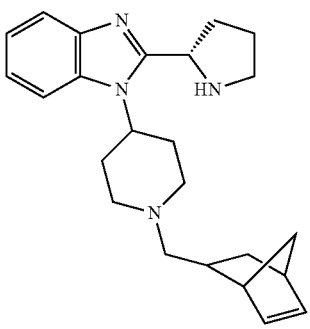 [SMILES: C1=CC2CC1CC2CN1CCC(n2c([C@@H]3CCCN3)nc3ccccc32)CC1]

The title compound was prepared as in Example 48, using (R)—N-Boc-(S)-proline in place of the β-isomer, and using the product from Example 47b according to the procedure described in Example 1d (19 mg, 67% over three steps). LRMS (ES+) m/z for $C_{24}H_{33}N_4$ [M+H]$^+$ calc'd 377. found 377.

Example 85

1-(1-(1-phenylethyl)piperidin-4-yl)-2-((R)-pyrrolidin-3-yl)-1H-benzo[d]imidazole

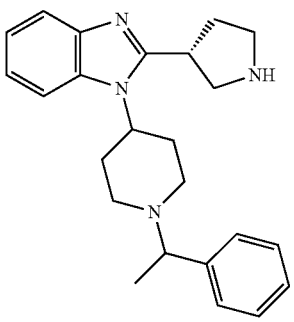 [SMILES: CC(c1ccccc1)N1CCC(n2c([C@@H]3CCNC3)nc3ccccc32)CC1]

The title compound may be prepared as in Example 81, using (S)—N-Boc-β-proline as in example 69 (13 mg, 42% over three steps), following the method of Example 1b in the preparation of the intermediate piperidinone. LRMS (ES+) m/z for $C_{24}H_{31}N_4$ [M+H]$^+$ calc'd 375. found 375.

Example 86

1-(1-(1-cyclooctylethyl)piperidin-4-yl)-2-((R)-pyrrolidin-3-yl)-1H-benzo[d]imidazole

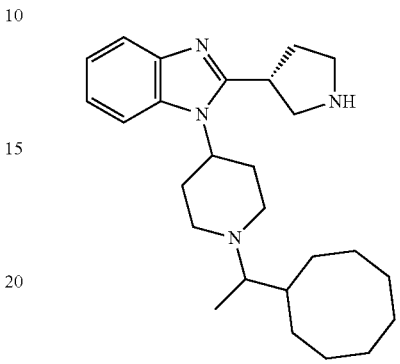

The title compound was prepared as in Example 82. LRMS (ES+) m/z for $C_{26}H_{41}N_4$ [M+H]$^+$ calc'd 409. found 409.

Example 87

1-(1-(bicyclo[2.2.1]heptan-2-ylmethyl)piperidin-4-yl)-2-((R)-pyrrolidin-3-yl)-1H-benzo[d]imidazole

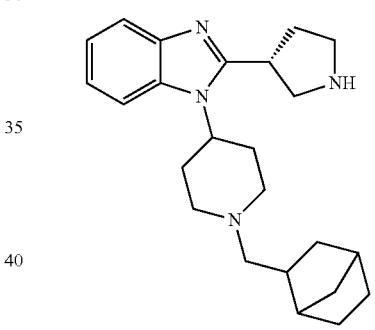

The title compound was prepared as in Example 48, except that hydrogenation of the double bond in the bicyclic ring system under standard conditions (H$_2$, 50 psi, catalytic 10% Pd/C, EtOAc) prior to Boc removal gave the desired bicyclo[2.2.1]heptane product (17 mg, 51% over four steps). LRMS (ES+) m/z for $C_{24}H_{35}N_4$ [M+H]$^+$ calc'd 379. found 379.

Example 88

1-(1-(1-((2,6,6-trimethylcyclohex-1-en-1-yl)methyl)piperidin-4-yl)-1H-benzo[d]imidazol-2-yl)cyclopentanamine

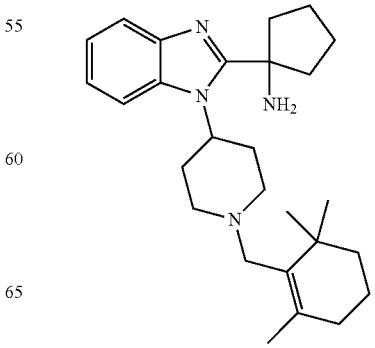

The title compound was prepared as in Example 49, using in step (c)N-Boc-1-aminocyclopentanecarboxylic acid. LRMS (ES+) m/z for $C_{27}H_{41}N_4$ [M+H]$^+$ calc'd 421. found 421.

Example 89

(R)-1-(1-(cyclooctylmethyl)piperidin-4-yl)-2-(pyrrolidin-2-yl)-1H-benzo[d]imidazole

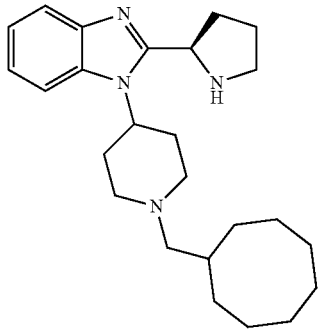

The title compound was prepared as in Example 13, using instead (R)—N-Boc-proline and the product from Example 2b according to the procedure described in Example 1d (12 mg, 29% over three steps). LRMS (ES+) m/z for $C_{26}H_{39}N_4$ [M+H]$^+$ calc'd 395. found 395.

Example 90

(R)-1-(1-(3-chlorobenzyl)piperidin-4-yl)-2-(pyrrolidin-3-yl)-1H-benzo[d]imidazole

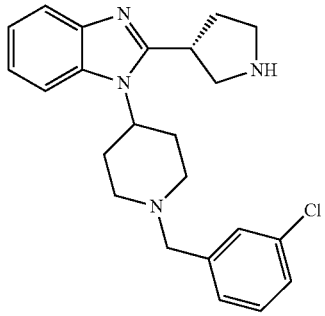

The title compound was prepared as in Example 59 but using 3-chlorobenzaldehyde and following the method of example 2a (14 mg, 56% over four steps). LRMS (ES+) m/z for $C_{23}H_{28}ClN_4$ [M+H]$^+$ calc'd 395. found 395.

Example 91

(R)-1-(1-(3-bromobenzyl)piperidin-4-yl)-2-(pyrrolidin-3-yl)-1H-benzo[d]imidazole

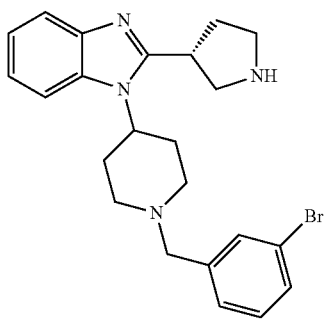 [SMILES: Brc1cccc(CN2CCC(n3c([C@@H]4CCNC4)nc4ccccc43)CC2)c1]

The title compound was prepared as in Example 59 but using 3-bromobenzaldehyde and following the method of example 2a (18 mg, 61% over four steps). LRMS (ES+) m/z for $C_{23}H_{28}BrN_4$ [M+H]$^+$ calc'd 439 and 441. found 439 and 441.

Example 92

(R)-1-(1-(benzo[d][1,3]dioxol-4-ylmethyl)piperidin-4-yl)-2-(pyrrolidin-3-yl)-1H-benzo[d]imidazole

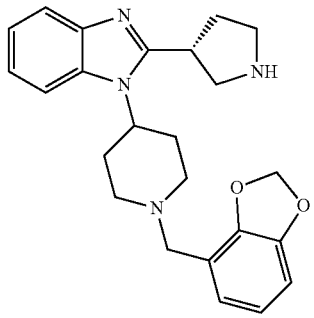 [SMILES: c1cc(CN2CCC(n3c([C@@H]4CCNC4)nc4ccccc43)CC2)c2c(c1)OCO2]

The title compound was prepared as in Example 59 but using benzo[d][1,3]dioxole-4-carbaldehyde and following the method of example 2a (22 mg, 48% over four steps). LRMS (ES+) m/z for $C_{24}H_{29}N_4O_2$ [M+H]$^+$ calc'd 405. found 405.

Example 93

(R)-4-((4-(2-(pyrrolidin-3-yl)-1H-benzo[d]imidazol-1-yl)piperidin-1-yl)methyl)phenol

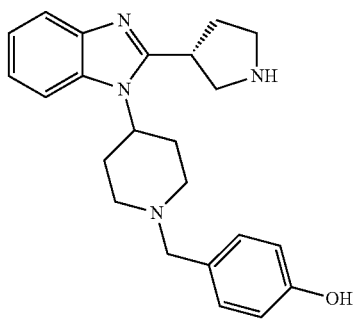 [SMILES: Oc1ccc(CN2CCC(n3c([C@@H]4CCNC4)nc4ccccc43)CC2)cc1]

The title compound was prepared as in Example 59 but using 4-(t-butyldimethylsilyoxy) benzaldehyde and following the method of example 2a (12 mg, 34% over four steps). LRMS (ES+) m/z for $C_{24}H_{29}N_4O$ [M+H]$^+$ calc'd 377. found 377.

Example 94

(R)-1-(1-([1,1'-biphenyl]-3-ylmethyl)piperidin-4-yl)-2-(pyrrolidin-3-yl)-1H-benzo[d]imidazole

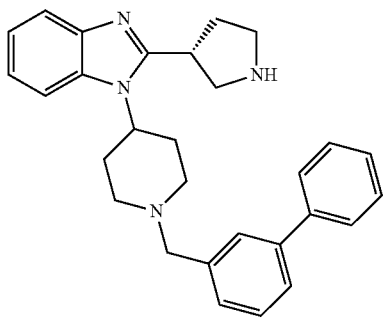 [SMILES: c1ccc(-c2cccc(CN3CCC(n4c([C@@H]5CCNC5)nc5ccccc54)CC3)c2)cc1]

The title compound was prepared as in Example 59 but using 3-phenyl benzaldehyde and following the method of example 2a (17 mg, 54% over four steps). LRMS (ES+) m/z for $C_{29}H_{33}N_4$ [M+H]$^+$ calc'd 437. found 437.

Example 95

(R)-1-(1-((2,3-dihydrobenzo[b][1,4]dioxin-6-yl)methyl)piperidin-4-yl)-2-(pyrrolidin-3-yl)-1H-benzo[d]imidazole

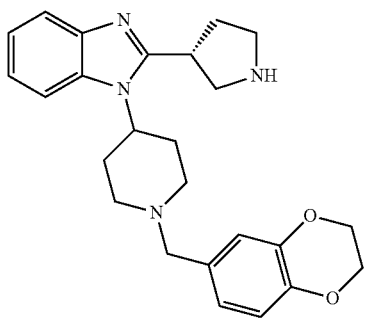 [SMILES: c1ccc2c(c1)nc([C@@H]1CCNC1)n2C1CCN(Cc2ccc3c(c2)OCCO3)CC1]

The title compound was prepared as in Example 59 but using 2,3-dihydrobenzo[b][1,4]dioxine-6-carbaldehyde and following the method of example 2a (13 mg, 57% over four steps). LRMS (ES+) m/z for $C_{25}H_{31}N_4O_2$ [M+H]$^+$ calc'd 419. found 419.

Example 96

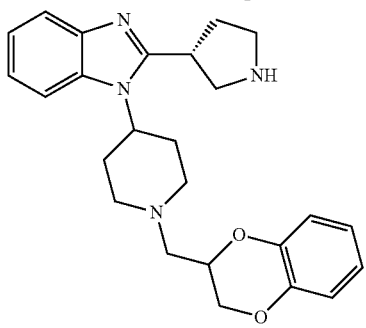 [SMILES: c1ccc2c(c1)OCC(CN1CCC(n3c([C@@H]4CCNC4)nc4ccccc43)CC1)O2]

The title compound was prepared as in Example 59 but using 2,3-dihydrobenzo[b][1,4]dioxine-2-carbaldehyde and following the method of example 2a (16 mg, 60% over four steps). LRMS (ES+) m/z for $C_{25}H_{31}N_4O_2$ [M+H]$^+$ calc'd 419. found 419.

Example 97

(R)-4-((4-(2-(pyrrolidin-3-yl)-1H-benzo[d]imidazol-1-yl)piperidin-1-yl)methyl)thiazole

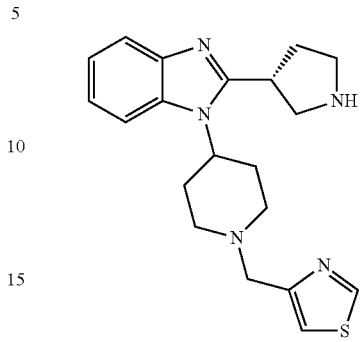

The title compound was prepared as in Example 59 but using thiazole-4-carbaldehyde and following the method of example 2a (9 mg, 35% over four steps). LRMS (ES+) m/z for $C_{20}H_{26}N_5S$ [M+H]$^+$ calc'd 368. found 368.

Example 98

(R)-6-((4-(2-(pyrrolidin-3-yl)-1H-benzo[d]imidazol-1-yl)piperidin-1-yl)methyl)-1H-indazole

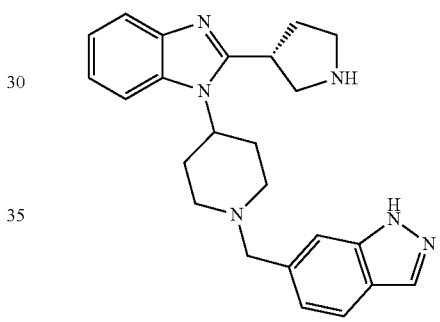

The title compound was prepared as in Example 59 but using indazole-6-carbaldehyde and following the method of example 2a (11 mg, 42% over four steps). LRMS (ES+) m/z for $C_{24}H_{29}N_6$ [M+H]$^+$ calc'd 401. found 401.

Example 99

(R)-1-(1-((5-fluoro-1H-indol-3-yl)methyl)piperidin-4-yl)-2-(pyrrolidin-3-yl)-1H-benzo[d]imidazole

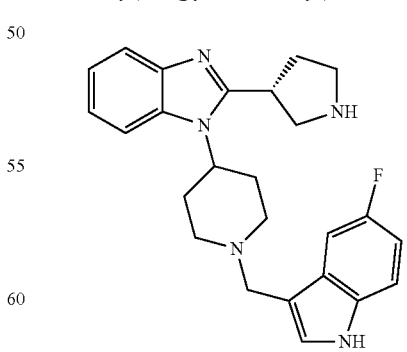

The title compound was prepared as in Example 59 but using 5-fluoroindole-3-carbaldehyde and following the method of example 2a (14 mg, 39% over four steps). LRMS (ES+) m/z for $C_{25}H_{29}FN_5$ [M+H]$^+$ calc'd 418. found 418.

Example 100

(R)-1-(1-((1H-benzo[d]imidazol-6-yl)methyl)piperidin-4-yl)-2-(pyrrolidin-3-yl)-1H-benzo[d]imidazole

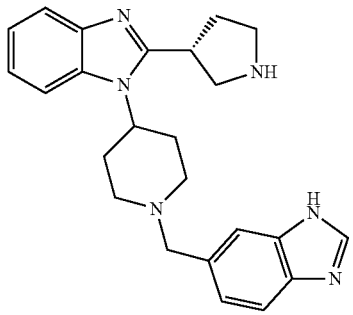 [SMILES: c1ccc2c(c1)nc([C@@H]1CCNC1)n2C1CCN(Cc2ccc3nc[nH]c3c2)CC1]

The title compound was prepared as in Example 59 but using 1H-benzo[d]imidazole-6-carbaldehyde and following the method of example 2a (11 mg, 47% over four steps). LRMS (ES+) m/z for $C_{24}H_{29}N_6$ [M+H]$^+$ calc'd 401. found 401.

Example 101

(R)-1-(1-((1-methyl-1H-indol-3-yl)methyl)piperidin-4-yl)-2-(pyrrolidin-3-yl)-1H-benzo[d]imidazole

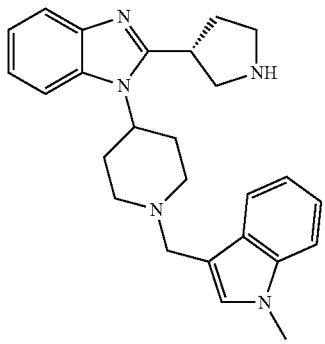 [SMILES: Cn1cc(CN2CCC(n3c([C@@H]4CCNC4)nc4ccccc43)CC2)c2ccccc21]

The title compound was prepared as in Example 59 but using N-methylindole-3-carbaldehyde and following the method of example 2a (16 mg, 43% over four steps). LRMS (ES+) m/z for $C_{26}H_{32}N_5$ [M+H]$^+$ calc'd 414. found 414.

Example 102

(R)-2-((4-(2-(pyrrolidin-3-yl)-1H-benzo[d]imidazol-1-yl)piperidin-1-yl)methyl)benzo[d]thiazole

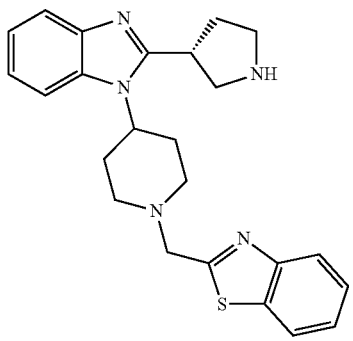 [SMILES: c1ccc2sc(CN3CCC(n4c([C@@H]5CCNC5)nc5ccccc54)CC3)nc2c1]

The title compound was prepared as in Example 59 but using benzo[d]thiazole-2-carbaldehyde and following the method of example 2a (13 mg, 49% over four steps). LRMS (ES+) m/z for $C_{24}H_{28}N_5S$ [M+H]$^+$ calc'd 418. found 418.

Example 103

(R)-1-(1-(naphthalen-2-ylmethyl)piperidin-4-yl)-2-(pyrrolidin-3-yl)-1H-benzo[d]imidazole

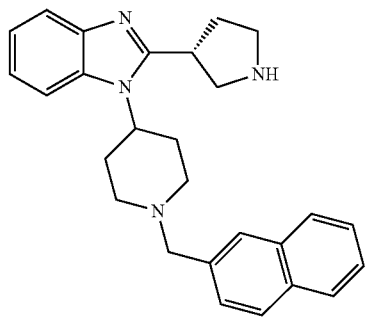 [SMILES: c1ccc2cc(CN3CCC(n4c([C@@H]5CCNC5)nc5ccccc54)CC3)ccc2c1]

The title compound was prepared as in Example 59 but using naphthalene-2-carbaldehyde and following the method of example 2a (18 mg, 47% over four steps). LRMS (ES+) m/z for $C_{27}H_{31}N_4$ [M+H]$^+$ calc'd 411. found 411.

Example 104

(R)-3-((4-(2-(pyrrolidin-3-yl)-1H-benzo[d]imidazol-1-yl)piperidin-1-yl)methyl)quinoline

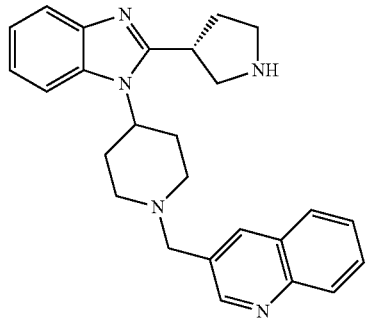 [SMILES: c1ccc2ncc(CN3CCC(n4c([C@@H]5CCNC5)nc5ccccc54)CC3)cc2c1]

The title compound was prepared as in Example 59 but using quinoline-3-carbaldehyde and following the method of example 2a (19 mg, 52% over four steps). LRMS (ES+) m/z for $C_{26}H_{30}N_5$ [M+H]$^+$ calc'd 412. found 412.

Example 105

(R)-2-chloro-6-methoxy-3-((4-(2-(pyrrolidin-3-yl)-1H-benzo[d]imidazol-1-yl)piperidin-1-yl)methyl)quinoline

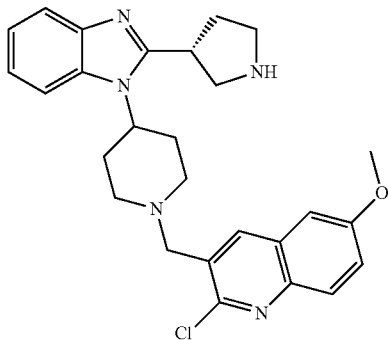 [SMILES: COc1ccc2nc(Cl)c(CN3CCC(n4c([C@@H]5CCNC5)nc5ccccc54)CC3)cc2c1]

The title compound was prepared as in Example 59 but using 2-chloro-6-methoxyquinoline-3-carbaldehyde and following the method of example 2a (20 mg, 48% over four steps). LRMS (ES+) m/z for $C_{27}H_{31}ClN_5O$ [M+H]$^+$ calc'd 476. found 476.

Example 106

(R)-1-(1-((2-chloropyridin-3-yl)methyl)piperidin-4-yl)-2-(pyrrolidin-3-yl)-1H-benzo[d]imidazole

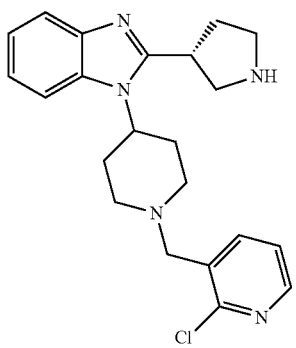 [SMILES: Clc1ncccc1CN1CCC(n2c([C@@H]3CCNC3)nc3ccccc32)CC1]

The title compound was prepared as in Example 59 but using 2-chloropyridine-3-carbaldehyde and following the method of example 2a (15 mg, 43% over four steps). LRMS (ES+) m/z for $C_{22}H_{27}ClN_5$ [M+H]$^+$ calc'd 396. found 396.

Example 107

(R)-1-(1-((6-methoxypyridin-3-yl)methyl)piperidin-4-yl)-2-(pyrrolidin-3-yl)-1H-benzo[d]imidazole

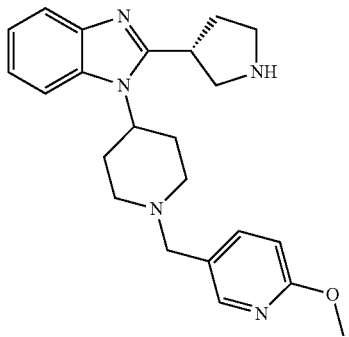 [SMILES: COc1ccc(CN2CCC(n3c([C@@H]4CCNC4)nc4ccccc43)CC2)cn1]

The title compound was prepared as in Example 59 but using 6-methoxypyridine-3-carbaldehyde and following the method of example 2a (12 mg, 38% over four steps). LRMS (ES+) m/z for $C_{23}H_{30}N_5O$ [M+H]$^+$ calc'd 392. found 392.

Example 108

(R)-1-(1-((6-methylpyridin-2-yl)methyl)piperidin-4-yl)-2-(pyrrolidin-3-yl)-1H-benzo[d]imidazole

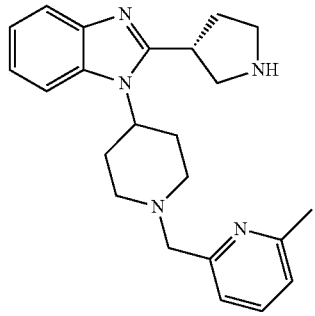 [SMILES: Cc1cccc(CN2CCC(n3c([C@@H]4CCNC4)nc4ccccc43)CC2)n1]

The title compound was prepared as in Example 59 but using 6-methylpyridine-2-carbaldehyde and following the method of example 2a (14 mg, 44% over four steps). LRMS (ES+) m/z for $C_{23}H_{30}N_5$ [M+H]$^+$ calc'd 376. found 376.

Example 109

(R)-1-(1-((2-chloropyridin-4-yl)methyl)piperidin-4-yl)-2-(pyrrolidin-3-yl)-1H-benzo[d]imidazole

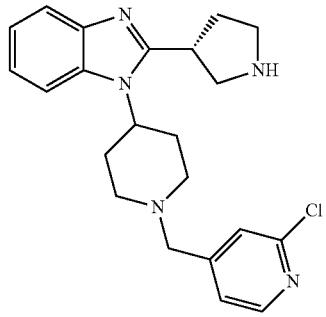 [SMILES: Clc1cc(CN2CCC(n3c([C@@H]4CCNC4)nc4ccccc43)CC2)ccn1]

The title compound was prepared as in Example 59 but using 2-chloropyridine-4-carbaldehyde and following the method of example 2a (16 mg, 46% over four steps). LRMS (ES+) m/z for $C_{22}H_{27}ClN_5$ [M+H]$^+$ calc'd 396. found 396.

Example 110

(R)-1-(1-(cyclopentylmethyl)piperidin-4-yl)-2-(pyrrolidin-3-yl)-1H-benzo[d]imidazole

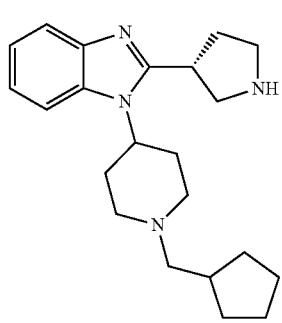 [SMILES: c1ccc2c(c1)nc([C@@H]1CCNC1)n2C1CCN(CC2CCCC2)CC1]

The title compound was prepared as in Example 59 but using cyclopentanecarbaldehyde and following the method of example 2a (14 mg, 48% over four steps). LRMS (ES+) m/z for $C_{22}H_{33}N_4$ [M+H]$^+$ calc'd 353. found 353.

Example 111

1-(1-(cyclohex-3-en-1-ylmethyl)piperidin-4-yl)-2-((R)-pyrrolidin-3-yl)-1H-benzo[d]imidazole

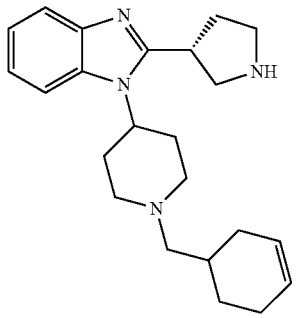 [SMILES: C1=CCC(CN2CCC(n3c([C@@H]4CCNC4)nc4ccccc43)CC2)CC1]

The title compound was prepared as in Example 59 but using cyclohex-3-enecarbaldehyde and following the method of example 2a (12 mg, 46% over four steps). LRMS (ES+) m/z for $C_{23}H_{33}N_4$ [M+H]$^+$ calc'd 365. found 365.

Example 112

(R)-1-(1-(4-fluorophenethyl)piperidin-4-yl)-2-(pyrrolidin-3-yl)-1H-benzo[d]imidazole

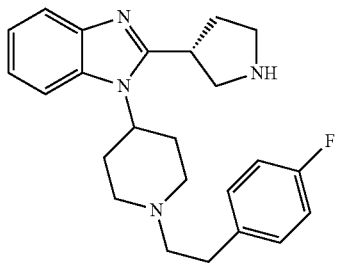 [SMILES: Fc1ccc(CCN2CCC(n3c([C@@H]4CCNC4)nc4ccccc43)CC2)cc1]

The title compound was prepared as in Example 59 but using 2-(4-fluorophenyl)acetaldehyde and following the method of example 2a (17 mg, 50% over four steps). LRMS (ES+) m/z for $C_{24}H_{30}FN_4$ [M+H]$^+$ calc'd 393. found 393.

Example 113

(R)-1-(1-(2-(benzyloxy)ethyl)piperidin-4-yl)-2-(pyrrolidin-3-yl)-1H-benzo[d]imidazole

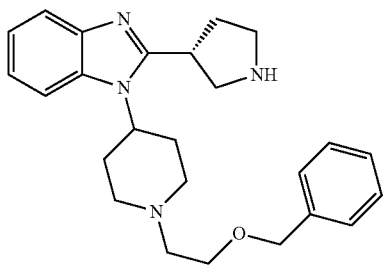 [SMILES: c1ccc(COCCN2CCC(n3c([C@@H]4CCNC4)nc4ccccc43)CC2)cc1]

The title compound was prepared as in Example 59 but using benzyloxyacetaldehyde and following the method of example 2a (14 mg, 47% over four steps). LRMS (ES+) m/z for $C_{25}H_{33}N_4O$ [M+H]$^+$ calc'd 405. found 405.

Example 114

(R,E)-1-(1-cinnamylpiperidin-4-yl)-2-(pyrrolidin-3-yl)-1H-benzo[d]imidazole

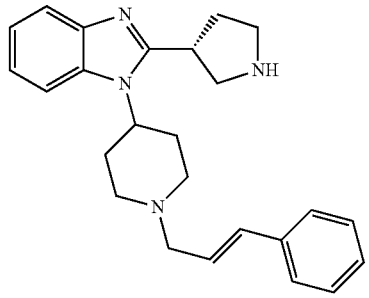 [SMILES: C(=C\c1ccccc1)/CN1CCC(n2c([C@@H]3CCNC3)nc3ccccc32)CC1]

The title compound was prepared as in Example 59 but using trans-cinnamaldehyde and following the method of example 2a (17 mg, 44% over four steps). LRMS (ES+) m/z for $C_{25}H_{31}N_4$ [M+H]$^+$ calc'd 387. found 387.

Example 115

(R)-benzyl (3-(4-(2-(pyrrolidin-3-yl)-1H-benzo[d]imidazol-1-yl)piperidin-1-yl)propyl)carbamate

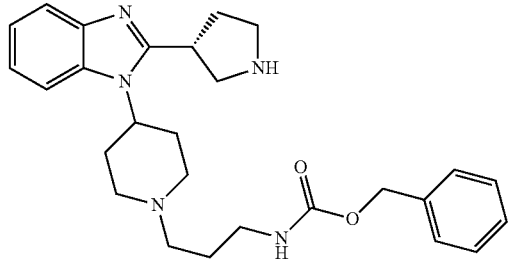 [SMILES: O=C(NCCCN1CCC(n2c([C@@H]3CCNC3)nc3ccccc32)CC1)OCc1ccccc1]

The title compound was prepared as in Example 59 but using N-Cbz-3-aminopropane-1-carbaldehyde and following the method of example 2a (18 mg, 42% over four steps). LRMS (ES+) m/z for $C_{27}H_{36}N_5O_2$ [M+H]$^+$ calc'd 462. found 462.

Example 116

(R)-1-(1-benzylpiperidin-4-yl)-4-fluoro-2-(pyrrolidin-3-yl)-1H-benzo[d]imidazole

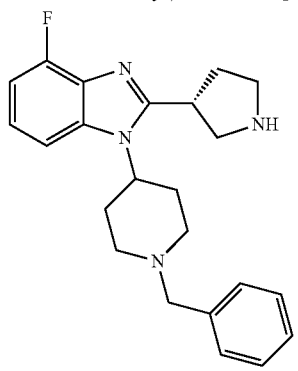

The title compound was prepared as in Example 35 but using benzaldehyde following example 2a (10 mg, 44% over four steps). LRMS (ES+) m/z for $C_{23}H_{28}FN_4$ [M+H]$^+$ calc'd 379. found 379.

Example 117

(R)-1-(1-benzylpiperidin-4-yl)-5-bromo-2-(pyrrolidin-3-yl)-1H-benzo[d]imidazole

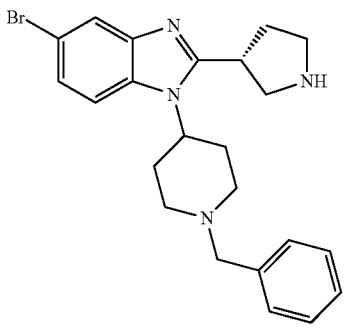

The title compound was prepared as in Example 116 but using 3-bromo-1-fluoro-2-nitrobenzene following example 2b (11 mg, 33% over five steps). LRMS (ES+) m/z for $C_{23}H_{28}BrN_4$ [M+H]$^+$ calc'd 439 & 441. found 439 and 441.

Example 118

(R)-1-(1-benzylpiperidin-4-yl)-5-fluoro-2-(pyrrolidin-3-yl)-1H-benzo[d]imidazole

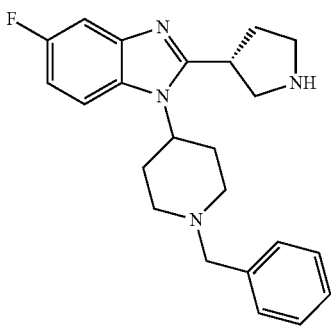 [SMILES: Fc1ccc2c(c1)nc([C@@H]1CCNC1)n2C1CCN(Cc2ccccc2)CC1]

The title compound was prepared as in Example 116 but using 1,4-difluoro-2-nitrobenzene following example 2b (13 mg, 36% over five steps). LRMS (ES+) m/z for $C_{23}H_{28}FN_4$ [M+H]$^+$ calc'd 379. found 379.

Example 119

(R)-1-(1-benzylpiperidin-4-yl)-5-methyl-2-(pyrrolidin-3-yl)-1H-benzo[d]imidazole

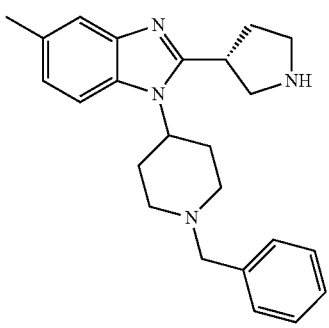 [SMILES: Cc1ccc2c(c1)nc([C@@H]1CCNC1)n2C1CCN(Cc2ccccc2)CC1]

The title compound was prepared as in Example 116 but using 1-fluoro-4-methyl-2-nitrobenzene following example 2b (14 mg, 37% over five steps). LRMS (ES+) m/z for $C_{21}H_{31}N_4$ [M+H]$^+$ calc'd 375. found 375.

Example 120

(R)-1-(1-benzylpiperidin-4-yl)-5,6-dichloro-2-(pyrrolidin-3-yl)-1H-benzo[d]imidazole

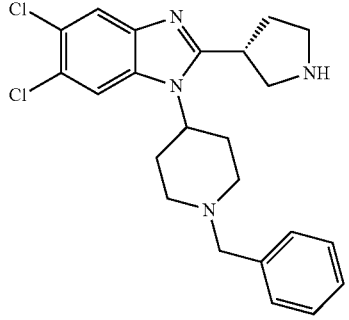 [SMILES: Clc1cc2nc([C@@H]3CCNC3)n(C3CCN(Cc4ccccc4)CC3)c2cc1Cl]

The title compound was prepared as in Example 116 but using 4,5-dichloro-1-fluoro-2-nitrobenzene following example 2b (13 mg, 40% over five steps). LRMS (ES+) m/z for $C_{23}H_{27}Cl_2N_4$ [M+H]$^+$ calc'd 429. found 429.

Example 121

(R)-1-(1-benzylpiperidin-4-yl)-6-fluoro-2-(pyrrolidin-3-yl)-1H-benzo[d]imidazole

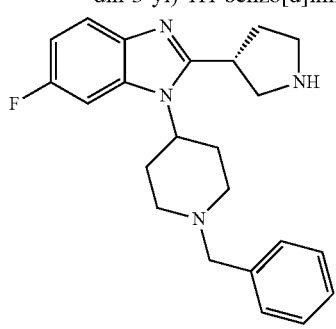

The title compound was prepared as in Example 116 but using 1,5-difluoro-2-nitrobenzene following example 2b (11 mg, 45% over five steps). LRMS (ES+) m/z for $C_{23}H_{28}FN_4$ [M+H]$^+$ calc'd 379. found 379.

Example 122

(R)-1-(1-benzylpiperidin-4-yl)-6,7-difluoro-2-(pyrrolidin-3-yl)-1H-benzo[d]imidazole

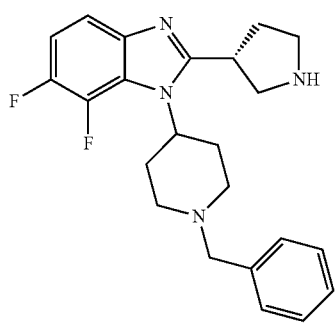

The title compound was prepared as in Example 116 but using 1,5,6-trifluoro-2-nitrobenzene following example 2b (12 mg, 48% over five steps). LRMS (ES+) m/z for $C_{23}H_{27}F_2N_4$ $[M+H]^+$ calc'd 397. found 397.

Example 123

(R)-1-(1-benzylpiperidin-4-yl)-6-chloro-5-methoxy-2-(pyrrolidin-3-yl)-1H-benzo[d]imidazole

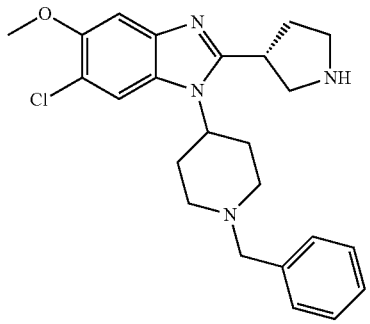 [SMILES: COc1cc2nc([C@@H]3CCNC3)n(C3CCN(Cc4ccccc4)CC3)c2cc1Cl]

The title compound was prepared as in Example 116 but using 5-chloro-1-fluoro-4-methoxy-2-nitrobenzene following example 2b (10 mg, 41% over five steps). LRMS (ES+) m/z for $C_{24}H_{30}ClN_4O$ $[M+H]^+$ calc'd 425. found 425.

Pharmaceutical Compositions and Uses

Another aspect of an embodiment of the invention provides compositions of the compounds of the invention, alone or in combination with another medicament. In various embodiments, the invention provides a pharmaceutical composition comprising a compound of the invention, e.g., of formula (I), defined further in formulas (II), (IIA), and (IIB). As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of Pharmacy*, 19th Ed., 1995, or later versions thereof, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents that do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tableting techniques may contain, but is not limited to, the following components:

Core:

| Active compound (as free compound or salt thereof) | 250 mg |
|---|---|
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate Ad. | |

Coating:

| HPMC approx. | 9 mg |
|---|---|
| *Mywacett 9-40 T approx. | 0.9 mg |

*Acylated monoglyceride used as plasticizer for film coating.

A typical capsule for oral administration may contain compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

In various embodiments, the invention provides a method of modulating a nociceptin receptor (NOP), in vivo or in vitro, comprising contacting the receptor with an effective amount or concentration of a compound of formula (I). For selective modulation of NOP, in various embodiments, the effective amount or concentration of the compound of formula (I) effective to modulate the nociceptin receptor (NOP) is less or lower than the concentration of the compound necessary to modulate the µ-opioid receptor (MOP) or the κ-opioid receptor (KOP).

Modulation of an NOP, such as selective modulation, can be medically indicated for treatment of various malconditions. Accordingly, in various embodiments, the invention provides a method of treating a malcondition in a patient, wherein modulation of an NOP receptor is medically indicated, comprising contacting a nociceptin receptor with an effective amount or concentration of a compound of formula (I) is medically indicated. The NOP modulation can be selective, such as with respect to modulation of MOP or KOP.

For instance, in various embodiments, the compound is a nociceptin receptor agonist, and the malcondition is an anxiety state, addictive disorder, cough, sleep disorders, or migraine. In other embodiments, the compound is a nociceptin receptor antagonist, and the malcondition is pain, depression, or a neurodegenerative disease such as Parkinson's disease or other neurodegenerative disorder.

Bioassay Procedures

The compounds of the invention were evaluated for activity in comparison to nociceptin. The compounds were tested at 10 µM followed on a different day by 11 point 1:3 serial dilution concentration-response curves with a starting concentration of 10 µM for those compounds that showed significant activity at 10 µM, using a cAMP biosensor approach. The cAMP biosensor assay cell lines containing either NOP, MOP or KOP were purchased from BD Biosciences (Rockville, Md.) as HEK293 cells stably expressing a cyclic nucleotide-gated (CNG) channel and the indicate receptor. Cells were cultured in T-175 $cm^2$ flasks at 37° C. and 95% relative humidity. Cells were plated and maintained in growth medium consisting of DMEM (Invitrogen catalog #11965) supplemented with 10% fetal bovine serum, 250 µg/mL geneticin and 1 µg/mL puromycin (herein referred to as "growth medium").

For NOP, MOP and KOP assays, HEK293-CNG cells were diluted in growth medium and dispensed into 384-well black-wall, clear-bottom, PDL-coated plates (final concentration: 14,000 cells/well in 20 µL) and allowed to incubate for 24 hours at 37° C. Next, 20 µL of 2.5× concentrated membrane potential dye, prepared according to manufacturer instructions, was dispensed into each well. After incubating for 3 hours at room temperature, an initial fluorescent measurement (T0) was performed (510-545 nm excitation and 565-625 nm emission) using a EnVision fluorescence plate reader (Perkin Elmer, Turku, Finland). Test compounds (10 µM final concentration), DMSO alone (2% final concentration), or the following positive control agonists nociceptin (for NOP, 1 µM final concentration), DAMGO (for MOP, 1 μM final concentration), and U50488 (for KOP, 1 μM final concentration) was added to sample or appropriate control wells for agonist mode measurements, or along with 5 nM nociceptin, 80 nM DAMGO (for MOP) or 50 nM of U50488 (for KOP) for antagonist measurements, and NECA (400 nM final concentration; an a1 adrenergic receptor agonist that is used in all experiments to initiate a cAMP response that can then be modulated by NOP, MOP or KOP activation) and the phosphodiesterase inhibitor Ro-20-1724 (25 μM final concentration). Unless otherwise noted, all reagents were purchased from commercial sources using the highest degree purity available.

The plates were incubated for 30 minutes at room temperature before the final fluorescence measurement (T30) was taken. The T30 value was divided by the background (T0). $EC_{50}$ and $IC_{50}$ values reported were obtained using GraphPad Prism 5.0 with the built in non-linear regression analysis tool. See, for example, S. P. Brothers, et al., *Mol. Pharmacol.*, 77:46-57, 2010.

Bioassay Results

Data for Selected Examples are Shown; Compounds not Shown May Also have Significant Effects x=$IC_{50}$ or $EC_{50}$ was not determined due to lack of a response at 10 μM* high=$IC_{50}$ likely greater than 100 μM

| Cpd # | Structure | NOP Agonist $EC_{50}$ (nM) | NOP Antagonist $IC_{50}$ (nM) | MOP Agonist $EC_{50}$ (nM) | MOP Antagonist $IC_{50}$ (nM) |
|---|---|---|---|---|---|
| 2 | 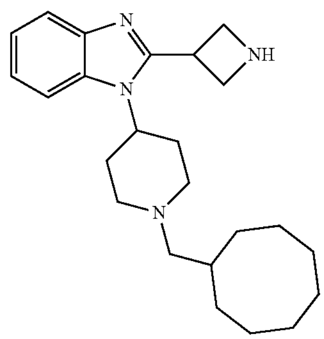 [SMILES: c1ccc2c(c1)nc(C1CNC1)n2C1CCN(CC2CCCCCCC2)CC1] | 4.6 | 11000 | 410 | high |
| 3 | 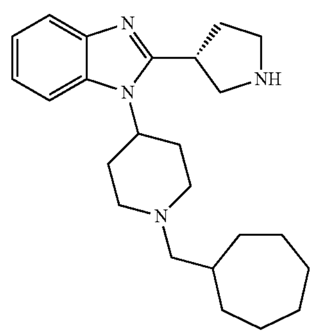 [SMILES: c1ccc2c(c1)nc([C@@H]1CCNC1)n2C1CCN(CC2CCCCCC2)CC1] | 5.1 | x | 580 | x |
| 10 | 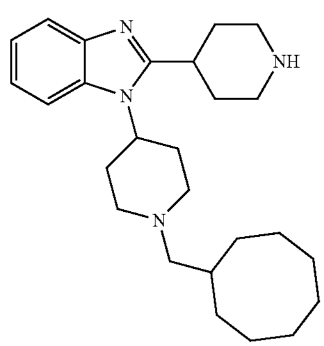 [SMILES: c1ccc2c(c1)nc(C1CCNCC1)n2C1CCN(CC2CCCCCCC2)CC1] | 3500 | x | 400 | x |

-continued
| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 11 | 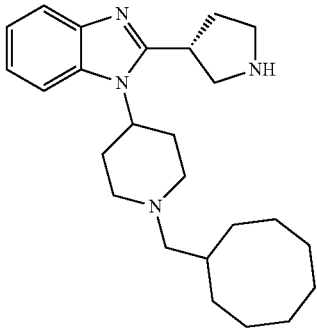 [SMILES: c1ccc2c(c1)nc([C@@H]1CCNC1)n2C1CCN(CC2CCCCCCC2)CC1] | 1.2 | high | 53 | 8800 |
| 12 | 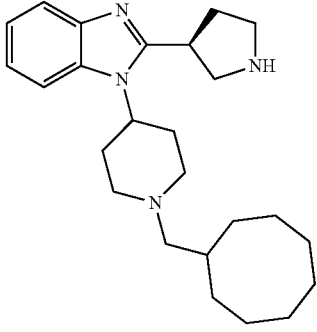 [SMILES: c1ccc2c(c1)nc([C@H]1CCNC1)n2C1CCN(CC2CCCCCCC2)CC1] | 1.0 | x | 260 | x |
| 13 | 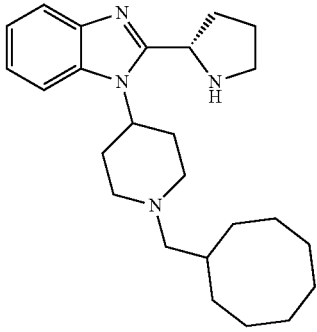 | 430 | x | 1200 | x |
| 14 | 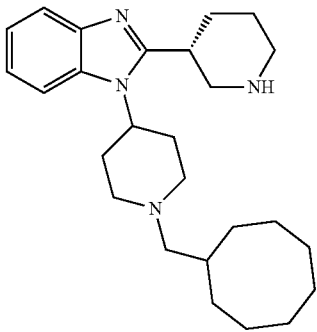 [SMILES: c1ccc2c(c1)nc([C@@H]1CCCNC1)n2C1CCN(CC2CCCCCCC2)CC1] | 5.6 | x | 15 | x |

-continued
| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 15 | 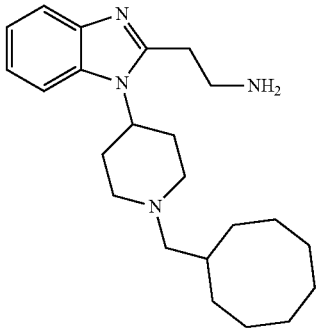 [SMILES: NCCc1nc2ccccc2n1C1CCN(CC2CCCCCCC2)CC1] | 5.2 | 13000 | 180 | 24000 |
| 18 | 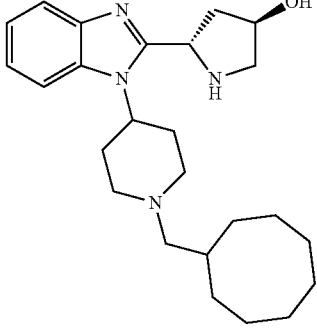 | 1400 | 7800 | 570 | 83 |
| 19 | 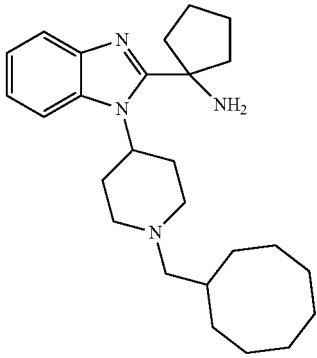 [SMILES: NC1(c2nc3ccccc3n2C2CCN(CC3CCCCCCC3)CC2)CCCC1] | 0.39 | x | high | x |
| 21 | 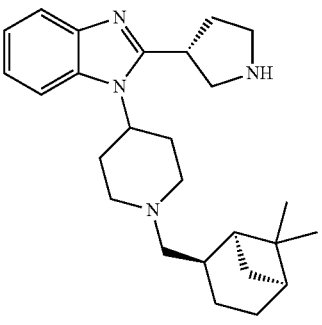 [SMILES: CC1(C)[C@H]2CC[C@@H](CN3CCC(n4c([C@@H]5CCNC5)nc5ccccc54)CC3)[C@@H]1C2] | 32 | x | high | x |

-continued
| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 29 | 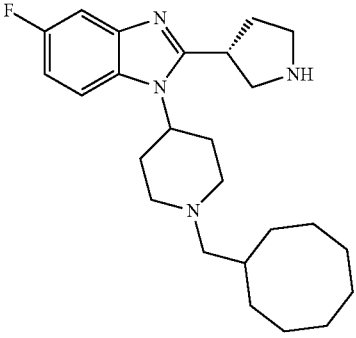 [SMILES: Fc1ccc2c(c1)nc([C@@H]1CCNC1)n2C1CCN(CC2CCCCCCC2)CC1] | 8.8 | 4700 | high | 4800 |
| 30 | 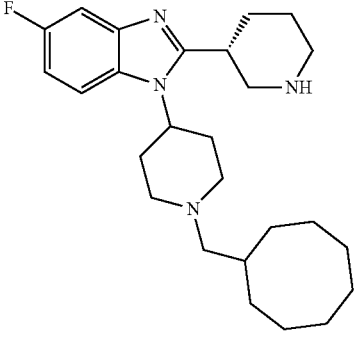 [SMILES: Fc1ccc2c(c1)nc([C@@H]1CCCNC1)n2C1CCN(CC2CCCCCCC2)CC1] | 150 | 3900 | 230 | 3000 |
| 31 | 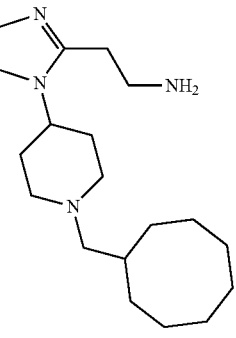 | 9.3 | x | 260 | 3400 |
| 32 | 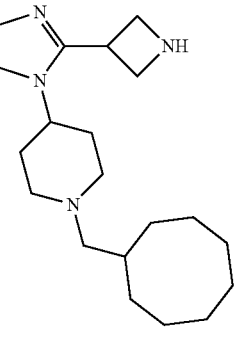 | 88 | x | 11000 | 2500 |

-continued

| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 34 | 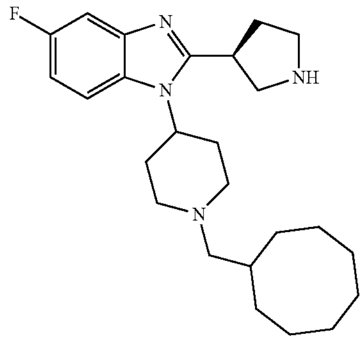 [SMILES: Fc1ccc2c(c1)nc([C@H]1CCNC1)n2C1CCN(CC2CCCCCCC2)CC1] | 29 | x | 560 | x |
| 37 | 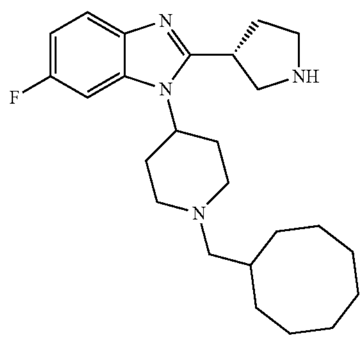 [SMILES: Fc1ccc2nc([C@@H]3CCNC3)n(C3CCN(CC4CCCCCCC4)CC3)c2c1] | 8.6 | x | high | x |
| 41 | 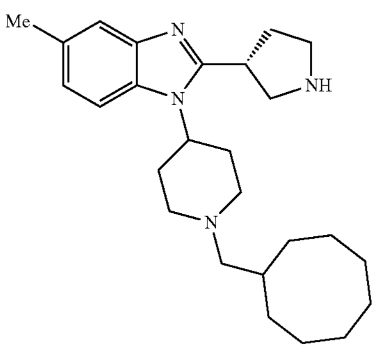 [SMILES: Cc1ccc2c(c1)nc([C@@H]1CCNC1)n2C1CCN(CC2CCCCCCC2)CC1] | 6300 | x | 5900 | high |
| 43 | 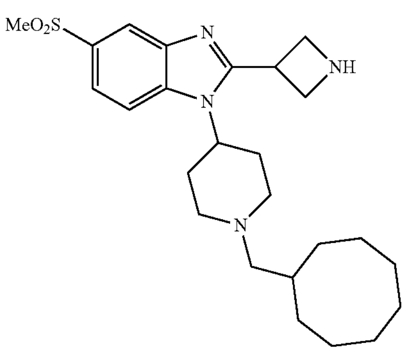 [SMILES: CS(=O)(=O)c1ccc2c(c1)nc(C1CNC1)n2C1CCN(CC2CCCCCCC2)CC1] | 0.67 | x | 1.0 | x |

-continued

| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 44 | 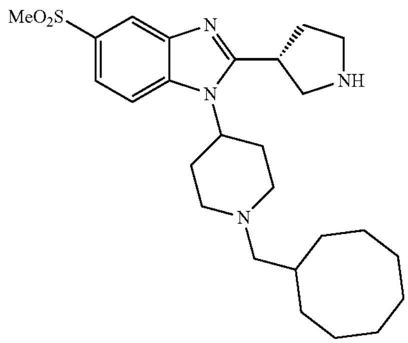 [SMILES: CS(=O)(=O)c1ccc2c(c1)nc([C@@H]1CCNC1)n2C1CCN(CC2CCCCCCC2)CC1] | 3300 | x | high | x |
| 47 | 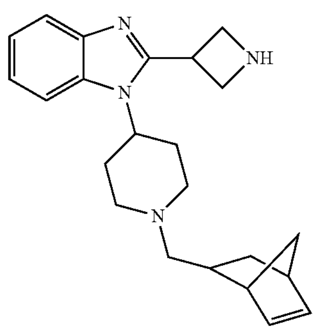 [SMILES: C1=CC2CC1CC2CN1CCC(n2c(C3CNC3)nc3ccccc32)CC1] | 310 | x | 300 | x |
| 48 | 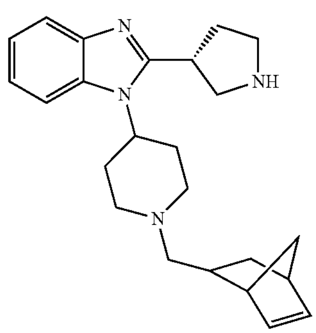 [SMILES: C1=CC2CC1CC2CN1CCC(n2c([C@@H]3CCNC3)nc3ccccc32)CC1] | 93 | x | 51 | x |
| 49 | 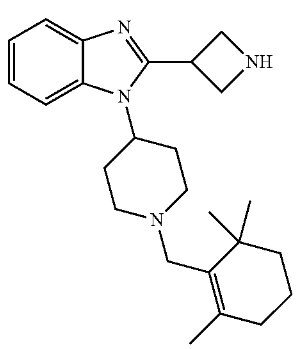 [SMILES: CC1=C(CN2CCC(n3c(C4CNC4)nc4ccccc43)CC2)C(C)(C)CCC1] | 6.2 | x | high | x |

-continued

| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 50 | 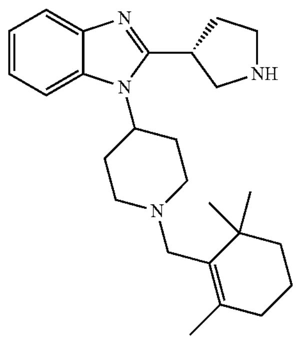 [SMILES: CC1=C(CN2CCC(n3c([C@@H]4CCNC4)nc4ccccc43)CC2)C(C)(C)CCC1] | 2.4 | x | 880 | x |
| 51 | 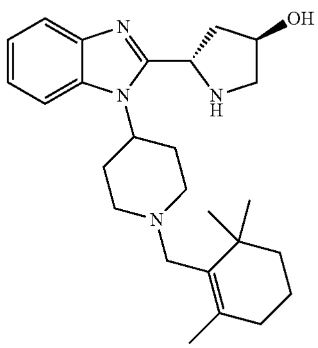 [SMILES: CC1=C(CN2CCC(n3c([C@@H]4C[C@@H](O)CN4)nc4ccccc43)CC2)C(C)(C)CCC1] | 62 | x | 150 | x |
| 52 | 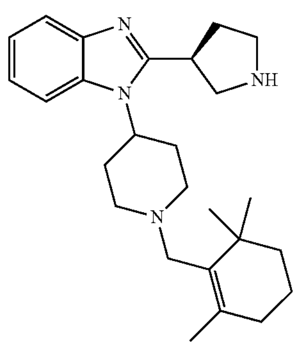 [SMILES: CC1=C(CN2CCC(n3c([C@H]4CCNC4)nc4ccccc43)CC2)C(C)(C)CCC1] | 2.0 | x | 17 | x |
| 53 | 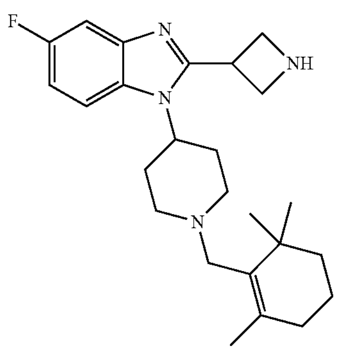 [SMILES: CC1=C(CN2CCC(n3c(C4CNC4)nc4cc(F)ccc43)CC2)C(C)(C)CCC1] | 210 | x | high | x |

-continued
| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 54 | 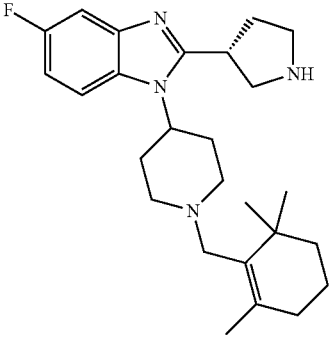 [SMILES: CC1=C(CN2CCC(n3c([C@@H]4CCNC4)nc4cc(F)ccc43)CC2)C(C)(C)CCC1] | 14 | x | 370 | x |
| 55 | 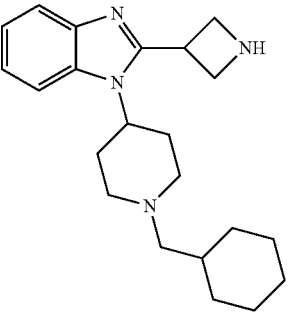 [SMILES: c1ccc2c(c1)nc(C1CNC1)n2C1CCN(CC2CCCCC2)CC1] | 140 | x | high | x |
| 56 | 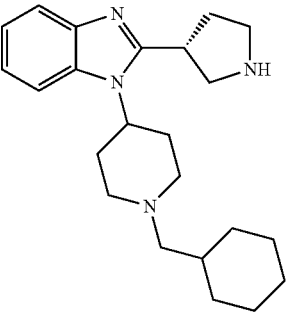 | 30 | x | high | x |
| 57 | 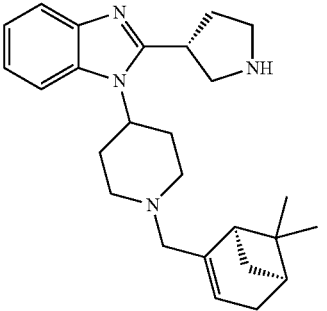 [SMILES: CC1(C)[C@H]2CC=C(CN3CCC(n4c([C@@H]5CCNC5)nc5ccccc54)CC3)[C@@H]1C2] | 25 | x | high | x |

-continued

| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 58 | 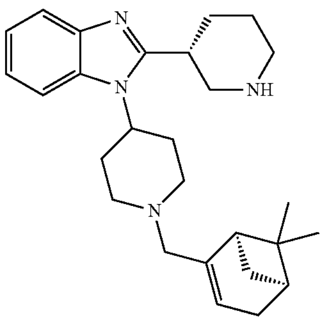 [SMILES: CC1(C)[C@H]2CC=C(CN3CCC(n4c([C@@H]5CCCNC5)nc5ccccc54)CC3)[C@@H]1C2] | 1600 | x | high | x |
| 59 | 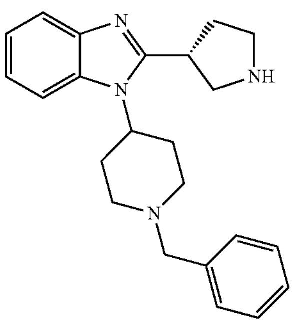 [SMILES: c1ccc(CN2CCC(n3c([C@@H]4CCNC4)nc4ccccc43)CC2)cc1] | 370 | x | 270 | x |
| 64 | 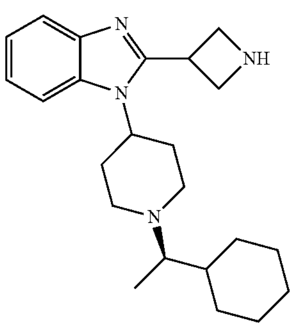 [SMILES: C[C@H](C1CCCCC1)N1CCC(n2c(C3CNC3)nc3ccccc32)CC1] | 4.8 | x | 2.7 | x |
| 65 | 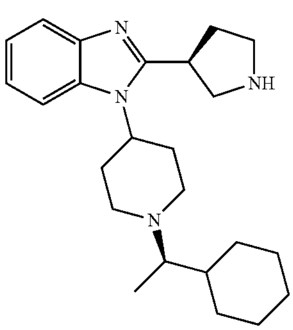 [SMILES: C[C@H](C1CCCCC1)N1CCC(n2c([C@H]3CCNC3)nc3ccccc32)CC1] | 1.1 | x | 1.0 | x |

-continued

| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 68 | 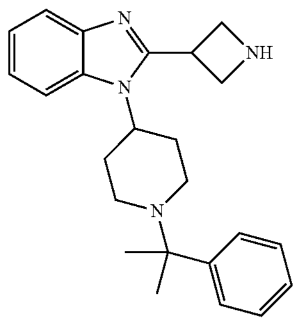 [SMILES: CC(C)(c1ccccc1)N1CCC(n2c(C3CNC3)nc3ccccc32)CC1] | 4.8 | x | 4.0 | x |
| 69 | 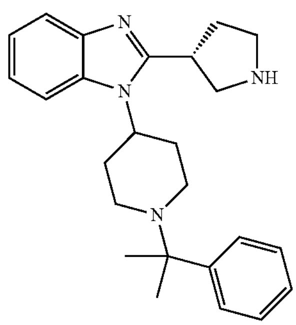 [SMILES: CC(C)(c1ccccc1)N1CCC(n2c([C@@H]3CCNC3)nc3ccccc32)CC1] | 0.42 | x | 1.1 | x |
| 70 | 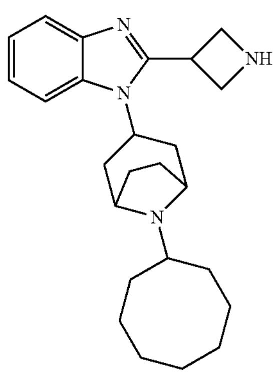 [SMILES: c1ccc2c(c1)nc(C1CNC1)n2C1CC2CCC(C1)N2C1CCCCCCC1] | 1.4 | x | high | x |
| 71 | 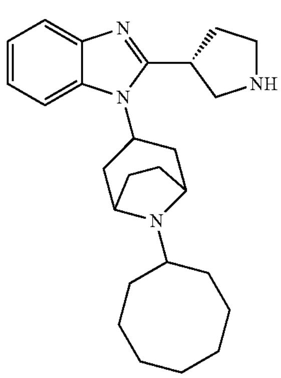 [SMILES: c1ccc2c(c1)nc([C@@H]1CCNC1)n2C1CC2CCC(C1)N2C1CCCCCCC1] | 0.24 | x | 160 | x |

-continued
| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 72 | 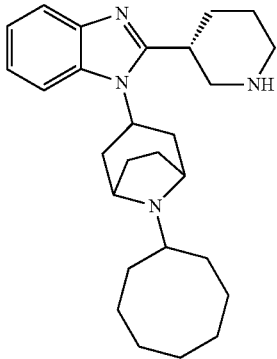 [SMILES: c1ccc2c(c1)nc([C@@H]1CCCNC1)n2C1CC2CCC(C1)N2C1CCCCCCC1] | 1.3 | x | 58 | x |
| 83 | 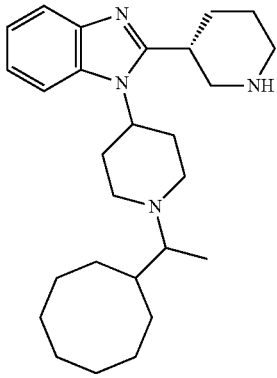 [SMILES: CC(C1CCCCCCC1)N1CCC(n2c([C@@H]3CCCNC3)nc3ccccc32)CC1] | 15 | 3400 | 3.0 | 21000 |
| 85 | 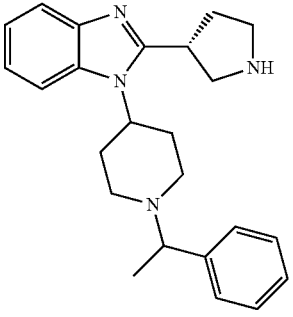 [SMILES: CC(c1ccccc1)N1CCC(n2c([C@@H]3CCNC3)nc3ccccc32)CC1] | 17 | x | 11 | x |
| 86 | 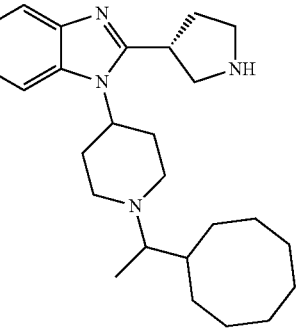 | 0.63 | 33 | 4.7 | x |

-continued

| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 87 | 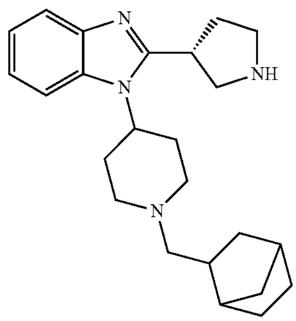 [SMILES: c1ccc2c(c1)nc([C@@H]1CCNC1)n2C1CCN(CC2CC3CCC2C3)CC1] | 3.1 | 7800 | 420 | 24000 |
| 88 | 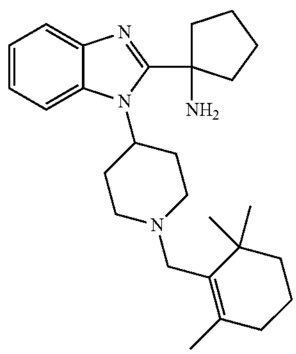 [SMILES: CC1=C(CN2CCC(n3c(C4(N)CCCC4)nc4ccccc43)CC2)C(C)(C)CCC1] | 0.52 | x | high | x |
| 89 | 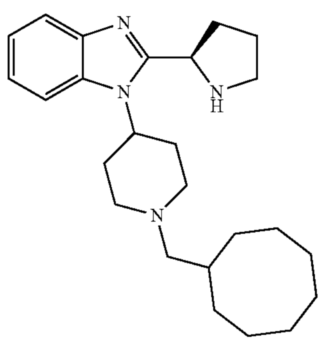 [SMILES: c1ccc2c(c1)nc([C@H]1CCCN1)n2C1CCN(CC2CCCCCCC2)CC1] | 15 | X | 150 | x |

Compounds below have been screened in NOP agonist mode only, at 10 μM

| 90 | | ≤10 μM | | | |

-continued

| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 93 | 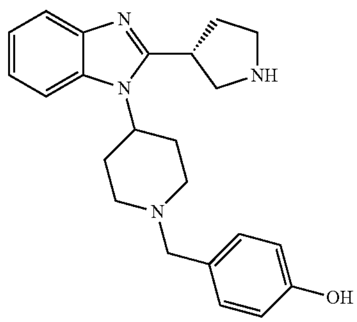 [SMILES: Oc1ccc(CN2CCC(n3c([C@@H]4CCNC4)nc4ccccc43)CC2)cc1] | | ≤10 μM | | |
| 96 | 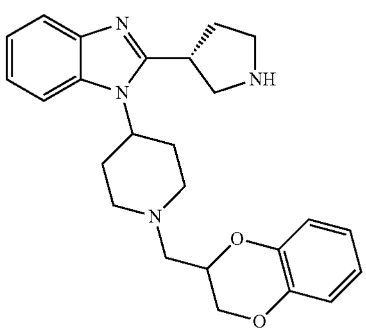 [SMILES: c1ccc2c(c1)OCC(CN1CCC(n3c([C@@H]4CCNC4)nc4ccccc43)CC1)O2] | | ≤10 μM | | |
| 98 | 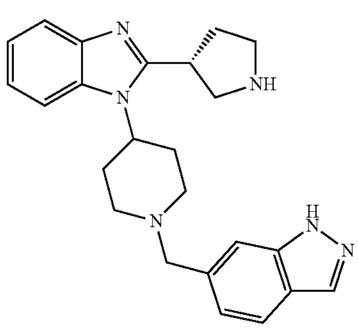 [SMILES: c1ccc2c(c1)nc([C@@H]1CCNC1)n2C1CCN(Cc2ccc3cn[nH]c3c2)CC1] | | ≤10 μM | | |
| 99 | 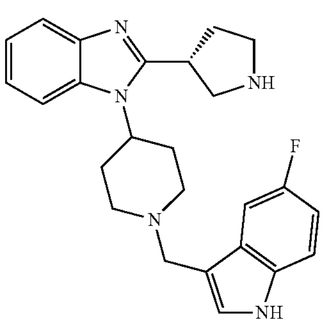 [SMILES: Fc1ccc2[nH]cc(CN3CCC(n4c([C@@H]5CCNC5)nc5ccccc54)CC3)c2c1] | | ≤10 μM | | |

-continued
| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 101 | 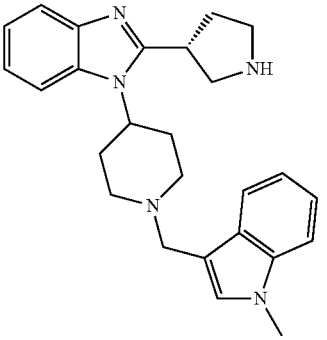 [SMILES: Cn1cc(CN2CCC(n3c([C@@H]4CCNC4)nc4ccccc43)CC2)c2ccccc21] | ≤10 μM | | | |
| 103 | 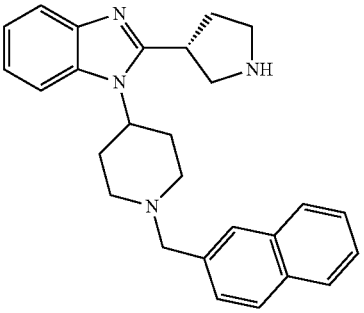 [SMILES: c1ccc2cc(CN3CCC(n4c([C@@H]5CCNC5)nc5ccccc54)CC3)ccc2c1] | ≤10 μM | | | |
| 104 | 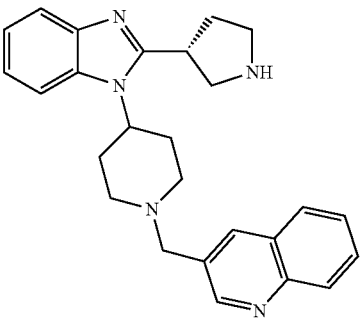 [SMILES: c1ccc2ncc(CN3CCC(n4c([C@@H]5CCNC5)nc5ccccc54)CC3)cc2c1] | ≤10 μM | | | |
| 105 | 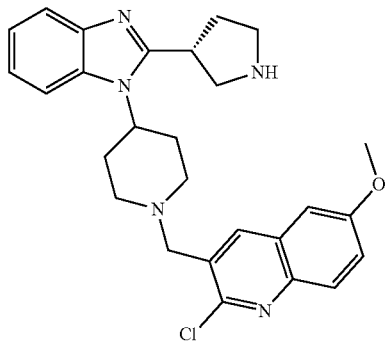 [SMILES: COc1ccc2nc(Cl)c(CN3CCC(n4c([C@@H]5CCNC5)nc5ccccc54)CC3)cc2c1] | ≤10 μM | | | |

| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
| --- | --- | --- | --- | --- | --- |
| 106 | 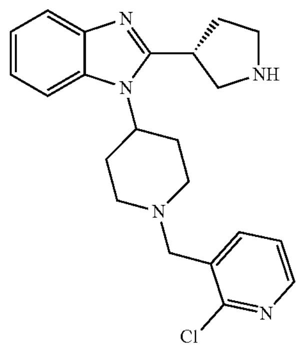 [SMILES: Clc1ncccc1CN1CCC(n2c([C@@H]3CCNC3)nc3ccccc32)CC1] | ≤10 μM | | | |
| 107 | 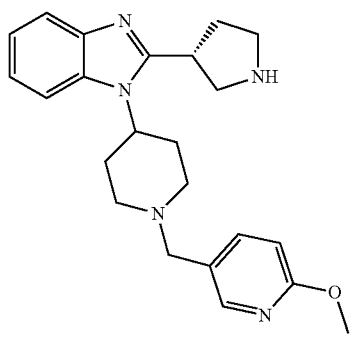 [SMILES: COc1ccc(CN2CCC(n3c([C@@H]4CCNC4)nc4ccccc43)CC2)cn1] | ≤10 μM | | | |
| 108 | 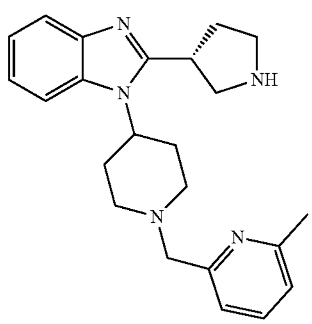 [SMILES: Cc1cccc(CN2CCC(n3c([C@@H]4CCNC4)nc4ccccc43)CC2)n1] | ≤10 μM | | | |
| 110 | 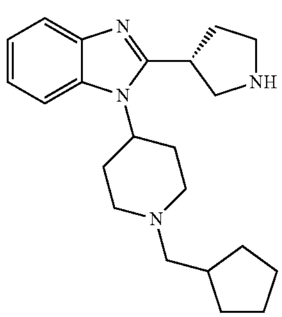 [SMILES: c1ccc2c(c1)nc([C@@H]1CCNC1)n2C1CCN(CC2CCCC2)CC1] | ≤10 μM | | | |

-continued
| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 111 | 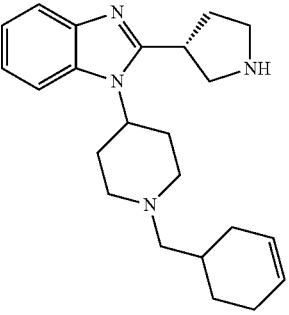 | ≤10 μM | | | |
| 112 | 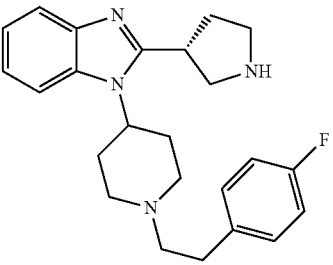 [SMILES: Fc1ccc(CCN2CCC(n3c([C@@H]4CCNC4)nc4ccccc43)CC2)cc1] | ≤10 μM | | | |
| 116 | 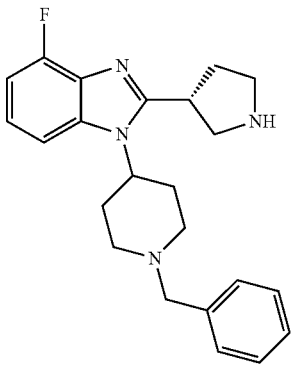 [SMILES: Fc1cccc2c1nc([C@@H]1CCNC1)n2C1CCN(Cc2ccccc2)CC1] | ≤10 μM | | | |
| 118 | 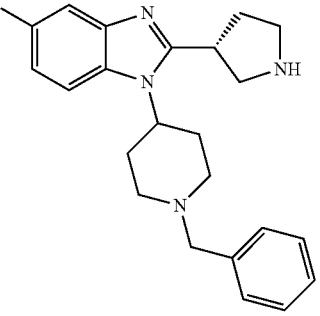 | ≤10 μM | | | |

| Cpd # | Structure | NOP Agonist EC$_{50}$ (nM) | NOP Antagonist IC$_{50}$ (nM) | MOP Agonist EC$_{50}$ (nM) | MOP Antagonist IC$_{50}$ (nM) |
|---|---|---|---|---|---|
| 121 | 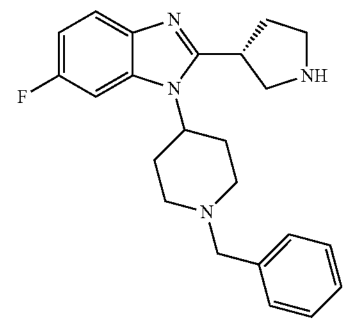 [SMILES: Fc1ccc2nc([C@@H]3CCNC3)n(C3CCN(Cc4ccccc4)CC3)c2c1] | ≤10 μM | | | |

* EC$_{50}$ and IC$_{50}$ values, when shown, are representative and are shown to two significant figures. These values can change as environmental conditions fluctuate (error bars are not indicated) and thus they convey an estimation of the binding affinity of the compounds to the receptors indicated.

Evaluations

It is within ordinary skill to evaluate any compound disclosed and claimed herein for effectiveness in modulating the activity of NOP, by assessment of antagonism or agonism of NOP in various cellular assays, using the procedures described above or found in the scientific literature. Accordingly, the person of ordinary skill can prepare and evaluate any of the claimed compounds without undue experimentation.

Any compound found to be an effective antagonist or agonist of NOP (including partial agonism, inverse agonism, and functionally biased agonism) can likewise be tested in animal models and in human clinical studies using the skill and experience of the investigator to guide the selection of dosages and treatment regimens.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A compound of formula (I)

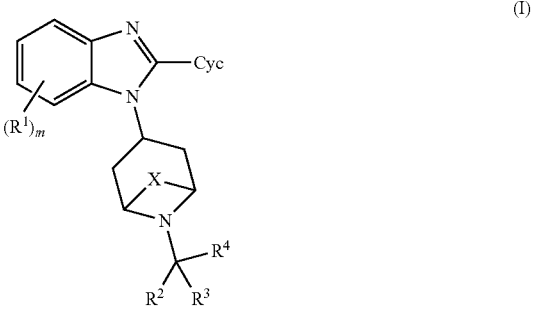

(I)

wherein
X is (CHR)$_n$ wherein n=1, 2, or 3; or X is absent;
R$^1$ is halo, nitro, cyano, (C1-C6)alkyl, (C1-C6)haloalkyl, (C1-C6)alkylsulfonyl, (C1-C6)alkoxy, trifluoromethoxy, or (C1-C6)haloalkylsulfonyl, and m=0, 1, or 2;
R$^2$ and R$^3$ are independently H, (C1-C6)alkyl, (C1-C6) alkyl substituted with 1-5 fluorine atoms, or (C1-C6) cycloalkyl;
R$^4$ is (C1-C10)alkyl, (C3-C10) mono- or bicyclic cycloalkyl, (C3-C10) mono- or bicyclic cycloalkenyl, (C3-C10) mono- or bicyclic cycloalkyl(C1-C6)alkyl, (C3-C10) mono- or bicyclic cycloalkyl(C1-C6)alkenyl, or 3- to 14-membered mono-or bi-cyclic heterocyclyl, wherein any alkyl, cycloalkyl or heterocyclyl is optionally unsaturated, or R$^4$ is (C6-C14)aryl or is (C6-C14) aryl(C1-C6)alkyl, (5- to 14-membered heteroaryl), or (5- to 14-membered heteroaryl)-(C1-C6)alkyl, wherein any alkyl, cycloalkyl, cycloalkenyl, heterocyclyl, aryl or heteroaryl group is substituted with 0-3 J groups, and wherein any alkyl group can further comprise —O—, —N(R)—, —OC(O)N(R)—, —N(R)C(O)N(R)—, or —OC(O)O— therein; or,
when X is present, R$^3$ and R$^4$ together with the carbon atom to which they are bonded can form a (C3-C10) mono- or bicyclic cycloalkyl or 3-10-membered mono-or bicyclic heterocyclyl group or a (C6-C14) aryl group, any of which is substituted with 0-3 J; and Cyc is a group of formula (II)

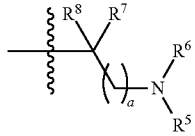

(II)

wherein a wavy line indicates a point of bonding; and, $R^7$ and $R^8$ together with the atoms to which they are bonded form a ring such that the group of formula (II) is of formula (IIB)

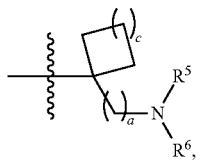

(IIB)

wherein a=0, 1, or 2 and c=0, 1, 2, 3, 4, or 5, and the ring is substituted with 0-3 J groups, optionally further comprising within the ring one heteroatom selected from O, NR, and $S(O)_q$ wherein q=0, 1, or 2; $R^5$ and $R^6$ are each independently H, acyl, or (C1-C6)alkyl, wherein any alkyl is substituted with 0-3 J; or, $R^5$ and $R^6$ together with the nitrogen atom to which they are bonded form a 3-9-membered heterocyclyl ring, substituted with 0-3 J groups, and optionally further comprising within the ring one heteroatom selected from O, NR, and $S(O)_q$ wherein q=0, 1, or 2, wherein the ring optionally comprises an unsaturation, or is optionally fused with a (C6-C14)aryl substituted with 0-3 J, or both; and, J is halo, nitro, cyano, R, $CF_3$, OR, $NR_2$, C(O)OR, C(O)$NR_2$, OC(O)OR, OC(O)$NR_2$, N(R)C(O)OR, N(R) C(O)$NR_2$ or thio/thiono analogs thereof; or two J groups together are methylenedioxy or ethylenedioxy; and, each independently selected R is H, (C1-C6)alkyl, (C1-C6)acyl, (C6-C14)aryl, (C6-C14)aryl(C1-C6)alkyl, or (C6-C14)aroyl, wherein any non-hydrogen R is substituted with 0-3 $J^R$;

$J^R$ is halo, nitro, cyano, $CF_3$, OR, $NR_2$, C(O)OR, C(O)$NR_2$, OC(O)OR, OC(O)$NR_2$, N(R)C(O)OR, N(R)C(O)$NR_2$ or thio/thiono analogs thereof; or two $J^R$ groups together are methylenedioxy or ethylenedioxy;

or a pharmaceutically acceptable salt thereof.

2. The compound of claim 1 wherein for the group of formula (IIB), c=0, 1, 2, or 3, and $R^5$ and $R^6$ are independently H, methyl, or acyl.

3. A compound of formula (I)

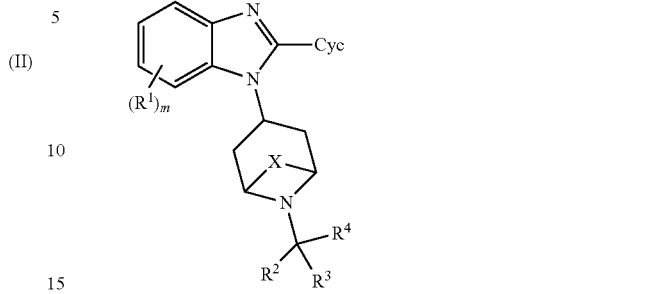

(I)

wherein

X is $CH_2$ or $CH_2CH_2$, $R^2$ is H or methyl, $R^3$ is H, and $R^4$ is cyclopentyl, cyclohexyl, cycloheptyl, cyclooctyl, n-heptan-3-yl, 2,6,6,-trimethylcyclohex-1-enyl, 6,6-dimethylbicyclo[3.1.1]hept-2-yl, bicyclo[2.2.1]hept-2-en-5-yl, piperidin-4-yl, tetrahydropyran-4-yl, phenyl, 3-indolyl, 5-benzimidazolyl, 6-indazolyl, 3-quinolyl, 2-naphthyl, 2-benzothiazolyl, 2-pyridyl, 3-pyridyl, 4-pyridyl, and members of these aryl and heteroaryl groups bering one or more halogen, alkyl, haloalkyl, or alkoxy substitutents;

Cyc is a group of formula (II)

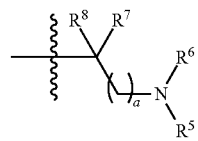

(II)

wherein a wavy line indicates a point of bonding; and, (a) a=0, 1, 2, 3, 4, or 5; and $R^5$, $R^6$, $R^7$ and $R^8$ are each independently H, (C1-C6)alkyl, or (C1-C6)acyl, wherein any alkyl or acyl is substituted with 0-3 J; or, (b) $R^6$ and $R^7$ together with the atoms to which they are bonded form a heterocyclyl ring such that the group of formula (II) is of formula (IIA)

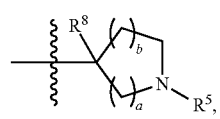

(IIA)

wherein a=0, 1, or 2, and b=0, 1, or 2; optionally further comprising within the heterocyclyl ring 1-2 additional heteroatom independently selected from O, NR, and $S(O)_q$ wherein q=0, 1, or 2; and wherein the ring is substituted with 0-3 J groups; $R^5$ is H, alkyl, cycloalkyl, acyl, or aroyl; and, $R^8$ is H, alkyl, or cycloalkyl; wherein any non-hydrogen $R^5$ or $R^8$ group is substituted with 0-3 J groups; or, $R^5$ and $R^8$ can together form a (C3-C5)alkylene bridge; and, wherein the ring optionally comprises an unsaturation, or is optionally fused with a (C6-C14)aryl substituted with 0-3 J, or both; or, (c) R⁷ and R⁸ together with the atoms to which they are bonded form a ring such that the group of formula (II) is of formula (IIB)

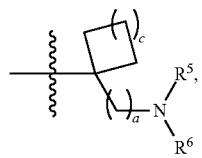
(IIB)

wherein a=0, 1, or 2 and c=0, 1, 2, 3, 4, or 5, and the ring is substituted with 0-3 J groups, optionally further comprising within the ring one heteroatom selected from O, NR, and S(O)$_q$ wherein q=0, 1, or 2; R⁵ and R⁶ are each independently H, acyl, or (C1-C6)alkyl, wherein any alkyl is substituted with 0-3 J; or, R⁵ and R⁶ together with the nitrogen atom to which they are bonded form a 3-9-membered heterocyclyl ring, substituted with 0-3 J groups, and optionally further comprising within the ring one heteroatom selected from O, NR, and S(O)$_q$ wherein q=0, 1, or 2, wherein the ring optionally comprises an unsaturation, or is optionally fused with a (C6-C14)aryl substituted with 0-3 J, or both; and, J is halo, nitro, cyano, R, CF₃, OR, NR₂, C(O)OR, C(O)NR₂, OC(O)OR, OC(O)NR₂, N(R)C(O)OR, N(R)C(O)NR₂ or thio/thiono analogs thereof; or two J groups together are methylenedioxy or ethylenedioxy; and, each independently selected R is H, (C1-C6)alkyl, (C1-C6)acyl, (C6-C14)aryl, (C6-C14)aryl(C1-C6)alkyl, or (C6-C14)aroyl, wherein any non-hydrogen R is substituted with 0-3 J$^R$;

J$^R$ is halo, nitro, cyano, CF₃, OR, NR₂, C(O)OR, C(O)NR₂, OC(O)OR, OC(O)NR₂, N(R)C(O)OR, N(R)C(O)NR₂ or thio/thiono analogs thereof; or two J$^R$ groups together are methylenedioxy or ethylenedioxy;

or a pharmaceutically acceptable salt thereof.

4. The compound of claim 3 in which R² is H.

5. A compound wherein the compound has any of the following chemical structures, including all isomeric forms thereof:

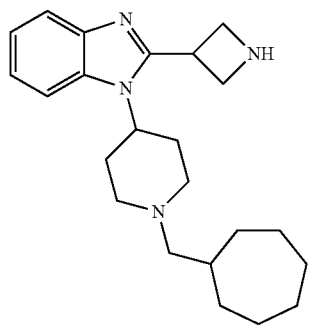

-continued

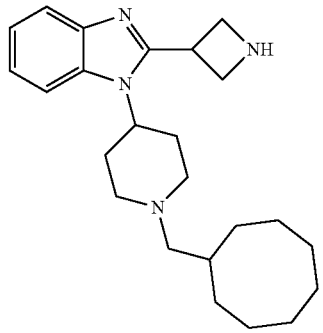

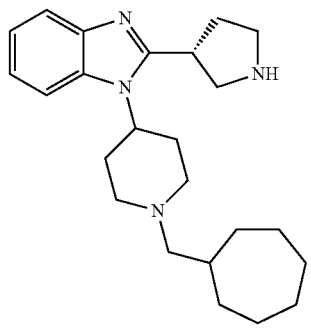

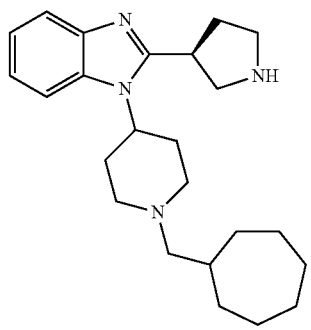

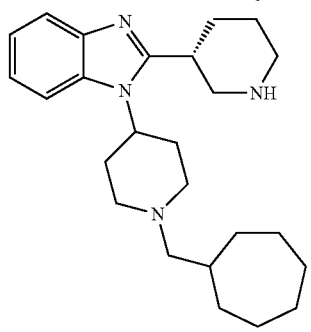

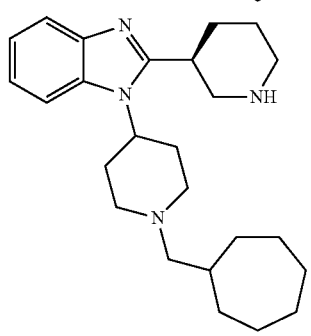

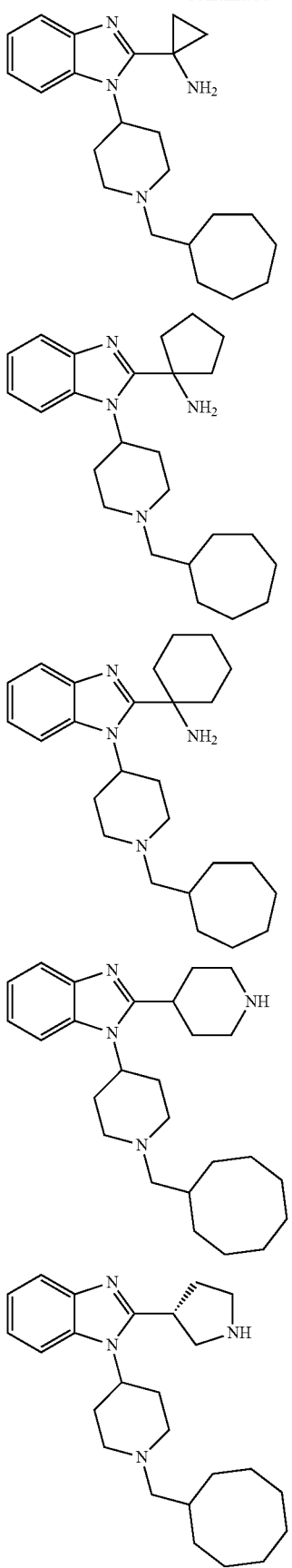

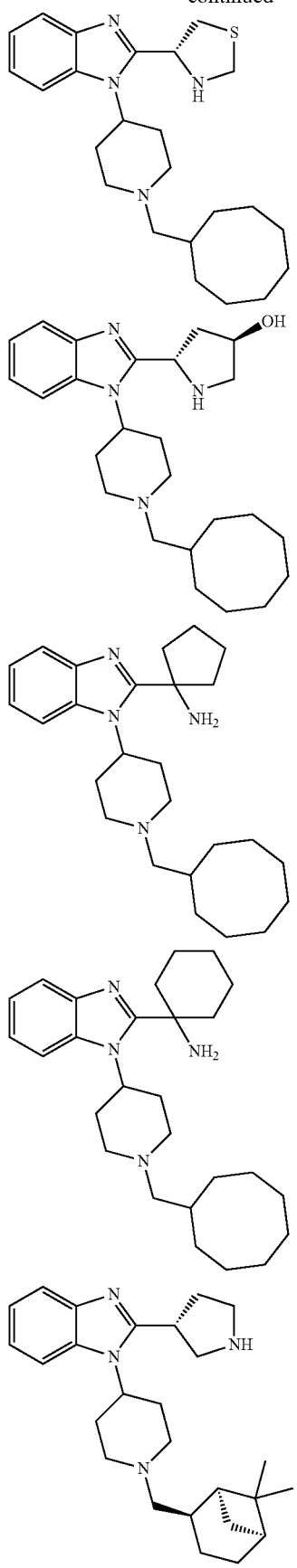
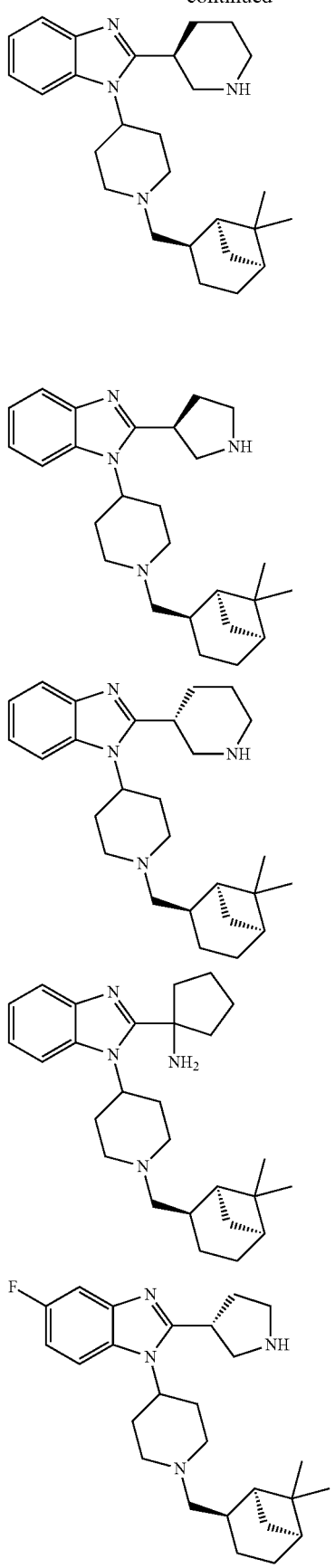

195
-continued
196
-continued
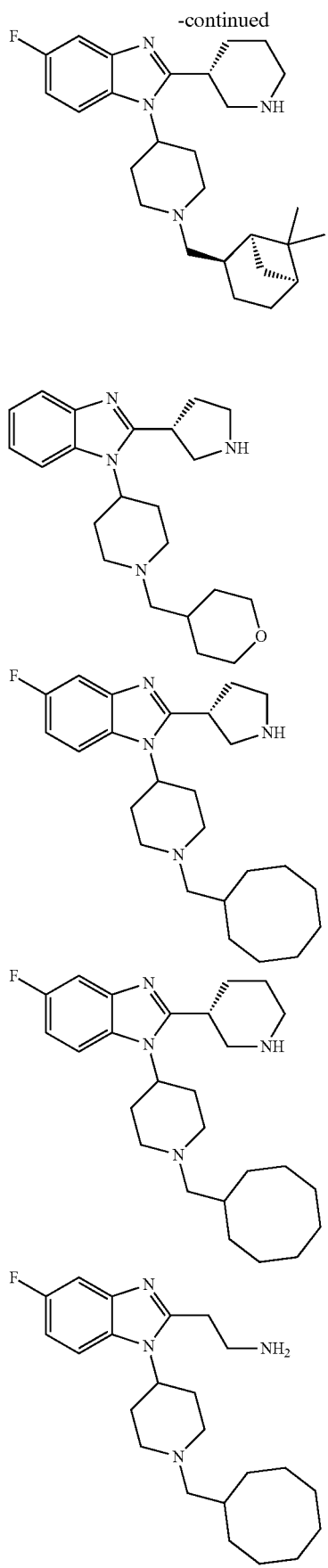
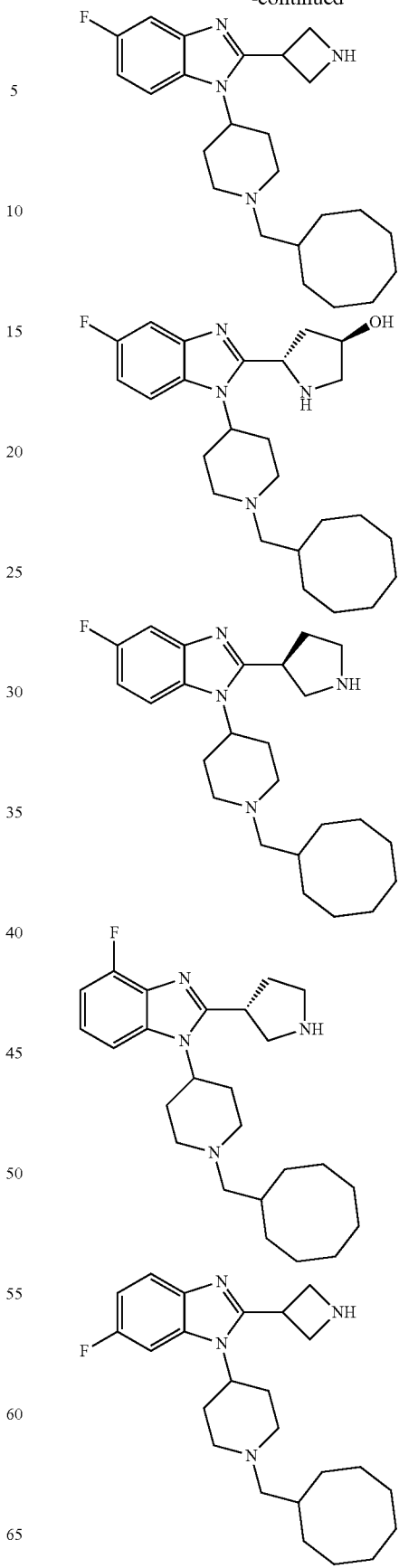

197
-continued
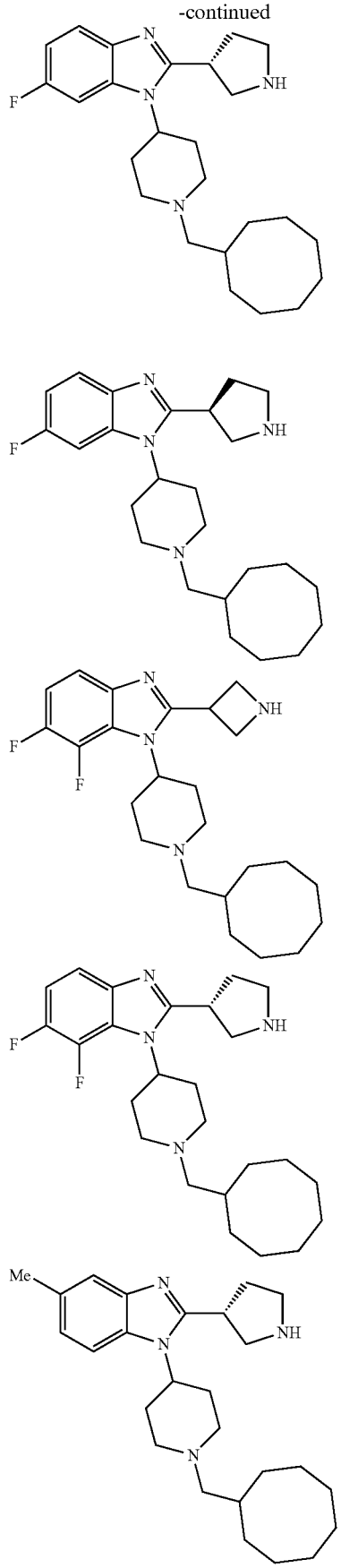
198
-continued
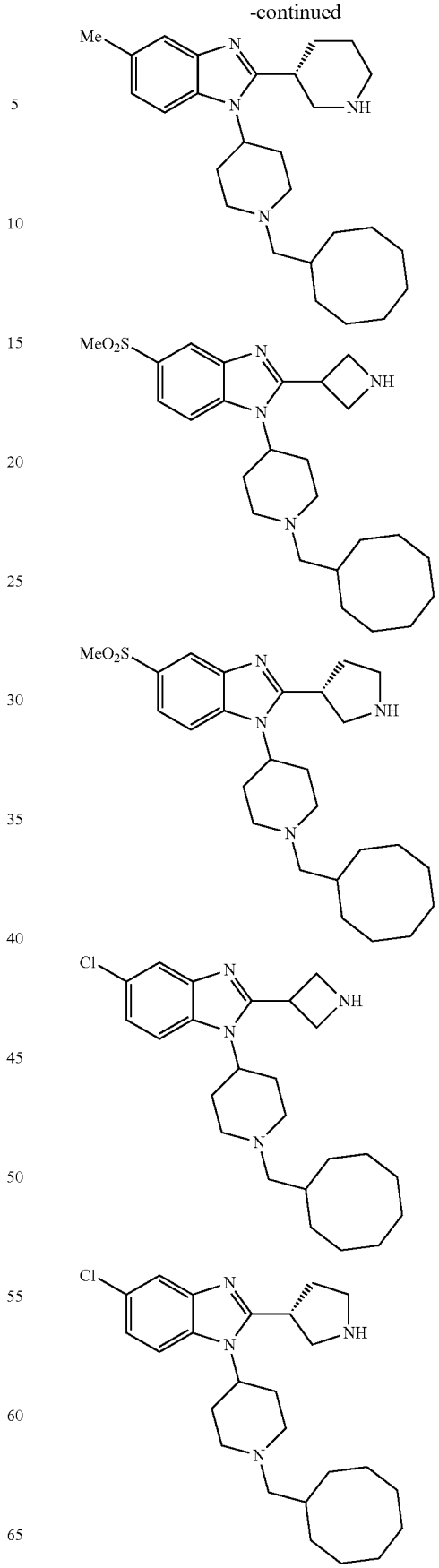

199
-continued
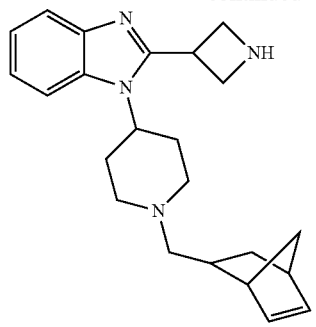
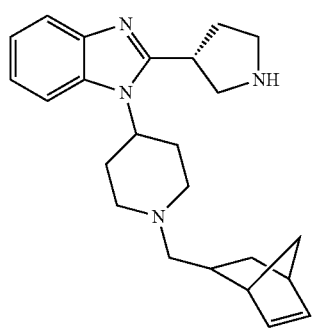
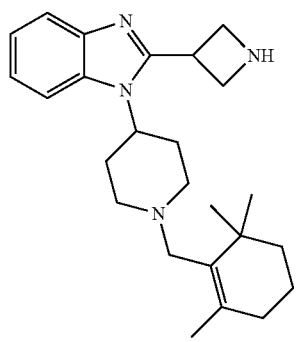
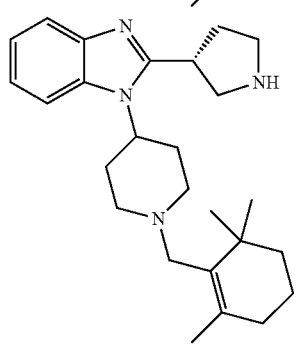
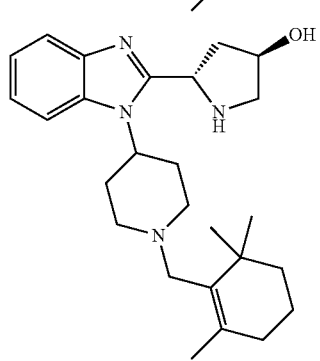
200
-continued
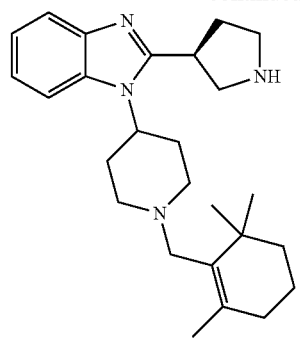
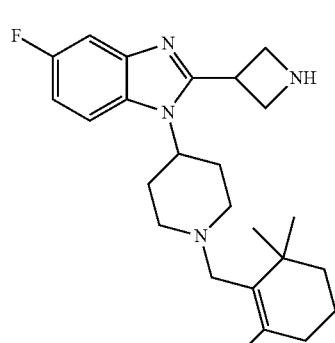
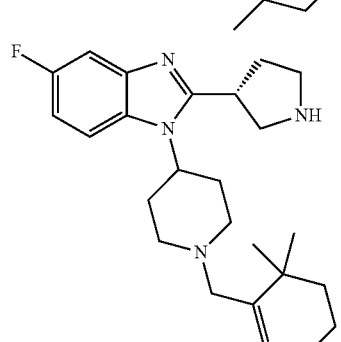
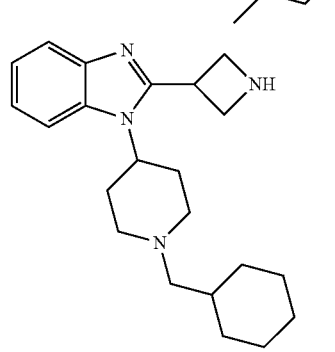
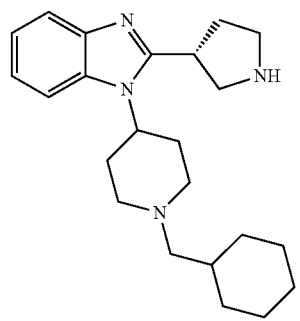

US 9,656,994 B2
201
-continued
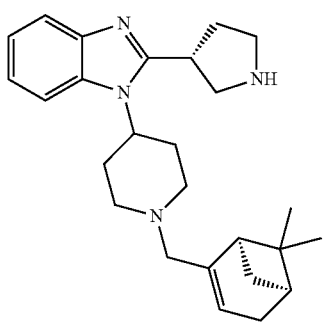
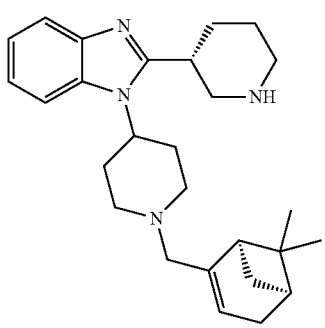
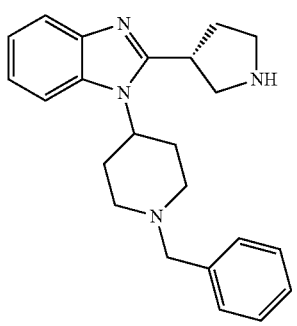
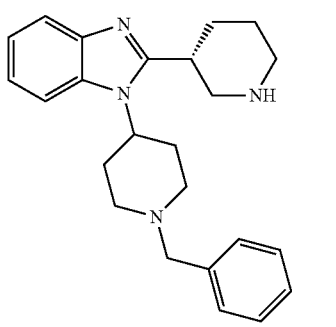
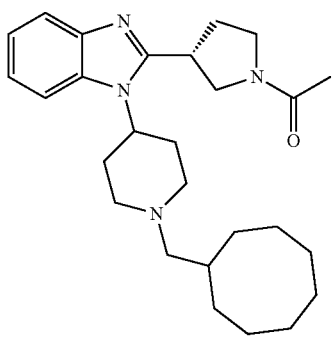
202
-continued
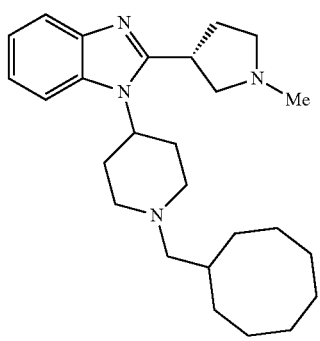
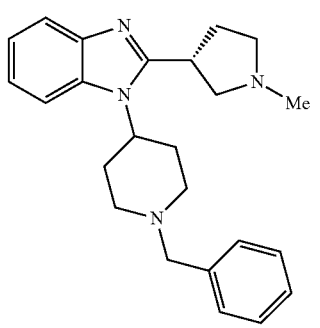
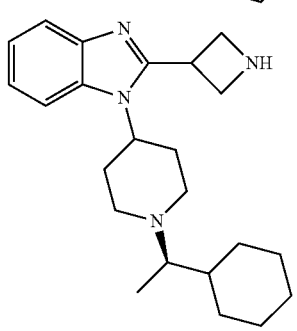
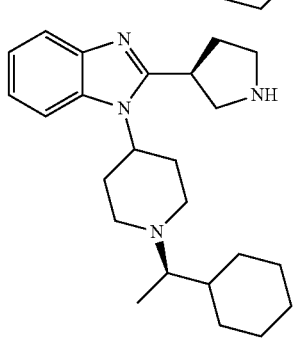
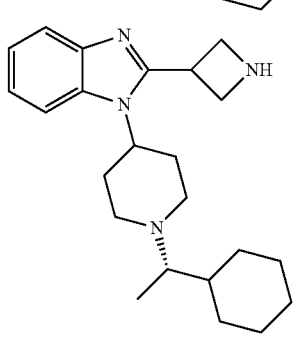

203
-continued
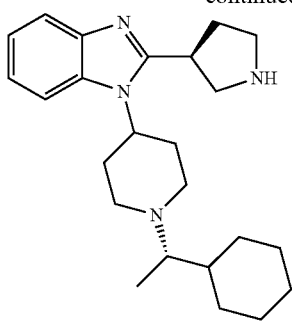
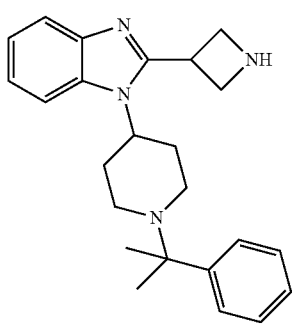
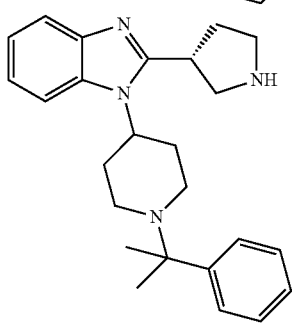
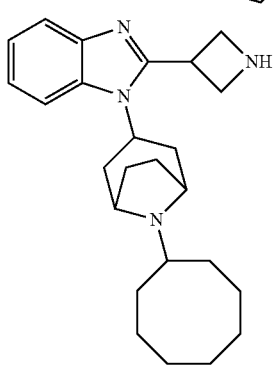
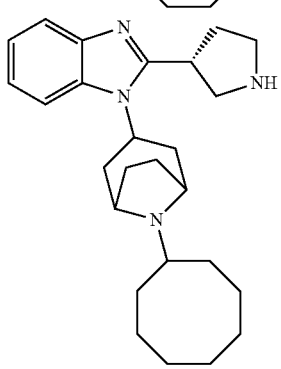
204
-continued
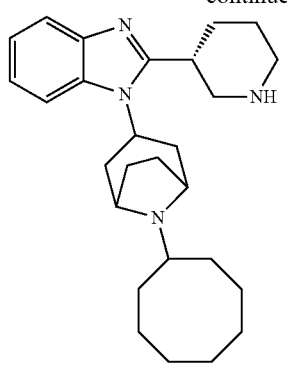
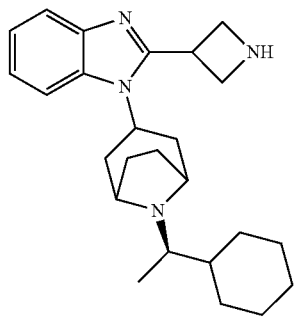
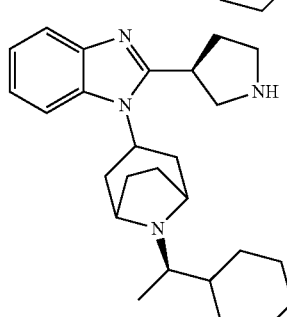
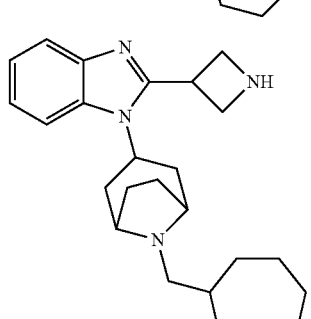
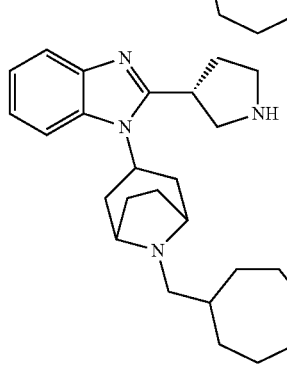

205
-continued
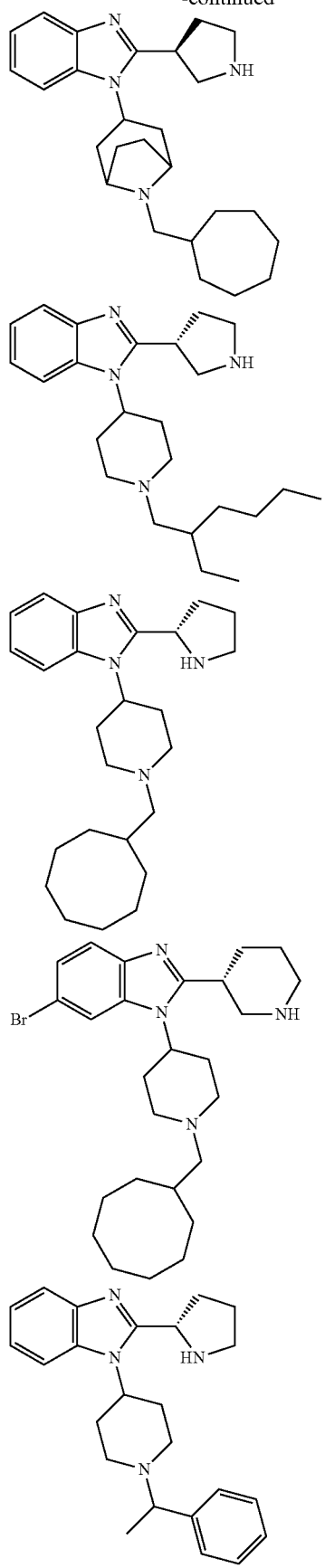
206
-continued
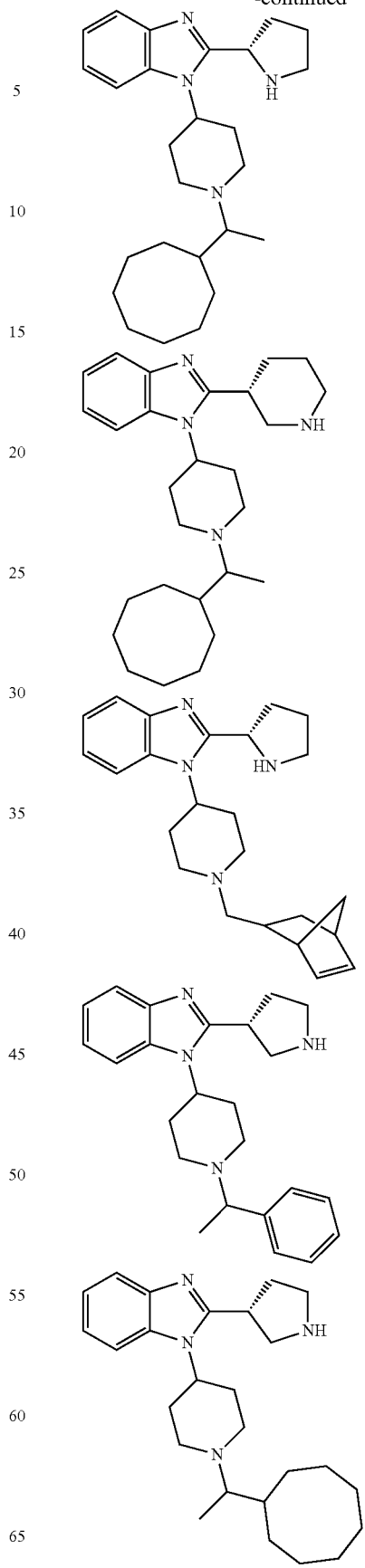

207
-continued
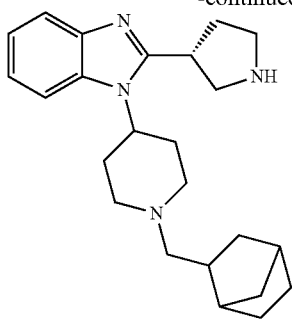
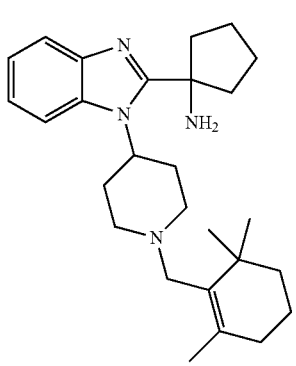
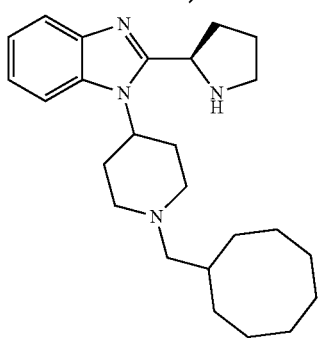
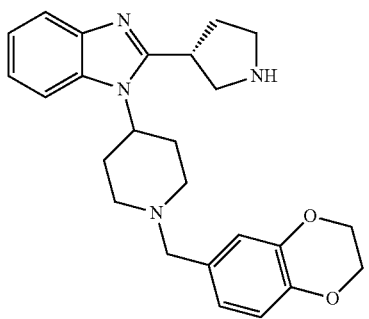
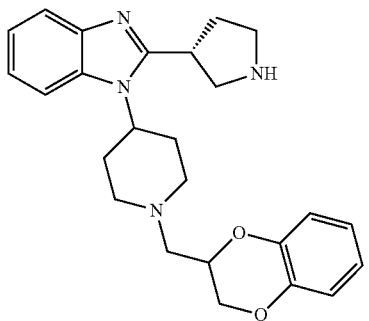
208
-continued
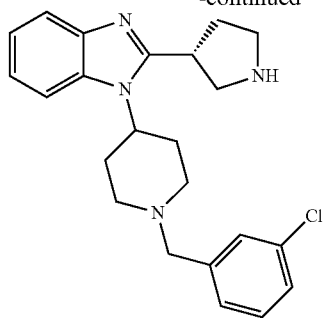
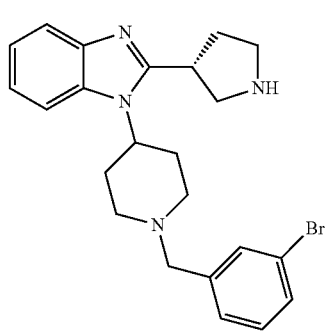
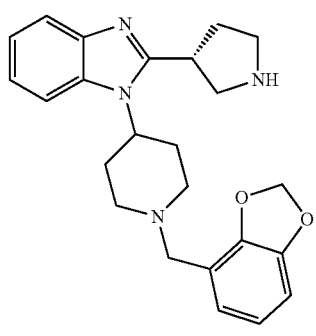
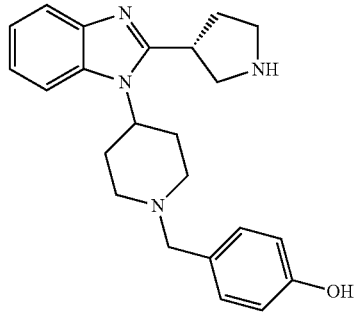
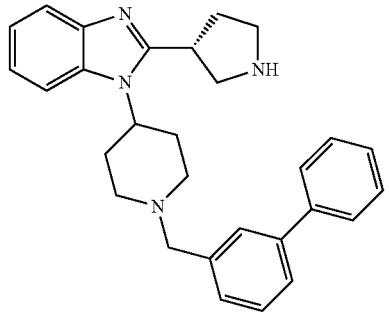

209
-continued
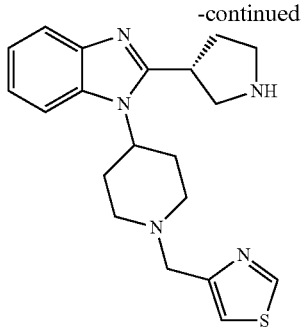
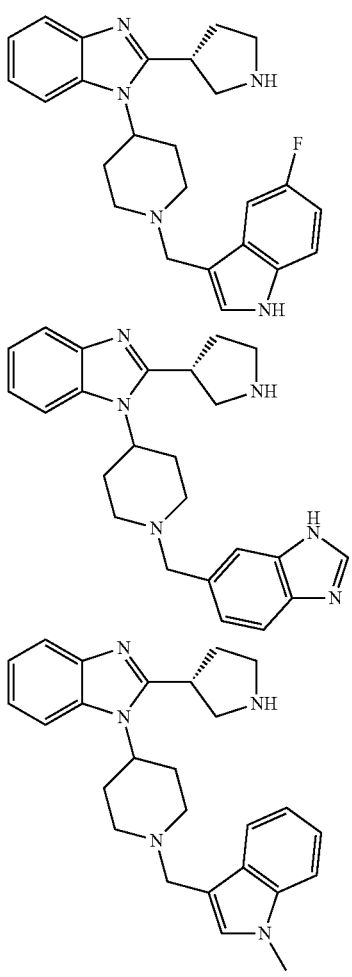
210
-continued
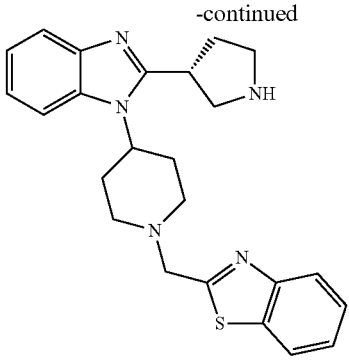
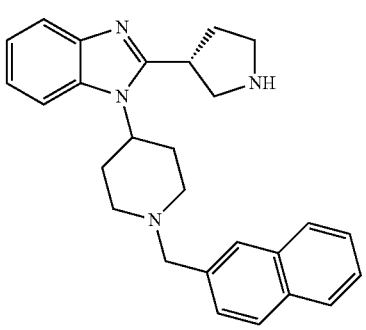
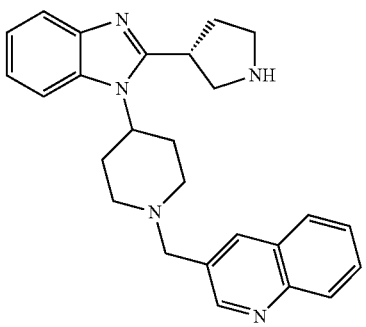
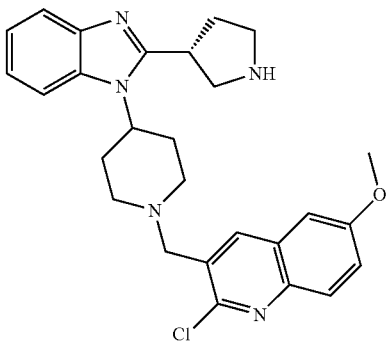
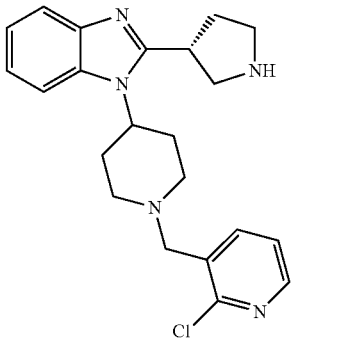

211
-continued
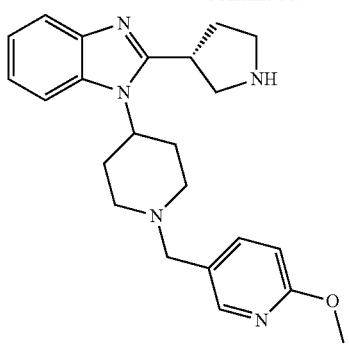
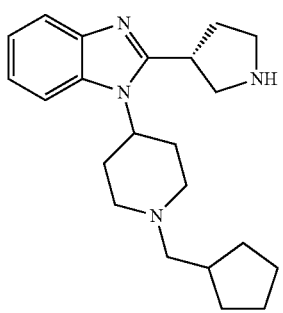
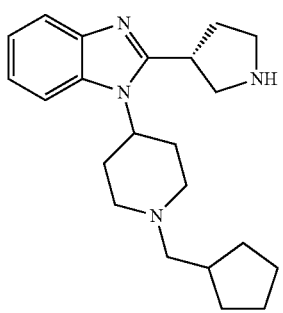
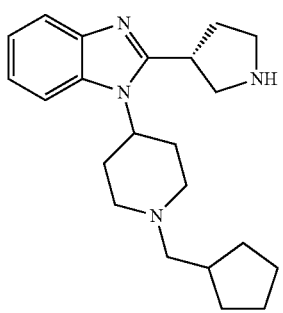
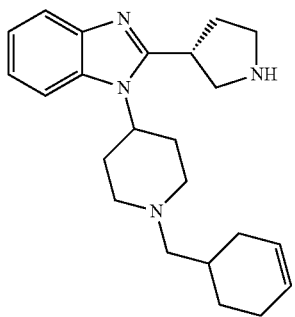
212
-continued
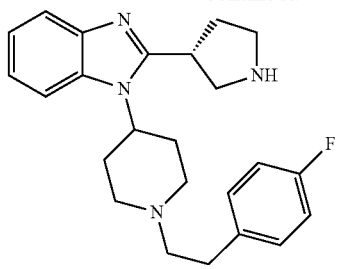
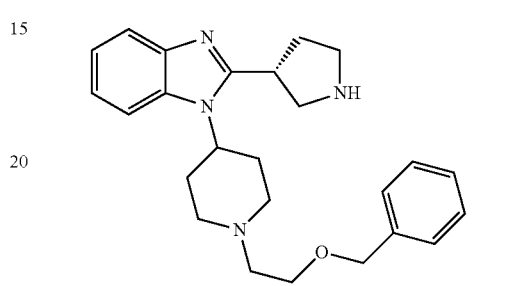
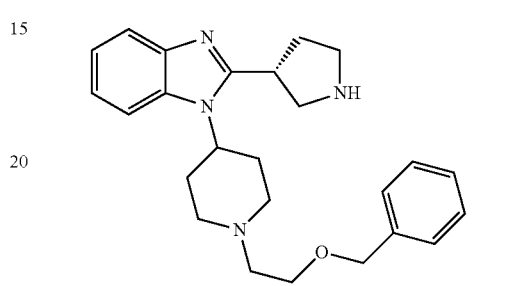
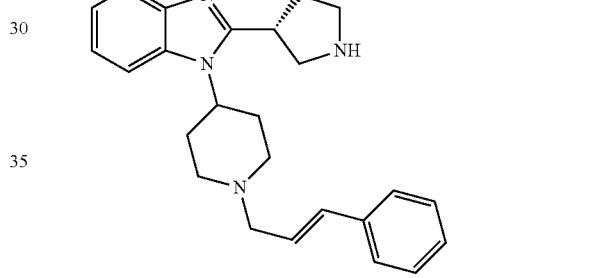
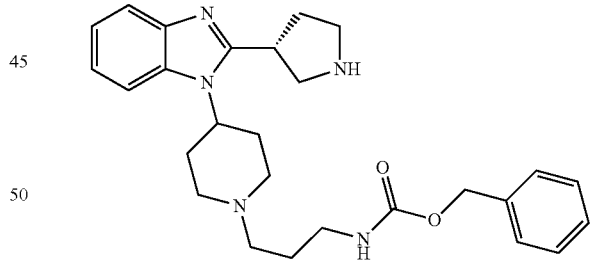
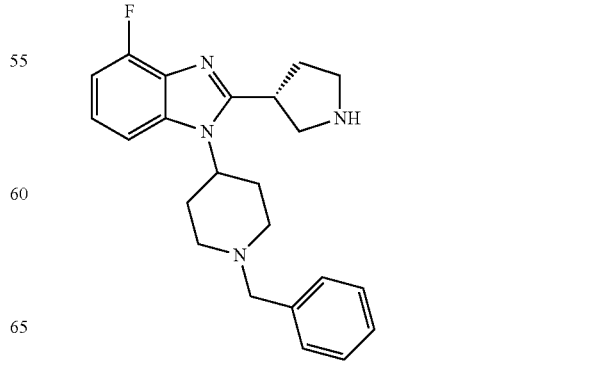

213
-continued
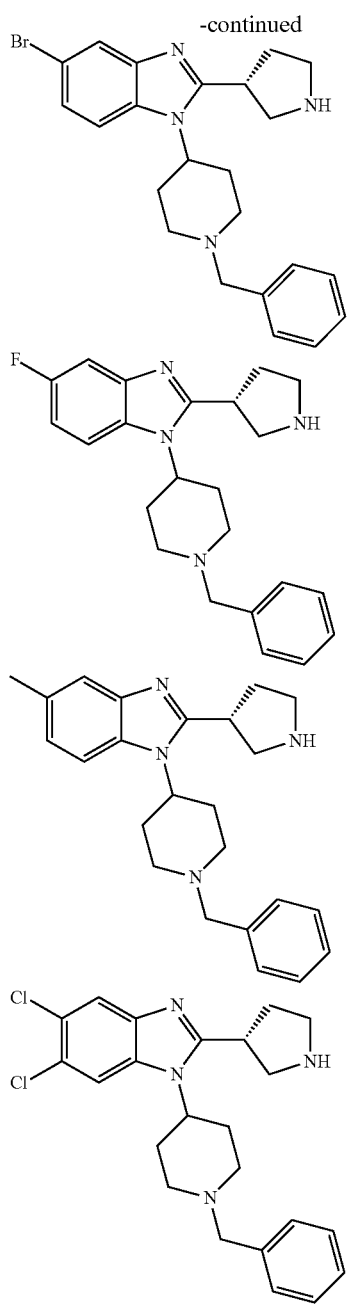
214
-continued
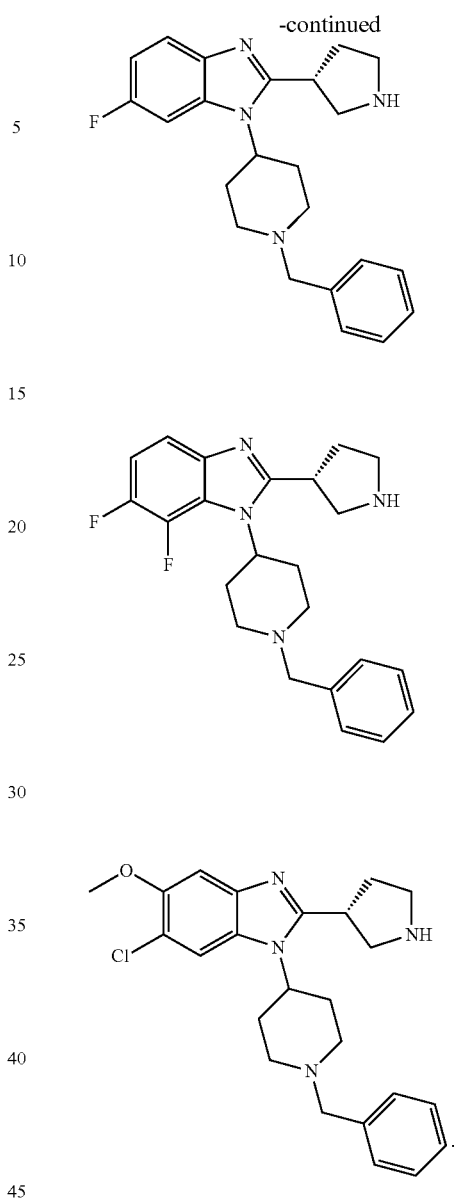
6. A pharmaceutical composition comprising a compound of any one of claims 1, 2, 3, 4, and 5, and a pharmaceutically acceptable excipient.
* * * * *

UNITED STATES PATENT AND TRADEMARK OFFICE
CERTIFICATE OF CORRECTION

PATENT NO. : 9,656,994 B2
APPLICATION NO. : 14/779191
DATED : May 23, 2017
INVENTOR(S) : Bannister et al.

Page 1 of 1

It is certified that error appears in the above-identified patent and that said Letters Patent is hereby corrected as shown below:

In the Specification

Column 1, Lines 18-22, the paragraph STATEMENT OF GOVERNMENT SUPPORT should be changed to:
-- STATEMENT OF GOVERNMENT LICENSE RIGHTS
This invention was made with government support under grant number AA017943 awarded by the National Institutes of Health. The government has certain rights in the invention. --

Signed and Sealed this
Fifth Day of May, 2020

Andrei Iancu
*Director of the United States Patent and Trademark Office*